US007998749B2

(12) United States Patent
Gilmore et al.

(10) Patent No.: US 7,998,749 B2
(45) Date of Patent: Aug. 16, 2011

(54) ASSAYS OF MOLECULAR OR SUBCELLULAR INTERACTIVITY USING DEPOLARIZATION AFTER RESONANCE TRANSFER ENERGY (DARET)

(75) Inventors: Marcella A. Gilmore, Santa Ana, CA (US); Dudley J. Williams, Laguna Niguel, CA (US); Lance E. Steward, Irvine, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 505 days.

(21) Appl. No.: 11/548,411

(22) Filed: Oct. 11, 2006

(65) Prior Publication Data

US 2007/0275477 A1     Nov. 29, 2007

Related U.S. Application Data

(60) Provisional application No. 60/726,515, filed on Oct. 12, 2005.

(51) Int. Cl.
*G01N 27/76* (2006.01)
*G01N 33/00* (2006.01)
*C12Q 1/68* (2006.01)
*C12Q 1/26* (2006.01)
*C07H 21/04* (2006.01)

(52) U.S. Cl. ............. 436/172; 435/6; 435/23; 435/174; 435/254; 436/86; 536/23.1; 536/24.3; 702/19

(58) Field of Classification Search ................. None
See application file for complete search history.

(56) References Cited

U.S. PATENT DOCUMENTS

| | | | |
|---|---|---|---|
| 4,211,762 A | 7/1980 | Higgins et al. | |
| 5,981,200 A * | 11/1999 | Tsien et al. | 435/7.4 |
| 6,107,066 A | 8/2000 | Tsien et al. | |
| 6,197,534 B1 | 3/2001 | Lakowicz et al. | |
| 6,291,201 B1 | 9/2001 | Garman | |
| 6,337,386 B1 | 1/2002 | Shone et al. | |
| 6,342,379 B1 | 1/2002 | Tsien et al. | |
| 6,428,954 B1 | 8/2002 | Wells et al. | |
| 6,432,632 B2 | 8/2002 | Nakayama et al. | |
| 6,444,421 B1 | 9/2002 | Chung | |
| 6,503,719 B2 * | 1/2003 | Modlin et al. | 435/6 |
| 6,596,522 B2 | 7/2003 | Tsien et al. | |
| 6,713,262 B2 | 3/2004 | Gellibolian et al. | |
| 6,723,525 B2 | 4/2004 | Normant et al. | |
| 6,942,987 B2 | 9/2005 | Auld | |
| 7,029,905 B1 | 4/2006 | Sippel et al. | |
| 7,101,681 B1 | 9/2006 | Lustig et al. | |
| 7,183,066 B2 | 2/2007 | Fernandez-Salas et al. | |

(Continued)

OTHER PUBLICATIONS

Mattheyses et al., "Fluorescence Resonance Energy Transfer Microscopy", Biophysical Journal, vol. 87, pp. 2787-2797 (Oct. 2004).*

(Continued)

*Primary Examiner* — Krishnan S Menon
*Assistant Examiner* — Dirk Bass
(74) *Attorney, Agent, or Firm* — Kenton Abel; Debra Condino

(57) ABSTRACT

The present invention provides a method of determining the proximity, or changes in the proximity of two or more molecular features labeled with fluorophores able to undergo DARET. In preferred embodiments the change in proximity of molecular features in a sample is correlated with changes in the fluorescence polarization of the sample, and may be monitored in real time.

14 Claims, 9 Drawing Sheets

Assay of BoNT/A 900 kDa Complex

U.S. PATENT DOCUMENTS

| | | | |
|---|---|---|---|
| 7,208,285 | B2 | 4/2007 | Steward et al. |
| 7,332,567 | B2 | 2/2008 | Steward et al. |
| 7,374,896 | B2 | 5/2008 | Steward et al. |
| 7,399,607 | B2 * | 7/2008 | Williams et al. ............ 435/23 |
| 7,495,069 | B2 | 2/2009 | Steward et al. |
| 2003/0003240 | A1 | 1/2003 | DeWent |
| 2005/0095601 | A1 | 5/2005 | Cullum et al. |
| 2006/0063222 | A1 | 3/2006 | Williams et al. |
| 2007/0122858 | A1 | 5/2007 | Fernandez-Salas et al. |
| 2007/0243565 | A1 | 10/2007 | Williams et al. |
| 2008/0064054 | A1 | 3/2008 | Fernandez-Salas et al. |
| 2008/0160561 | A1 | 7/2008 | Fernandez-Salas et al. |
| 2008/0166739 | A1 | 7/2008 | Steward et al. |
| 2008/0171348 | A1 | 7/2008 | Steward et al. |
| 2008/0176249 | A1 | 7/2008 | Steward et al. |
| 2008/0182799 | A1 | 7/2008 | Fernandez-Salas et al. |
| 2008/0213796 | A1 | 9/2008 | Steward et al. |
| 2008/0220456 | A1 | 9/2008 | Williams et al. |
| 2008/0293084 | A1 | 11/2008 | Williams et al. |
| 2008/0293085 | A1 | 11/2008 | Williams et al. |
| 2008/0305509 | A1 | 12/2008 | Williams et al. |
| 2008/0305510 | A1 | 12/2008 | Williams et al. |
| 2009/0042231 | A1 | 2/2009 | Steward et al. |
| 2009/0053746 | A1 | 2/2009 | Steward et al. |
| 2009/0117572 | A1 | 5/2009 | Fernandez-Salas et al. |

OTHER PUBLICATIONS

Office Action Date Mailed Jun. 20, 2008 in U.S. Appl. No. 10/598,073.

Keller, James E. et al, FEBS Letters, vol. 456, 1999, pp. 137-142, Persistence of botulinum neurotoxin action in cultured spinal cord cells.

Burke, T.J. et al., *Development and Application of Fluorescence Polarization Assays in Drug Discovery*, Chem. High Throughput Screen. 6(3): 183-194 (2003).

Clegg, R.M., *Fluorescence Resonance Transfer Energy*, Curr. Opin. Biotech. 6(1): 103-110 (1995).

Eggeling, C. et al., *Highly Sensitive Fluorescence Detection Technology Currently Available for HTS*, Drug Discov. Today 8(14): 632-641 (2003).

Heyduk, T., *Measuring Protein Conformational Changes by FRET/LRET*, Curr. Opin. Biotech. 13(4): 292-296 (2002).

Jameson, D.M., Seifried, S.E., *Quantification of Protein-Protein Interactions Using Fluorescence Polarization*, Methods 19 (2): 222-233 (1999).

Jameson, D. M., Croney, J.C., *Fluorescence Polarization: Past, Present and Future*, Comb. Chem. High Throughput Screen. 6(3): 167-176 (2003).

Kohl, T. et al., *A Protease Assay for Two-Photon Crosscorrelation and FRET Analysis Based Solely on Fluorescent Proteins*, Proc. Natl. Acad. Sci. U.S.A. 99(19): 12161-12166 (2002).

Kristjansdottir, K., Rudolph, J., *A Fluorescence Polarization Assay for Native Protein Substrates of Kinases*, Anal. Biochem. 316(1): 41-49 (2003).

Lakowicz, J.R., *Energy Transfer*, pp. 367-394, in Principles of Fluorescence Spectroscopy, (2d ed. Kluwer Academic/Plenum Publishers, New York 1999).

Lakowicz, J.R. et al., *Novel Fluorescence Sensing Methods for High Throughput Screening*, J. Biomol. Screen. 5(3): 123-131 (2000).

Levine, L M. et al., *Measurement of Specific Protease Activity Utilizing Fluorescence Polarization*, Anal. Biochem. 247(1): 83-88 (1997).

Nikiforov, T.T., Simeonov, A.M., *Application of Fluorescence Polarization to Enzyme Assays and Single Nucleotide Polymorphism Genotyping: Some Recent Developments*, Comb. Chem. High Throughput Screen. 6(3): 201-212 (2003).

Owicki, J.C., *Fluorescence Polarization and Anisotrophy in High Throughput Screening: Perspectives and Primer*, J. Biomol. Screen. 5(5): 297-302 (2000).

Simeonov, A. et al., *Enzyme Assays by Fluorescence Polarization in the Presence of Polyarginine: Study of Kinase, Phosphatase, and Protease Reactions*, Anal. Biochem. 304(2): 193-199 (2002).

Uster, P.S., *In situ Resonance Energy Transfer Microscopy: Monitoring Membrane Fusion in living Cells*, Methods Enzymol. 221: 239-246 (1993).

Weber, G., *Polarization of the Fluorescence of Solutions*, in Fluorescence and Phosphorescence Analysis 217-242 (Wiley Interscience 1966).

* cited by examiner

Figure 1

Assay of BoNT/A 900 kDa Complex

Figure 2

Assay of Pure BoNT/A (150 kDa)

Assay of rLC/A

Figure 4

Assay of BoNT/E Dichain (150 kDa)

Figure 5

Assay of BoNT/A 900 kDa Complex

Figure 6

Assay of Pure BoNT/A (150 kDa)

Figure 7

Assay of BoNT/E Dichain (150 kDa)

Assay of rLC/E

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<221> NAME/KEY: PEPTIDE
<222> LOCATION: (1)...(5)
<223> OTHER INFORMATION: Peptide linker

<400> SEQUENCE: 1

Gly Gly Gly Gly Ser
1               5

<210> SEQ ID NO 2
<211> LENGTH: 5
<212> TYPE: PRT
<213> ORGANISM: Artificial Sequence
<220> FEATURE:
<221> NAME/KEY: PEPTIDE
<222> LOCATION: (1)...(5)
<223> OTHER INFORMATION: Peptide linker

<400> SEQUENCE: 2

Glu Ala Ala Ala Lys
1               5

<210> SEQ ID NO 3
<211> LENGTH: 35
<212> TYPE: DNA
<213> ORGANISM: Artificial Sequence
<220> FEATURE:
<221> NAME/KEY: primer_bind
<222> LOCATION: (1)...(35)
<223> OTHER INFORMATION: PCR oligonucleotide primer

<400> SEQUENCE: 3
gttattgctc agctttagca gtgatggtga tggtg                              35

<210> SEQ ID NO 4
<211> LENGTH: 34
<212> TYPE: DNA
<213> ORGANISM: Artificial Sequence
<220> FEATURE:
<221> NAME/KEY: primer_bind
```

-continued

<222> LOCATION: (1)...(34)
<223> OTHER INFORMATION: PCR oligonucleotide primer

<400> SEQUENCE: 4
gatggtgatg gtgatgacag ccgccaccgc cacc					34

<210> SEQ ID NO 5
<211> LENGTH: 334
<212> TYPE: PRT
<213> ORGANISM: Artificial Sequence
<220> FEATURE:
<221> NAME/KEY: PEPTIDE
<222> LOCATION: (1)...(334)
<223> OTHER INFORMATION: GFP/SNAP-25 fusion protein

<400> SEQUENCE: 5

Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Ile Arg Arg Val Thr Asn
                245                 250                 255

Asp Ala Arg Glu Asn Glu Met Asp Glu Asn Leu Glu Gln Val Ser Gly
            260                 265                 270

Ile Ile Gly Asn Leu Arg His Met Ala Leu Asp Met Gly Asn Glu Ile
        275                 280                 285

Asp Thr Gln Asn Arg Gln Ile Asp Arg Ile Met Glu Lys Ala Asp Ser
290                 295                 300

Asn Lys Thr Arg Ile Asp Glu Ala Asn Gln Arg Ala Thr Lys Met Leu
305                 310                 315                 320

Gly Ser Gly Gly Gly Gly Gly His His His His His His Cys

<210> SEQ ID NO 6
<211> LENGTH: 1131
<212> TYPE: DNA
<213> ORGANISM: Artificial Sequence
<220> FEATURE:
<221> NAME/KEY: mat_peptide
<222> LOCATION: (1)...(1131)
<223> OTHER INFORMATION: Polynucleotide encoding GFP/SNAP-25 fusion protein

<400> SEQUENCE: 6

```
atggctagca aaggagaaga actcttcact ggagttgtcc caattcttgt tgaattagat      60
ggtgatgtta acggccacaa gttctctgtc agtggagagg gtgaaggtga tgcaacatac     120
ggaaaagatg ttaacggcca agttctctct gtcagtggag agggtgaagg tgatgcaaca     180
tacggaaaag atgttaacgg ccacaagttc tctgtcagtg gagagggtga aggtgatgca     240
acatacggaa aacttaccct gaagttcatc tgcactactg gcaaactgcc tgttccatgg     300
ccaacactag tcactactct gtgctatggt gttcaatgct tttcaagata cccggatcat     360
atgaaacggc atgactttt caagagtgcc atgcccgaag ttatgtaca ggaaaggacc       420
atcttcttca agatgacgg caactacaag acacgtgctg aagtcaagtt tgaaggtgat     480
acccttgtta atagaatcga gttaaaaggt attgacttca aggaagatgg caacattctg     540
ggacacaaat tggaatacaa ctataactca cacaatgtat acatcatggc agacaaacaa     600
aagaatggaa tcaaagtgaa cttcaagacc cgccacaaca ttgaagatgg aagcgttcaa     660
ctagcagacc attatcaaca aaatactcca attggcgatg gccctgtcct tttaccagac     720
aaccattacc tgtccacaca atctgccctt tcgaaagatc ccaacgaaaa gagagaccac     780
atggtccttc ttgagtttgt aacagctgct gggattacac atggcatgga tgaactgtac     840
aacgcggtg caggatccgg tgcgggtggc ggtggcatcc ggagggtaac aaacgatgcc     900
cgggaaaatg agatggatga aacctggag caggtgagcg gcatcatcgg aaacctccgc     960
catatggctc tagacatggg caatgagatt gacacccaga tcgccagat cgacaggatc    1020
atggagaagg ctgattccaa caaaaccaga attgatgaag ccaaccaacg tgcaacaaag    1080
atgctgggaa gtggtggcgg tggcggccat caccatcacc atcactgcta a             1131
```

<210> SEQ ID NO 7
<211> LENGTH: 334
<212> TYPE: PRT
<213> ORGANISM: Artificial Sequence
<220> FEATURE:
<221> NAME/KEY: PEPTIDE
<222> LOCATION: (1)...(334)
<223> OTHER INFORMATION: GFP/SNAP-25 fusion protein

<400> SEQUENCE: 7

```
Met Ala Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Cys Tyr Gly Val Gln Cys Phe Ser Arg Tyr Pro Asp His Met Lys
 65                  70                  75                  80
```

```
Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Ile Arg Arg Val Thr Asn
                245                 250                 255

Asp Ala Arg Glu Asn Glu Met Asp Glu Asn Leu Glu Gln Val Ser Gly
            260                 265                 270

Ile Ile Gly Asn Leu Arg His Met Ala Leu Asp Met Gly Asn Glu Ile
        275                 280                 285

Asp Thr Gln Asn Arg Gln Ile Asp Arg Ile Met Glu Lys Ala Asp Ser
    290                 295                 300

Asn Lys Thr Arg Ile Asp Glu Ala Asn Gln Arg Ala Thr Lys Met Leu
305                 310                 315                 320

Gly Ser Gly Gly Gly Gly Cys His His His His His
                325                 330
```

<210> SEQ ID NO 8
<211> LENGTH: 1005
<212> TYPE: DNA
<213> ORGANISM: Artificial Sequence
<220> FEATURE:
<221> NAME/KEY: mat_peptide
<222> LOCATION: (1)...(1005)
<223> OTHER INFORMATION: Polypeptide encoding GFP/SNAP-25 fusion
      protein

<400> SEQUENCE: 8

```
atggctagca aaggagaaga actcttcact ggagttgtcc caattcttgt tgaattagat      60
ggtgatgtta acggccacaa gttctctgtc agtggagagg gtgaaggtga tgcaacatac     120
ggaaaactta ccctgaagtt catctgcact actggcaaac tgcctgttcc atggccaaca     180
ctagtcacta ctctgtgcta tggtgttcaa tgcttttcaa gatacccgga tcatatgaaa     240
cggcatgact ttttcaagag tgccatgccc gaaggttatg tacaggaaag gaccatcttc     300
ttcaaagatg acggcaacta caagacacgt gctgaagtca agtttgaagg tgataccctt     360
gttaatagaa tcgagttaaa aggtattgac ttcaaggaag atggcaacat tctgggacac     420
aaattggaat acaactataa ctcacacaat gtatacatca tggcagacaa acaaaagaat     480
ggaatcaaag tgaacttcaa gacccgccac aacattgaag atggaagcgt tcaactagca     540
gaccattatc aacaaaatac tccaattggc gatggccctg tccttttacc agacaaccat     600
```

-continued

```
tacctgtcca cacaatctgc cctttcgaaa gatcccaacg aaaagagaga ccacatggtc    660
cttcttgagt ttgtaacagc tgctgggatt acacatggca tggatgaact gtacaacggc    720
ggtgcaggat ccggtgcggg tggcggtggc atccggaggg taacaaacga tgcccgggaa    780
aatgagatgg atgagaacct ggagcaggtg agcggcatca tcggaaacct ccgccatatg    840
gctctagaca tgggcaatga gattgacacc cagaatcgcc agatcgacag gatcatggag    900
aaggctgatt ccaacaaaac cagaattgat gaagccaacc aacgtgcaac aaagatgctg    960
ggaagtggtg gcggtggcgg ctgtcatcac catcaccatc actaa                   1005
```

<210> SEQ ID NO 9
<211> LENGTH: 25
<212> TYPE: DNA
<213> ORGANISM: Artificial Sequence
<220> FEATURE:
<221> NAME/KEY: primer_bind
<222> LOCATION: (1)...(25)
<223> OTHER INFORMATION: PCR oligonucleotide primer

<400> SEQUENCE: 9

```
ggtacctttg tatagttcat ccatg                                           25
```

<210> SEQ ID NO 10
<211> LENGTH: 27
<212> TYPE: DNA
<213> ORGANISM: Artificial Sequence
<220> FEATURE:
<221> NAME/KEY: primer_bind
<222> LOCATION: (1)...(27)
<223> OTHER INFORMATION: PCR oligonucleotide primer

<400> SEQUENCE: 10

```
ggtaccgcaa gcaaaggaga agaactc                                         27
```

<210> SEQ ID NO 11
<211> LENGTH: 1722
<212> TYPE: DNA
<213> ORGANISM: Artificial Sequence
<220> FEATURE:
<221> NAME/KEY: mat_peptide
<222> LOCATION: (1)...(1722)
<223> OTHER INFORMATION: Polynucleotide encoding GFP-SNAP-25-IxBFP

<400> SEQUENCE: 11

```
atggctagca aaggagaaga actcttcact ggagttgtcc caattcttgt tgaattagat    60
ggtgatgtta acggccacaa gttctctgtc agtggagagg gtgaaggtga tgcaacatac    120 gaaaactta ccctgaagtt catctgcact actggcaaac tgcctgttcc atggccaaca    180
ctagtcacta ctctgtgcta tggtgttcaa tgcttttcaa gatacccgga tcatatgaaa    240
cggcatgact ttttcaagag tgccatgccc gaaggttatg tacaggaaag gaccatcttc    300
ttcaaagatg acggcaacta caagacacgt gctgaagtca agtttgaagg tgatacccct    360
gttaatagaa tcgagttaaa aggtattgac ttcaaggaag atggcaacat tctgggacac    420
aaattggaat acaactataa ctcacacaat gtatacatca tggcagacaa acaaaagaat    480
ggaatcaaag tgaacttcaa gacccgccac aacattgaag atggaagcgt tcaactagca    540
gaccattatc aacaaaatac tccaattggc gatggccctg tccttttacc agacaaccat    600
tacctgtcca cacaatctgc cctttcgaaa gatcccaacg aaaagagaga ccacatggtc    660
cttcttgagt ttgtaacagc tgctgggatt acacatggca tggatgaact gtacaacggc    720
ggtgcaggat ccggtgcggg tggcggtggc atccggaggg taacaaacga tgcccgggaa    780
```

```
aatgagatgg atgagaacct ggagcaggtg agcggcatca tcggaaacct ccgccatatg    840
gctctagaca tgggcaatga gattgacacc cagaatcgcc agatcgacag gatcatggag    900
aaggctgatt ccaacaaaac cagaattgat gaagccaacc aacgtgcaac aaagatgctg    960
ggaagtggtg gcggtggcgg taccgcaagc aaaggagaag aactcttcac tggagttgtc   1020
ccaattcttg ttgaattaga tggtgatgtt aacggccaca gttctctgt cagtggagag   1080 ggtgaaggtg atgcaacata cggaaaactt accctgaagt tcatctgcac tactggcaaa   1140
ctgcctgttc catggccaac actagtcact actctctctc atggtgttca atgcttttca   1200
agatacccgg atcatatgaa acggcatgac ttttttcaaga gtgccatgcc cgaaggttat   1260
gtacaggaaa ggaccatctt cttcaaagat gacggcaact acaagacacg tgctgaagtc   1320
aagtttgaag gtgataccct tgttaataga atcgagttaa aaggtattga ttttaaagaa   1380
gatggaaaca ttcttggaca caaattggaa tacaactata actcacacaa tgtatacatc   1440
atggcagaca acaaaagaa tggaatcaaa gcgaacttca gatccgcca acacattgaa   1500 gatggaagcg ttcaactagc agaccattat caacaaaata ctccaattgg cgatggccct   1560 gtcctttac cagacaacca ttacctgtcc acacaatctg cccttttcgaa agatcccaac   1620 gaaaagagag accacatggt ccttcttgag tttgtaacag ctgctgggat tacacatggc   1680
atggatgaac tatacaaagg tacccatcac catcaccatc ac                      1722
```

<210> SEQ ID NO 12
<211> LENGTH: 574
<212> TYPE: PRT
<213> ORGANISM: Artificial Sequence
<220> FEATURE:
<221> NAME/KEY: PEPTIDE
<222> LOCATION: (1)...(574)
<223> OTHER INFORMATION: GFP-SNAP-25-IxBFP

<400> SEQUENCE: 12

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
           100                 105                 110

Val Lys Phe Glu Gly Asp Thr Leu Val Asn Arg Ile Glu Leu Lys Gly
       115                 120                 125

Ile Asp Phe Lys Glu Asp Gly Asn Ile Leu Gly His Lys Leu Glu Tyr
   130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
               165                  170                 175

Val Gln Leu Ala Asp His Tyr Gln Gln Asn Thr Pro Ile Gly Asp Gly
           180                 185                 190
```

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Glu Phe
210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Ile Arg Arg Val Thr Asn
                245                 250                 255

Asp Ala Arg Glu Asn Glu Met Asp Glu Asn Leu Glu Gln Val Ser Gly
                260                 265                 270

Ile Ile Gly Asn Leu Arg His Met Ala Leu Asp Met Gly Asn Glu Ile
            275                 280                 285

Asp Thr Gln Asn Arg Gln Ile Asp Arg Ile Met Glu Lys Ala Asp Ser
            290                 295                 300

Asn Lys Thr Arg Ile Asp Glu Ala Asn Gln Arg Ala Thr Lys Met Leu
305                 310                 315                 320

Gly Ser Gly Gly Gly Gly Thr Ala Ser Lys Gly Glu Glu Leu Phe
                325                 330                 335

Thr Gly Val Val Pro Ile Leu Val Glu Leu Asp Gly Asp Val Asn Gly
                340                 345                 350

His Lys Phe Ser Val Ser Gly Glu Gly Glu Gly Asp Ala Thr Tyr Gly
            355                 360                 365

Lys Leu Thr Leu Lys Phe Ile Cys Thr Thr Gly Lys Leu Pro Val Pro
        370                 375                 380

Trp Pro Thr Leu Val Thr Thr Leu Ser His Gly Val Gln Cys Phe Ser
385                 390                 395                 400

Arg Tyr Pro Asp His Met Lys Arg His Asp Phe Phe Lys Ser Ala Met
                405                 410                 415

Pro Glu Gly Tyr Val Gln Glu Arg Thr Ile Phe Phe Lys Asp Asp Gly
                420                 425                 430

Asn Tyr Lys Thr Arg Ala Glu Val Lys Phe Glu Gly Asp Thr Leu Val
            435                 440                 445

Asn Arg Ile Glu Leu Lys Gly Ile Asp Phe Lys Glu Asp Gly Asn Ile
450                 455                 460

Leu Gly His Lys Leu Glu Tyr Asn Tyr Asn Ser His Asn Val Tyr Ile
465                 470                 475                 480

Met Ala Asp Lys Gln Lys Asn Gly Ile Lys Ala Asn Phe Lys Ile Arg
                485                 490                 495

His Asn Ile Glu Asp Gly Ser Val Gln Leu Ala Asp His Tyr Gln Gln
                500                 505                 510

Asn Thr Pro Ile Gly Asp Gly Pro Val Leu Leu Pro Asp Asn His Tyr
            515                 520                 525

Leu Ser Thr Gln Ser Ala Leu Ser Lys Asp Pro Asn Glu Lys Arg Asp
530                 535                 540

His Met Val Leu Leu Glu Phe Val Thr Ala Ala Gly Ile Thr His Gly
545                 550                 555                 560

Met Asp Glu Leu Tyr Lys Gly Thr His His His His His
                565                 570

<210> SEQ ID NO 13
<211> LENGTH: 2442
<212> TYPE: DNA
<213> ORGANISM: Artificial Sequence
<220> FEATURE:
<221> NAME/KEY: mat_peptide
<222> LOCATION: (1)...(2442)
<223> OTHER INFORMATION: Polynucleotide encoding GFP-SNAP-25-2xBFP

<400> SEQUENCE: 13

```
atggctagca aaggagaaga actcttcact ggagttgtcc caattcttgt tgaattagat      60
ggtgatgtta acggccacaa gttctctgtc agtggagagg gtgaaggtga tgcaacatac     120
ggaaaactta ccctgaagtt catctgcact actggcaaac tgcctgttcc atggccaaca     180
ctagtcacta ctctgtgcta tggtgttcaa tgcttttcaa gatacccgga tcatatgaaa     240
cggcatgact ttttcaagag tgccatgccc gaaggttatg tacaggaaag gaccatcttc     300
ttcaaagatg acggcaacta caagacacgt gctgaagtca agtttgaagg tgataccctt     360
gttaatagaa tcgagttaaa aggtattgac ttcaaggaag atggcaacat tctgggacac     420
aaattggaat acaactataa ctcacacaat gtatacatca tggcagacaa acaaaagaat     480
ggaatcaaag tgaacttcaa gacccgccac aacattgaag atggaagcgt tcaactagca     540
gaccattatc aacaaaatac tccaattggc gatggccctg tccttttacc agacaaccat     600
tacctgtcca cacaatctgc cctttcgaaa gatcccaacg aaaagagaga ccacatggtc     660
cttcttgagt ttgtaacagc tgctgggatt acacatggca tggatgaact gtacaacggc     720
ggtgcaggat ccggtgcggg tggcggtggc atccggaggg taacaaacga tgcccgggaa     780
aatgagatgg atgagaacct ggagcaggtg agcggcatca tcggaaaccct ccgccatatg     840
gctctagaca tggcaatga gattgacacc cagaatcgcc agatcgacag gatcatggag     900
aaggctgatt ccaacaaaac cagaattgat gaagccaacc aacgtgcaac aaagatgctg     960
ggaagtggtg gcggtggcgg taccgcaagc aaaggagaag aactcttcac tggagttgtc    1020
ccaattcttg ttgaattaga tggtgatgtt aacggccaca gttctctgt cagtggagag    1080
ggtgaaggtg atgcaacata cggaaaactt accctgaagt tcatctgcac tactggcaaa    1140
ctgcctgttc catggccaac actagtcact actctctctc atggtgttca atgcttttca    1200
agatacccgg atcatatgaa acggcatgac ttttcaaga gtgccatgcc cgaaggttat    1260
gtacaggaaa ggaccatctt cttcaaagat gacggcaact acaagacacg tgctgaagtc    1320
aagtttgaag gtgataccct tgttaataga atcgagttaa aaggtattga ttttaaagaa    1380
gatggaaaca ttcttggaca caaattggaa tacaactata actcacacaa tgtatacatc    1440
atggcagaca acaaaagaa tggaatcaaa gcgaacttca agatccgcca acattgaa    1500
gatggaagcg ttcaactagc agaccattat caacaaaata ctccaattgg cgatggccct    1560
gtccttttac cagacaacca ttacctgtcc acacaatctg cccttcgaa agatcccaac    1620
gaaaagagag accacatggt ccttcttgag tttgtaacag ctgctgggat tacacatggc    1680
atggatgaac tatacaaagg taccgcaagc aaaggagaag aactcttcac tggagttgtc    1740
ccaattcttg ttgaattaga tggtgatgtt aacggccaca gttctctgt cagtggagag    1800
ggtgaaggtg atgcaacata cggaaaactt accctgaagt tcatctgcac tactggcaaa    1860
ctgcctgttc catggccaac actagtcact actctctctc atggtgttca atgcttttca    1920
agatacccgg atcatatgaa acggcatgac ttttcaaga gtgccatgcc cgaaggttat    1980
gtacaggaaa ggaccatctt cttcaaagat gacggcaact acaagacacg tgctgaagtc    2040
aagtttgaag gtgataccct tgttaataga atcgagttaa aaggtattga ttttaaagaa    2100
gatggaaaca ttcttggaca caaattggaa tacaactata actcacacaa tgtatacatc    2160
atggcagaca acaaaagaa tggaatcaaa gcgaacttca agatccgcca acattgaa    2220
gatggaagcg ttcaactagc agaccattat caacaaaata ctccaattgg cgatggccct    2280
```

```
gtcctttac cagacaacca ttacctgtcc acacaatctg cccttcgaa agatcccaac    2340 gaaagagag accacatggt ccttcttgag tttgtaacag ctgctgggat tacacatggc   2400
atggatgaac tatacaaagg tacccatcac catcaccatc ac                     2442
```

<210> SEQ ID NO 14
<211> LENGTH: 814
<212> TYPE: PRT
<213> ORGANISM: Artificial Sequence
<220> FEATURE:
<221> NAME/KEY: PEPTIDE
<222> LOCATION: (1)...(814)
<223> OTHER INFORMATION: GFP-SNAP-25-2xBFP

<400> SEQUENCE: 14

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Ile Arg Arg Val Thr Asn
                245                 250                 255

Asp Ala Arg Glu Asn Glu Met Asp Glu Asn Leu Glu Gln Val Ser Gly
            260                 265                 270

Ile Ile Gly Asn Leu Arg His Met Ala Leu Asp Met Gly Asn Glu Ile
        275                 280                 285

Asp Thr Gln Asn Arg Gln Ile Asp Arg Ile Met Glu Lys Ala Asp Ser
    290                 295                 300

Asn Lys Thr Arg Ile Asp Glu Ala Asn Gln Arg Ala Thr Lys Met Leu
305                 310                 315                 320

Gly Ser Gly Gly Gly Gly Gly Thr Ala Ser Lys Gly Glu Glu Leu Phe
```

```
                    325                 330                 335
Thr Gly Val Val Pro Ile Leu Val Glu Leu Asp Gly Asp Val Asn Gly
                340                 345                 350
His Lys Phe Ser Val Ser Gly Glu Gly Glu Gly Asp Ala Thr Tyr Gly
                355                 360                 365
Lys Leu Thr Leu Lys Phe Ile Cys Thr Thr Gly Lys Leu Pro Val Pro
            370                 375                 380
Trp Pro Thr Leu Val Thr Thr Leu Ser His Gly Val Gln Cys Phe Ser
385                 390                 395                 400
Arg Tyr Pro Asp His Met Lys Arg His Asp Phe Phe Lys Ser Ala Met
                405                 410                 415
Pro Glu Gly Tyr Val Gln Glu Arg Thr Ile Phe Phe Lys Asp Asp Gly
                420                 425                 430
Asn Tyr Lys Thr Arg Ala Glu Val Lys Phe Glu Gly Asp Thr Leu Val
                435                 440                 445
Asn Arg Ile Glu Leu Lys Gly Ile Asp Phe Lys Glu Asp Gly Asn Ile
            450                 455                 460
Leu Gly His Lys Leu Glu Tyr Asn Tyr Asn Ser His Asn Val Tyr Ile
465                 470                 475                 480
Met Ala Asp Lys Gln Lys Asn Gly Ile Lys Ala Asn Phe Lys Ile Arg
                485                 490                 495
His Asn Ile Glu Asp Gly Ser Val Gln Leu Ala Asp His Tyr Gln Gln
                500                 505                 510
Asn Thr Pro Ile Gly Asp Gly Pro Val Leu Leu Pro Asp Asn His Tyr
                515                 520                 525
Leu Ser Thr Gln Ser Ala Leu Ser Lys Asp Pro Asn Glu Lys Arg Asp
            530                 535                 540
His Met Val Leu Leu Glu Phe Val Thr Ala Ala Gly Ile Thr His Gly
545                 550                 555                 560
Met Asp Glu Leu Tyr Lys Gly Thr Ala Ser Lys Gly Glu Glu Leu Phe
                565                 570                 575
Thr Gly Val Val Pro Ile Leu Val Glu Leu Asp Gly Asp Val Asn Gly
                580                 585                 590
His Lys Phe Ser Val Ser Gly Glu Gly Glu Gly Asp Ala Thr Tyr Gly
                595                 600                 605
Lys Leu Thr Leu Lys Phe Ile Cys Thr Thr Gly Lys Leu Pro Val Pro
            610                 615                 620
Trp Pro Thr Leu Val Thr Thr Leu Ser His Gly Val Gln Cys Phe Ser
625                 630                 635                 640
Arg Tyr Pro Asp His Met Lys Arg His Asp Phe Phe Lys Ser Ala Met
                645                 650                 655
Pro Glu Gly Tyr Val Gln Glu Arg Thr Ile Phe Phe Lys Asp Asp Gly
                660                 665                 670
Asn Tyr Lys Thr Arg Ala Glu Val Lys Phe Glu Gly Asp Thr Leu Val
                675                 680                 685
Asn Arg Ile Glu Leu Lys Gly Ile Asp Phe Lys Glu Asp Gly Asn Ile
            690                 695                 700
Leu Gly His Lys Leu Glu Tyr Asn Tyr Asn Ser His Asn Val Tyr Ile
705                 710                 715                 720
Met Ala Asp Lys Gln Lys Asn Gly Ile Lys Ala Asn Phe Lys Ile Arg
                725                 730                 735
His Asn Ile Glu Asp Gly Ser Val Gln Leu Ala Asp His Tyr Gln Gln
                740                 745                 750
```

```
Asn Thr Pro Ile Gly Asp Gly Pro Val Leu Leu Pro Asp Asn His Tyr
            755                 760                 765

Leu Ser Thr Gln Ser Ala Leu Ser Lys Asp Pro Asn Glu Lys Arg Asp
        770                 775                 780

His Met Val Leu Leu Glu Phe Val Thr Ala Ala Gly Ile Thr His Gly
785                 790                 795                 800

Met Asp Glu Leu Tyr Lys Gly Thr His His His His His
                805                 810

<210> SEQ ID NO 15
<211> LENGTH: 8
<212> TYPE: PRT
<213> ORGANISM: Artificial Sequence
<220> FEATURE:
<221> NAME/KEY: DOMAIN
<222> LOCATION: (1)...(8)
<223> OTHER INFORMATION: PKA RII phosphorylation recognition motif

<400> SEQUENCE: 15

Asp Ser Glu Ser Glu Glu Glu Asp
1               5

<210> SEQ ID NO 16
<211> LENGTH: 400
<212> TYPE: PRT
<213> ORGANISM: Bos taurus

<400> SEQUENCE: 16

Ser His Ile Gln Ile Pro Pro Gly Leu Thr Glu Leu Leu Gln Gly Tyr
1               5                   10                  15

Thr Val Glu Val Leu Arg Gln Arg Pro Pro Asp Leu Val Asp Phe Ala
            20                  25                  30

Val Asp Tyr Phe Thr Arg Leu Arg Glu Ala Arg Ser Arg Ala Ser Thr
        35                  40                  45

Pro Pro Ala Ala Pro Pro Ser Gly Ser Gln Asp Phe Asp Pro Gly Ala
    50                  55                  60

Gly Leu Val Ala Asp Ala Val Ala Asp Ser Glu Ser Glu Asp Glu Glu
65                  70                  75                  80

Asp Leu Asp Val Pro Ile Pro Gly Arg Phe Asp Arg Arg Val Ser Val
                85                  90                  95

Cys Ala Glu Thr Tyr Asn Pro Asp Glu Glu Glu Asp Thr Asp Pro
            100                 105                 110

Arg Val Ile His Pro Lys Thr Asp Gln Gln Arg Cys Arg Leu Gln Glu
            115                 120                 125

Ala Cys Lys Asp Ile Leu Leu Phe Lys Asn Leu Asp Pro Glu Gln Leu
    130                 135                 140

Ser Gln Val Leu Asp Ala Met Phe Glu Arg Thr Val Lys Val Asp Glu
145                 150                 155                 160

His Val Ile Asp Gln Gly Asp Asp Gly Asp Asn Phe Tyr Val Ile Glu
                165                 170                 175

Arg Gly Thr Tyr Asp Ile Leu Val Thr Lys Asp Asn Gln Thr Arg Ser
            180                 185                 190

Val Gly Gln Tyr Asp Asn His Gly Ser Phe Gly Glu Leu Ala Leu Met
        195                 200                 205

Tyr Asn Thr Pro Arg Ala Ala Thr Ile Val Ala Thr Ser Glu Gly Ser
    210                 215                 220

Leu Trp Gly Leu Asp Arg Val Thr Phe Arg Arg Ile Ile Val Lys Asn
225                 230                 235                 240
```

-continued

```
Asn Ala Lys Lys Arg Lys Met Phe Glu Ser Phe Ile Glu Ser Val Pro
            245                 250                 255

Leu Leu Lys Ser Leu Glu Val Ser Glu Arg Met Lys Ile Val Asp Val
            260                 265                 270

Ile Gly Glu Lys Val Tyr Lys Asp Gly Glu Arg Ile Ile Thr Gln Gly
            275                 280                 285

Glu Lys Ala Asp Ser Phe Tyr Ile Ile Glu Ser Gly Glu Val Ser Ile
            290                 295                 300

Leu Ile Lys Ser Lys Thr Lys Val Asn Lys Asp Gly Glu Asn Gln Glu
305                 310                 315                 320

Val Glu Ile Ala Arg Cys His Lys Gly Gln Tyr Phe Gly Glu Leu Ala
                325                 330                 335

Leu Val Thr Asn Lys Pro Arg Ala Ala Ser Ala Tyr Ala Val Gly Asp
                340                 345                 350

Val Lys Cys Leu Val Met Asp Val Gln Ala Phe Glu Arg Leu Leu Gly
            355                 360                 365

Pro Cys Met Asp Ile Met Lys Arg Asn Ile Ser His Tyr Glu Glu Gln
    370                 375                 380

Leu Val Lys Met Phe Gly Ser Ser Met Asp Leu Ile Asp Pro Gly Gln
385                 390                 395                 400
```

<210> SEQ ID NO 17
<211> LENGTH: 18
<212> TYPE: DNA
<213> ORGANISM: Artificial Sequence
<220> FEATURE:
<221> NAME/KEY: primer_bind
<222> LOCATION: (1)...(18)
<223> OTHER INFORMATION: Polynucleotide probe

<400> SEQUENCE: 17
ttctcctttg ctagccat                                                  18

ASSAYS OF MOLECULAR OR SUBCELLULAR INTERACTIVITY USING DEPOLARIZATION AFTER RESONANCE TRANSFER ENERGY (DARET)

This application claims priority pursuant to 35 U.S.C. §119(e) to U.S. Provisional Application 60/726,515, filed Oct. 12, 2005, which is hereby incorporated by reference herein in its entirety.

The present invention relates generally to assays for detecting the physical interaction (or lack of physical interaction) between or among molecules or parts of the same molecule. Additionally, the present assay is applicable to detecting interactions between, e.g., subcellular features such as, without limitation, the plasma membrane, mitochondria, Golgi apparatus, vesicles, and the like using novel optical technique called Depolarization After Resonance Transfer Energy (DARET).

Such assays can be very useful in applications including the measurement or detection of ligand:receptor interactions, certain enzymes assays (such as protease assays), the detection of intracellular molecular trafficking, and in the detection of protein:protein, nucleic acid:nucleic acid, and protein:nucleic acid interactions.

The location of molecules within a cell may suggest something concerning their function. Proteins that travel from the cytoplasm to the nucleus when the cell is exposed to a hormone or growth factor may be involved in gene expression. Alternatively, molecules that are transported to the cell membrane in response to a stimulus may be secretory molecules involved in cell-cell signaling for example, neurotransmitters produced within neurons are stored for later use before responding to a transient change in membrane potential by being secreted into the synaptic cleft. It is useful to monitor the location of such molecules with respect to cellular features such as, for example, the Golgi apparatus, the cell membrane, and lysosymes.

Moreover, assays for the detection of interactivity between molecules may have clear applicability to drug discovery efforts. For example, the construction of compound libraries containing hundreds of thousands of compounds or more has now become rather commonplace; however the ability to screen such large compound libraries is a common bottleneck to developing a drug. The present methods provide easy and rapid assays of, for example, drug binding and/or activity, which can be conducted in real time, without the use of radioactive or toxic reagents. The present methods are also adaptable for use in high throughput screening formats, permitting automation of various steps of the assay.

The construction and screening of large libraries of compounds is a relatively recent practical advance in drug development, having coincided with the development of precise molecular cloning and genetic engineering techniques that permit the construction of cloned target molecules, particularly proteins. The proteins are usually the result of genetic manipulation, often as the result of expression from a vector construct introduced into a host cell. The target molecules can be partially purified and are sometimes used in an entirely in vitro assay system. Alternatively, sometimes the host cell expressing the target molecule is used in culture as part of the assay system.

Prior to the advent of high throughput screening, drug-screening assays were often the result of academic research developed with an emphasis upon basic biological research rather than high volume. These assays were often time and labor-intensive, and typically involved the use of radionuclides, with the attendant risks to the health of laboratory personnel associated therewith. Hence, the assay systems used as the basis for the first rationally designed drug discovery efforts were derivatives of these assays, and became a rate-limiting step in the rapid identification of potentially useful compounds for a given therapeutic application.

Typically, assay methods have been based upon so-called heterogeneous assay methods. In most assays the assay results in a mixture of unreacted or unbound compounds (such as, without limitation, an enzyme substrate or receptor ligand) and reacted or bound components, (for example an enzyme product or receptor-bound ligand). Often one or more of these components is labeled with a detectable label. In a "heterogeneous assay" this mixture is (and generally must be) resolved by physical separation of the reacted, modified, or bound labeled material from the remaining label before useful data can be obtained. For example, if the assay is a binding assay, linkage of the receptor to be bound by a ligand to a solid support, such as magnetic beads, permits washing of the beads following reaction. The label associated with the washed beads can then be detected as an indication of the desired interaction or activity.

By contrast, assay methods in which detection of the reacted, modified, or bound labeled material can be made without the need for a separation step is termed a "homogeneous" assay system. An illustration of a homogeneous nucleic acid detection system can be found in, e.g., U.S. Pat. No. 5,639,604 entitled "Homogeneous Protection Assay".

This and all other publications cited in this patent application are hereby incorporated by reference as part of the present patent application unless expressly stated otherwise.

More recently, particularly following the development of precisely engineered fusion proteins incorporating fluorescent moieties such as green fluorescent protein (GFP) and its derivatives of other colors, the use of fluorescence has become an increasingly popular choice in life science research and development. Fluorophores may be smaller organic molecules such as fluorescent dyes or larger molecules such as fluorescent polypeptides. While not all fluorescence methods are amenable to high-throughput screening, a number of methods have been described in the literature. For example, Eggeling et al., 8:632 *Drug Discovery Today* (July 2003) describe techniques including total fluorescence, time gated fluorescence, fluorescence polarization, fluorescence lifetime, or time-resolved anisotropy, which are amenable to high throughput screening.

Total fluorescence is often used to detect enzyme activity in assays designed in such a manner that the substrate (or product) becomes fluorescent (or fluorescence is quenched) upon enzymatic modification of the substrate. For the purposes of this patent application, the term "fluorescence" means the emission of electromagnetic radiation, especially of visible light, stimulated in a substance by the absorption of incident radiation, and specifically includes luminescence. Time-gated fluorescence employs fluorophores having long fluorescence lifetimes (such as the lanthamide chelates) to distinguish their fluorescence from shorter-lived fluorescence. This has reportedly been used in combination with fluorescence resonance energy transfer (FRET), which involves the non-radiative transfer of energy from a donor to an acceptor molecule. Fluorescence polarization is a technique that involves the detection of changes in polarization that arise from differences in the molar volume of reactants and products.

Additionally, the use of devices such as high-energy lasers for excitation and confocal microscopy has permitted the excitation and detection of emitted light to be much more easily controlled today than ever before. For example, while not solely or strictly a high throughput method, a protease assay has been recently described that utilizes GFP and the red fluorescent protein DsRed in a way that permits both FRET and dual color cross correlation analysis (an ultra low volume single-molecule method that selectively probes the concomitant movement of two distinguishable probes). In this homogeneous assay, a protease substrate is labeled with the two fluorescent labels and proteolytic cleavage of a substrate containing the two fluorescent protein domains is detected when the dual-labeled substrate is separated into two single labeled substrates. Cleavage not only disrupts joint fluctuations in the two detection channels, but also results in the termination of FRET between the labels. See Kohl et al., *Proc. Nat'l. Acad. Sci.* 99: 12161 (Sep. 17, 2002).

As mentioned above, fluorescence polarization has traditionally been used to derive information concerning the size and/or shape of molecules. Fluorescence polarization is a phenomenon that occurs when a fluorescent molecule is excited by plane-polarized light of a given wavelength such that it undergoes a transition to a higher energy excited state, called the $S_1$ state. Such a molecule then emits light of lower energy (and thus longer wavelength) when it returns to its unexcited ground state ($S_0$). The average time a fluorophore (or more accurately, a population of identical fluorophores) spends in the excited state before returning to the ground state through fluorescent light emission is called "fluorescence lifetime", and is specific to each compound. If the molecule is in liquid solution, Brownian motion (sometimes called Brownian rotation) may cause a change in orientation of the fluorescent molecule between the time of excitation and the time of fluorescence emission. A fluorophore inherently has a dipole moment with a defined orientation along which it vibrates when excited, and along which it emits a photon when it returns to its ground state. When in solution, the orientation of this dipole moment may change as the molecule rotates, so that the orientation of the light subsequently emitted by the molecule will be randomized to some extent. The movement of the dipole moment depends upon a number of factors.

Some of these factors are related to the ability of the excited molecule to rotate. The viscosity of the solution is one such factor. The more viscous the solution in which the fluorescent molecule is contained, the more constrained each molecule is from changing its orientation and the less likely that the emitted fluorescence will be polarized with respect to the angle of the plane depolarized excitation light.

Similarly, a substantially round globular molecule will be freer to rotate around any axis than a long filamentous molecule would be to rotate end over end, and a bulky, massive molecule has greater inertia (and thus resistance to rotation) than a smaller, less bulky molecule. Thus in this situation, with all other things being equal, the smaller molecule is more likely to show fluorescent depolarization than the larger, more bulky molecule.

Under certain conditions an additional phenomenon, sometimes called energy migration, is seen with fluorescent molecules in solution. In concentrated solutions, as the concentration of fluorescent molecules increases so does the possibility of the transfer of the energy between these molecules, for example, from an excited first $S_1$ molecule to an unexcited $S_0$ second molecule having a similar but not necessarily perfectly parallel orientation to the first. The transfer of the higher energy states from the first molecule to the second causes the first molecule to return to the $S_0$ ground state and the first molecule to transition to a higher energy state. In this way the orientation of the emitting fluorophore may bear little relationship to the one originally excited. See e.g., Weber, G., *Polarization of the Fluorescence of Solutions*, in FLUORESCENCE AND PHOSPHORESCENCE ANALYSIS 217, 229 (Chapter 8 Wiley Interscience 1966), hereby incorporated by reference herein. Thus, there is fluorescence depolarization observed even in very viscous solutions (where the ability of the molecule to rotate is severely restricted) if the concentration of fluorescent molecules is high enough to permit resonance energy transfer. See id.

Recently the advantages of fluorescence polarization have led an increasing number of researchers to investigate using this phenomenon as an indication of enzyme or other biological or biochemical activity. Thus, Simeonov et al., 304 *Anal. Biochem.* 193 (2002) have described the use of fluorescence polarization in solutions containing polyarginine for the detection of kinase, phosphatase, and protease activity. Scott and Carpenter, 316 *Anal. Biochem.* 82 (2003) have described the use of fluorescence polarization in the presence of zinc salts for the detection of phosphopeptides in assays of kinase activity. Kristjansdottir and Rudolph, 316 *Anal. Biochem.* 41 (2003) describe a fluorescence polarization assay for the detection of the native protein substrates of kinases. Sugden et al., U.S. Pat. No. 6,110,750 describe a method for the detection of *Mycobacterium bovis* by fluorescence polarization.

Advantages of fluorescence polarization assays include the fact that they are homogeneous—they do not require a separation step and do not require attachment of substrate to an immobilized phase. Furthermore, polarization values can be measured repeatedly, with no consumption of sample or substrate necessary. In addition, fluorescence polarization is a sensitive technique that can be used to measure polarization values of fluorophores from low picomolar and micromolar levels even to the attomolar range. Polarization is also independent of fluorescence intensity.

In particular, fluorescence polarization (P) and anisotropy (r) are defined as follows:

$$\text{Polarization} = P = \frac{I_{Vertical} - I_{Horizontal}}{I_{Vertical} + I_{Horizontal}}$$

and $$\text{Anisotrophy} = r = \frac{I_{Vertical} - I_{Horizontal}}{I_{Vertical} + 2 \cdot I_{Horizontal}}$$

where $I_{Vertical}$ is the intensity of the emission light parallel to the excitation light plane and $I_{Horizontal}$ is the intensity of the emission light perpendicular to the excitation light plane. P and r, being ratios of light intensities, are dimensionless. Experimental data can be expressed in millipolarization units (mP), where 1 polarization unit=1000 mP units, or in millianisotropy units (mA), where 1 anisotropy unit=1000 mA units.

In the context of fluorescence polarization, polarization can be expressed in part as the relationship involving fluorescence lifetime and how fast a fluorophore rotates in the time between excitation and emission. The principal factors controlling rotation are molar volume (V), absolute temperature (T), and viscosity (η). The rotational correlation time (θ) and the rotational relaxation time ($\rho_o$) are taken from the work of Perrin and Weber. In particular, the rotational correlation time (θ) is taken from the Perrin equation as follows:

$$\left(\frac{1}{P} - \frac{1}{3}\right) = \left(\frac{1}{P_o} - \frac{1}{3}\right) \cdot (1 + \tau/\theta)$$

and is defined as: Rotational Correlation Time $$(\theta) = \frac{\eta V}{RT}$$

Furthermore, the rotational relaxation time ($\rho_o$) is taken from the Perrin/Weber equation, as follows:

$$\left(\frac{1}{\rho} - \frac{1}{3}\right) = \left(\frac{1}{\rho_o} - \frac{1}{3}\right) * (1 + 3\tau/\rho)$$

and is defined as: Rotational Relaxation Time, where R is the gas constant, $\tau$ is the fluorescence lifetime, $\rho$ is the polarization, and $\rho_0$ is the limiting polarization.

$$(\rho_o) = \frac{3\eta V}{RT}$$

From the above, it can be seen that, where lifetime, viscosity, and temperature are held constant, the molecular volume (and thus the polarization or anisotropy) determines the rotation. The larger the molecular volume, the slower the molecule rotates and the higher the polarization and anisotropy values. Furthermore, as is evident from the equations above, the rotational relaxation time will be exactly three times longer than the rotational correlation time.

Likewise FRET (fluorescence resonance energy transfer) is a phenomenon that has already been widely exploited in the assay of molecules and molecular interactions. Fluorescent energy transfer requires a "donor" fluorophore that absorbs light energy of a given wavelength, and an "acceptor" fluorophore that receives resonant energy without the emission of light from the oscillation of the excited donor molecule. Once such energy is transferred, the donor molecule returns to its ground state and the acceptor molecule becomes excited, and subsequently releases a photon of light permitting it to return to its ground state.

Because FRET requires the transfer of energy from a donor molecule to an acceptor molecule, the FRET phenomenon is distance-dependent; the efficiency of FRET is dependent on the inverse sixth power of the intermolecular separation, making it useful over distances comparable to the dimensions of biological macromolecules. This means that the dye molecules must be separated by no more than about 5 Angstroms, or about 10 Angstroms to about 100 Angstroms, or preferably from no more than about 20 to about 100 Angstroms, or about 50 to about 100 Angstroms or about 50 to about 80 Angstroms. It is also important in the choice of appropriate donor/acceptor fluorophore pairs that the absorption spectrum of the acceptor overlaps the fluorescence emission spectrum of the donor. Finally, the transition dipole moments of the donor and acceptor should be approximately parallel. See e.g., Invitrogen Web site, and search under probes.invitrogen.com/handbook/.

A multitude of suppliers of biochemical research reagents and research tools offer products for sale that utilize FRET as a method for detecting the proximity of molecular and/or cellular features to each other. For example, the use of FRET is well established in certain signal transduction, protein trafficking, gene expression, and protease assays.

Despite the use of FRET and the fluorescent proteins in conjunction therewith, there is a need for additional and different rapid homogenous assays in applications including high throughput screening, quality control and assurance assays, and as a basic scientific tool to detect molecular proximity. Preferably such methods would be capable of being monitored in real time.

Patent application Ser. No. 10/948,097 entitled "Fluorescent Polarization Assays for Determining Clostridial Toxin Activity", filed Sep. 22, 2004, has common inventors and the same assignee as the present application. The cited application is drawn, among other things, the use of DARET for the detection and measurement of protease activity, in particular neurotoxin activity derived from, e.g., *Clostridium botulinum* and *Clostridium tetani*.

The present invention is directed to a novel method for detecting and/or measuring differences in the distance between two or more molecular features. The method, given the name Depolarization After Resonance Energy Transfer (DARET), relies on the detection of changes in the polarization state of light absorbed by one fluorophore and emitted by a second fluorophore in labeled analytes.

As indicated above, fluorescence is the light emitted by an atom or molecule after a finite duration subsequent to the absorption of electromagnetic energy. Specifically, the emitted light arises from the transition of the excited species from its first excited electronic singlet level to its ground electronic level.

In standard fluorescence-based detection, a fluorophore will only be able to absorb the exciting light if its absorption dipole moments (which have a fixed direction on the molecular framework of the fluorophore) are approximately aligned with the electric vector of the illumination. This process is termed photoselection. The principle of operation of a fluorescence-based method is simply to measure the amount of photons emitted from the fluorophore after excitation, a term called fluorescence intensity.

Methods using standard fluorescence-based detection include, e.g., traditional fluorescence and Fluorescence Resonance Energy Transfer (FRET). In traditional fluorescence, a light directly excites the fluorophore, which emits light as it returns to ground state. In FRET, excitation of the acceptor fluorophore occurs when the excited state energy of a donor fluorophore is transferred to the acceptor by intermolecular long-range dipole-dipole coupling. In FRET, the efficiency of energy transfer depends on the extent of spectral overlap of the donor emission spectrum and the acceptor absorption spectrum as well as the distance between the donor and acceptor molecules and the relative orientation of the emission dipole of the donor and the absorption dipole of the acceptor. The light emitted by the acceptor fluorophore has less energy than the light absorbed (or emitted) by the donor fluorophore, and thus has a different wavelength than light emitted by the donor alone.

In fluorescence polarization-based detection (FP), the exciting light is polarized, meaning the direction of the light's electric vector has a unique planar direction. The polarization of light emitted by a population of fluorophores will depend upon the degree of rotation each fluorophore from that population experiences during its excited state lifetime. The only fluorophores that are excited by the polarized light will be those fluorophores whose absorption dipole moments are approximately aligned with this polarized light. As such, FP does not detect fluorescence intensity, but instead determines the extent of fluorophore rotation between excitation and emission.

As a general principle, the greater the volume occupied by a molecule, or the more viscous the solvent, the more slowly that molecule will rotate before the excited fluorophore emits light. Hence, when the fluorophore is rotating slowly, relative to its excited state lifetime, there is a greater chance that the emitted light will have its electric vector still approximately aligned with the direction of the polarized excitation and, thus, the polarization of this emission will be high. Conversely, the smaller the volume occupied by a molecule, or the less viscous the solvent, the more that molecule will rotate in space before the excited fluorophore emits light. In this fast rotation scenario, there is a decreased chance that the emitted light will have its electric vector approximately aligned with the direction of the polarized excitation and, thus, the polarization of this emission will be low.

In Depolarization After Resonance Energy Transfer-based detection (DARET), the polarizing light excites the donor fluorophore and the excited donor fluorophore is able to transfer its excited state energy to an acceptor fluorophore that is in close proximity. However, the acceptor fluorophore usually will have a different orientation relative to the donor molecule and hence its absorption dipole moment is not generally aligned with the donor emission dipole. In this situation, emission from the acceptor fluorophore will have a lower polarization than that characteristic of the donor fluorophore. Thus, the light emitted from the acceptor fluorophore will have an electric vector which is not aligned with the direction of the polarized exciting light.

Upon separation of the donor fluorophore and acceptor fluorophore, however, the situation is different. The only acceptor fluorophore emission which can be observed in this case is from those acceptor fluorophores which are directly excited by the polarizing light because the acceptor fluorophores are now too distant from the donor fluorophore for resonance transfer energy to occur. In the Examples shown herein, the acceptor fluorophore will have a higher polarization than that characteristic of the fluorescence which arises after energy transfer. The end result is that the polarization after separation will be larger than the polarization before separation.

Thus, DARET uses the non-parallel orientation of the dipole moments emanating from the donor and acceptor fluorophores to measure polarization changes, rather than, as in FRET, the ratio of fluorescence intensity obtained by measuring donor fluorophore and acceptor fluorophore emission maximum. As such, DARET measures the change in polarizing light that is emitted by the acceptor fluorophore. While a change in fluorescence intensity of the donor and acceptor fluorophores, as in FRET, or rotational relaxation, as in FP, may also be occurring in this method, DARET does not rely on either fluorescence intensity or rotational relaxation in its detection scheme.

The use of DARET has provided several advantages. One advantage is that the absolute nature of the measurement does not rely on any particular instrument platform used to obtain the data. This feature is in contrast to fluorescence intensity-based FRET assays which will have different intensity ratios depending upon the precise instrumentation utilized. Also DARET is not sensitive to the actual size or volume of the emitting species, whereas normal FP measurements rely upon a significant change in the rotational rates of the fluorophores before and after the change in distance between molecular features, such as ligand receptor binding or protease cleavage takes place.

Thus, in one embodiment, the present invention is drawn to a method for determining the proximity of two or more molecular features in a sample, comprising contacting in said sample, a first molecular feature labeled with a donor fluorophore having a first absorption spectrum and a first emission spectrum, and a second molecular feature labeled with an acceptor fluorophore having a second absorption spectrum overlapping with the first emission spectrum and a second emission spectrum; irradiating said sample with plane polarized light at a wavelength within said first absorption spectrum; detecting fluorescence polarization of the sample at a wavelength within said second emission spectrum; and correlating a change in energy transfer and in polarization with a change in proximity of the first and second molecular features to each other over time or relative to a control.

In an optional embodiment, the acceptor fluorophore is joined to a bulking group effective to at least somewhat restrain the free rotation of the dipole moment of the acceptor fluorophore. In these aspects of the invention the presence of the bulking group may enhance the detection of changes in proximity of two or more molecular features, such as by increasing the sensitivity or dynamic range of the assay.

Thus, another exemplary, and, optional embodiment of the invention involves a method for determining whether two or more molecular features are in proximity or not, comprising: in a fluid phase contacting a first molecular feature labeled with a donor fluorophore having a first absorption spectrum and a first emission spectrum, and a second molecular feature labeled with an acceptor fluorophore having a second absorption spectrum overlapping with the first emission spectrum, wherein, when the donor fluorophore is excited with light polarized in a first plane under conditions permitting resonance energy transfer between the donor fluorophore and acceptor fluorophore, the acceptor fluorophore emits light depolarized with respect to said first plane, compared to the polarized light emitted by said acceptor fluorophore under conditions not permitting resonance energy transfer, wherein a decrease in energy transfer and increase in polarization over time or relative to a control indicates that the distance between the first and second features has increased, while an increase in energy transfer and decrease in polarization over time or relative to a control indicates that distance between the first and second features has decreased.

In other embodiments, the present invention is drawn to a method for determining whether two or more molecular features in a sample are in proximity comprising: contacting in said sample, a first molecular feature labeled with a donor fluorophore having a first absorption spectrum and a first emission spectrum, and a second molecular labeled with an acceptor fluorophore having a second absorption spectrum overlapping with the first emission spectrum and a second emission spectrum; irradiating said sample with plane polarized light at a wavelength within said first absorption spectrum; detecting polarization of the sample fluorescence at a wavelength within said second emission spectrum; and correlating a change in energy transfer and in polarization with a change in proximity of the first and second molecular features to each other, said change relative to the energy transfer and polarization of emitted light from either the same sample at a different time or from a control.

In variations on this embodiment of the invention the method may contain one or more of the following additional elements, where the elements are consistent with each other:

The embodiment wherein the first and second molecular features are comprised in the same molecule.

The embodiment wherein the molecule comprises an amino acid sequence.

The embodiment wherein the first molecular feature is comprised in an amino terminal half of said amino acid sequence.

The embodiment wherein the first molecular feature is comprised in a carboxyl terminal half of said amino acid sequence.

The embodiment wherein at least one of said donor and acceptor fluorophore comprises a polypeptide joined to said molecule.

The embodiment wherein at least one donor or acceptor fluorophore is joined to said molecule by a peptide bond.

The embodiment wherein at least one fluorophore comprises a polypeptide selected from the group consisting of a green fluorescent protein, a blue fluorescent protein, a red fluorescent, a cyan fluorescent protein, and a yellow fluorescent protein.

The embodiment wherein either or both a donor and an acceptor fluorophore comprise a polypeptide joined to said molecule.

The embodiment wherein at least one of a donor and an acceptor fluorophore is selected from the group consisting of an Alexa Fluor® dye; fluorescein; a fluorescein derivative; diaminotriazinylaminofluorescein (DTAF); a biarsenic derivative of fluorescein; fluorescein arsenical hairpin binding dye (FlAsH™); red biarsenical dye (ReAsH™); carboxyfluorescein (FAM); Texas Red™; tetramethylcarboxyrhodamine (TMR); carboxy-x-rhodamine (ROX); rhodamine green; Oregon Green 488; BODIPY-TR®; BODIPY-TMR®; BODIPY-FL®; Cy3, Cy3B™ and Dansyl.

The embodiment wherein at least one donor and acceptor fluorophore is joined to a molecular feature by means of a linker, which may be a bi-functional reagent.

The embodiment wherein a joining linker contains a reactive moiety selected from the group consisting of thiol, haloacetyl, N-hydroxysuccinamide, vinyl sulfone, and maleimide.

The embodiment wherein at least one of the first and second molecular features comprises a polynucleotide region.

The embodiment wherein at least one molecular comprises a lipid or a carbohydrate moiety.

The embodiment wherein the first and second molecular features are contained in different molecules or cellular structures.

The embodiment wherein at least one of said first or second molecular features is comprised in a cell membrane.

The embodiment wherein one of said first and second molecular features is comprised in a vesicle.

The embodiment wherein one of said first and second molecular features comprises a receptor.

The embodiment wherein one of said first and second molecular features comprises an antibody variable region.

The embodiment wherein one of said first and second molecular features comprises a receptor ligand.

The embodiment wherein one of said first and second molecular features comprises a polypeptide.

The embodiment wherein one of said first and second molecular features comprises a lipid.

The embodiment wherein said lipid comprises a phospholipid.

The embodiment wherein at least one of the first and second molecular features comprises cholesterol or a cholesterol derivative.

The embodiment wherein said lipid comprises a prostaglandin or prostaglandin derivative.

The embodiment wherein at least one of said first or second molecular feature comprises a polynucleotide region.

The embodiment wherein both said first and second molecular feature comprise a polynucleotide region.

The embodiment wherein at least one donor or acceptor fluorophore is joined to at least first or second molecular feature by a peptide bond.

The embodiment wherein the correlating step comprises correlating an increase in polarization with a decrease in the distance between the first and second molecular features to each other over time or relative to a control, and correlating a decrease in polarization with an increase in of the distance between the first and second features to each other over time or relative to a control.

The embodiment wherein the correlating step comprises correlating a decrease in polarization with a decrease in distance between the first and second molecular features to each other over time or relative to a control, and correlating an increase in polarization with an increase in the distance between the first and second features to each other over time or relative to a control.

In some embodiments of the invention, the result of the assay may be that a decrease in polarization occurs as the distance between the first and second molecular feature increases; in other embodiments of the invention the result of the assay may be that an increase in polarization occurs as the distance between the first and second molecular feature increases. Thus, the present methods provide, in a broader embodiment, a change in the polarization of light emitted by an acceptor fluorophore when the distance between it and the donor fluorophore increases; the donor and acceptor fluorophores are each joined to separate molecular features.

By "molecular feature" is meant a molecular or cellular region whose proximity to one or more other molecular or cellular regions is sought to be ascertained in the methods of the present invention. Different molecular features may be parts of the same molecule, for example, without limitation, the amino and carboxyl termini of a protein, two internal sites within a protein, the 5' and 3'-ends of a polynucleotide molecule or two internal sites of a polynucleotide molecule. Alternatively, different molecular features may be part of different molecules; an example of this aspect includes antibody/antigen pairs, DNA binding protein and a polynucleotide binding region like a promoter, repressor or enhancer region, a lipid/membrane protein pair or ligand/receptor pairs. Additionally, a molecular feature may be a cellular organelle, such as, for example, the plasma membrane, wherein the label may be intercalated or otherwise associated with the molecular feature without necessarily being covalently linked to any molecule. In such a use, the association of another labeled molecular feature (for example, a molecular feature comprised in a membrane-targeted protein) with the plasma membrane would, under the conditions described in the present application, result in DARET and a change in polarization as compared to the labeled molecular feature on the unassociated protein.

By "contacting", as used in the claims, is meant that the molecular features are brought together under conditions that permit their interactivity (to the degree effective to permit resonance energy transfer between the labels), either initially, over a period time, or as compared to a control. Thus, contacting labeled molecular features whose intramolecular proximity is sought to be determined may simply involve labeling two or more different molecular features of the same molecule. Alternatively, contacting, for example, two molecular features whose intermolecular proximity is sought to be ascertained may involve mixing together molecular features that are comprised in different molecules or cellular loci under conditions in which their molecular proximity will differ over time or with reference to a control.

A "fluid phase" may include a gas phase or a liquid phase, and contacting molecular features in a fluid phase requires only that one of the molecular features is in a fluid phase. Thus, said contacting may mean that the features are both in the gas phase, both in the liquid phase, or that one molecular feature is in a phase selected from the group consisting of gas and liquid, and that the other molecular feature is selected from a different phase selected from the group consisting of gas, liquid and solid.

For example, different molecular features of the same molecule can be labeled with different fluorophores capable of acting as DARET partners as set forth herein and as is otherwise known to the person of ordinary skill in the art, in a manner than permits these features to come close enough to each other that resonance energy transfer may take place between the fluorescent labels. Subsequent digestion, cleavage or destruction of the molecule can result in the cessation of resonance transfer energy between these molecular features. As an example, a protein may be labeled with two fluorescent labels, one at or near the amino terminus of the protein and the other at or near the carboxyl terminus. Proteolysis at a peptide bond between the two molecular features would result in the dissociation of the labels, and end the resonance energy transfer between these labels.

In another example of contacting molecular features, a nucleic acid may be introduced into a cell under conditions that permit the expression of an encoded protein. The protein may be a fusion protein in which, for example, a green fluorescent protein (GFP) coding sequence is introduced at the amino or carboxyl terminus. If the plasma membranes of the host cells are loaded with a lipophilic fluorescent dye, the migration of the expressed protein to the membrane may be detected by a change in DARET. Moreover, the association of the protein with the cell membrane would also result in a change in polarization of the light emitted by the membrane-associated fluor, due to energy transfer depolarization, as described previously.

In yet another example, a molecular feature comprised in an antigen may be labeled with a fluorescent acceptor. A single chain synthetic antibody is designed, expressed, and purified in which a GFP donor moiety is present in a molecular feature. The association of the antigen and antibody permits FRET between the labels, and the association of the antigen with the GFP/antibody fusion protein causes a difference in fluorescent polarization due to the resulting energy transfer between imperfectly aligned donor and acceptor.

While not limiting the invention, and not wishing to be limited by theory, the Applicants believe that certain changes in fluorescence polarization are in part an indication of differences in the orientation of a molecule (actually, differences in the orientation of the dipole moment of a fluorophore) between the time it is excited by light at or near the absorbance maximum and sometime later when it (or another fluorescent molecule which becomes excited as a result of resonance energy transfer from the first) emits light of a longer wavelength. Thus, when the fluorophore is, for example, locked in a crystal form, very little movement of the dipole moment is possible and emitted light remains extremely polarized. Likewise, in a viscous solution, the fluorophore has a somewhat restricted ability to move, although much greater than when in a crystalline form, and the emitted light will remain largely polarized. The dipole moment of a fluorescent molecule in an aqueous solution of low viscosity will have substantially greater ability to rotate than those of either of the other two examples, and the resulting emitted light will be accordingly more depolarized.

As an illustration only, Applicants believe that another way in which changes in fluorescent polarization may be induced is when there is non-radiative resonance energy transfer between fluorescent molecules in proximity to each other. At very high concentrations or under other suitable conditions energy transfer may occur when plane polarized light striking a collection of randomly oriented molecules will only be absorbed by and excite those molecules having dipole moments oriented in approximately the identical (or the reciprocal) plane as the exciting light. These excited molecules may through resonance energy transfer then transfer the excited state to another molecule having a slightly differently oriented dipole moment. When the excited molecule emits light, the resulting fluorescence may have an orientation quite unrelated to the orientation of the original plane polarized light. Thus, the polarization of the excitation light is observed as decreased due to resonance energy transfer by an excited molecule to a ground state molecule not oriented in the exactly the same plane as the light, and subsequent emission of less polarized light.

An advantage of the currently disclosed invention is the fact that traditional FP relies on changes in the orientation of the dipole moment of a fluorophore occurring due to rotation of the molecule between excitation and emission. By contrast, the DARET methods described herein, which result from non-radiative energy transfer between molecules of similar but different orientation, do not require (but nevertheless may involve) a difference in bulk or molar volume between the first and second molecular feature.

As stated above, it may be important in certain embodiments of the invention that there is a difference in volume between the labeled molecular features when they are in close proximity and when they are not in close proximity. In some less preferred embodiments of the invention, the molecular feature linked to the donor fluorophore has a significantly lower volume when it is not in proximity to the acceptor fluorophore than its apparent volume when it is in close proximity to the acceptor fluorophore.

In certain embodiments of the invention, such as in protease assays using relatively small polypeptide substrates, the present assays may benefit from the use of a bulking group linked to the molecular feature associated with or joined to the one of the fluorophores; in such a case it is also helpful, but not necessarily essential that the molecular feature associated with or joined to the other fluorophore is not linked to a bulking group. The family of fluorescent proteins such as green fluorescent protein (GFP) can constitute such bulking groups, as these polypeptides form large, stable, barrel-like tertiary structures to protect the fluorophore, composed of modified amino acids, within. See e.g., Fang et al., *Nature Biotechnology* 14:1246-1251 (1996).

In a specific embodiment, further provided herein is a method of determining the presence or activity of a protease by (a) treating with a sample, under conditions suitable for protease activity, a protease substrate containing (i) a donor fluorophore; (ii) an acceptor having an absorbance spectrum overlapping the emission spectrum of the donor fluorophore; and (iii) a protease recognition sequence containing a cleavage site, where the cleavage site intervenes between the donor fluorophore and the acceptor and where, under the appropriate conditions, resonance energy transfer is exhibited between the donor fluorophore and the acceptor; (b) exciting the donor fluorophore with plane polarized light; and (c) determining fluorescence polarization of the treated substrate relative to a control substrate, where a change (increase or decrease) in fluorescence polarization of the treated substrate as compared to fluorescence polarization of the control substrate is indicative of the presence or activity of the protease.

BRIEF DESCRIPTION OF THE DRAWINGS

FIG. 1 shows the DARET assay of BoNT/A complex (900 kDa) with the GFP-SNAP25-2×BFP substrate in the cuvette-based assay format. Final reaction conditions were 200

BoNT/A complex and 10 µM substrate. The negative control contained the substrate with no toxin.

Figure 2:
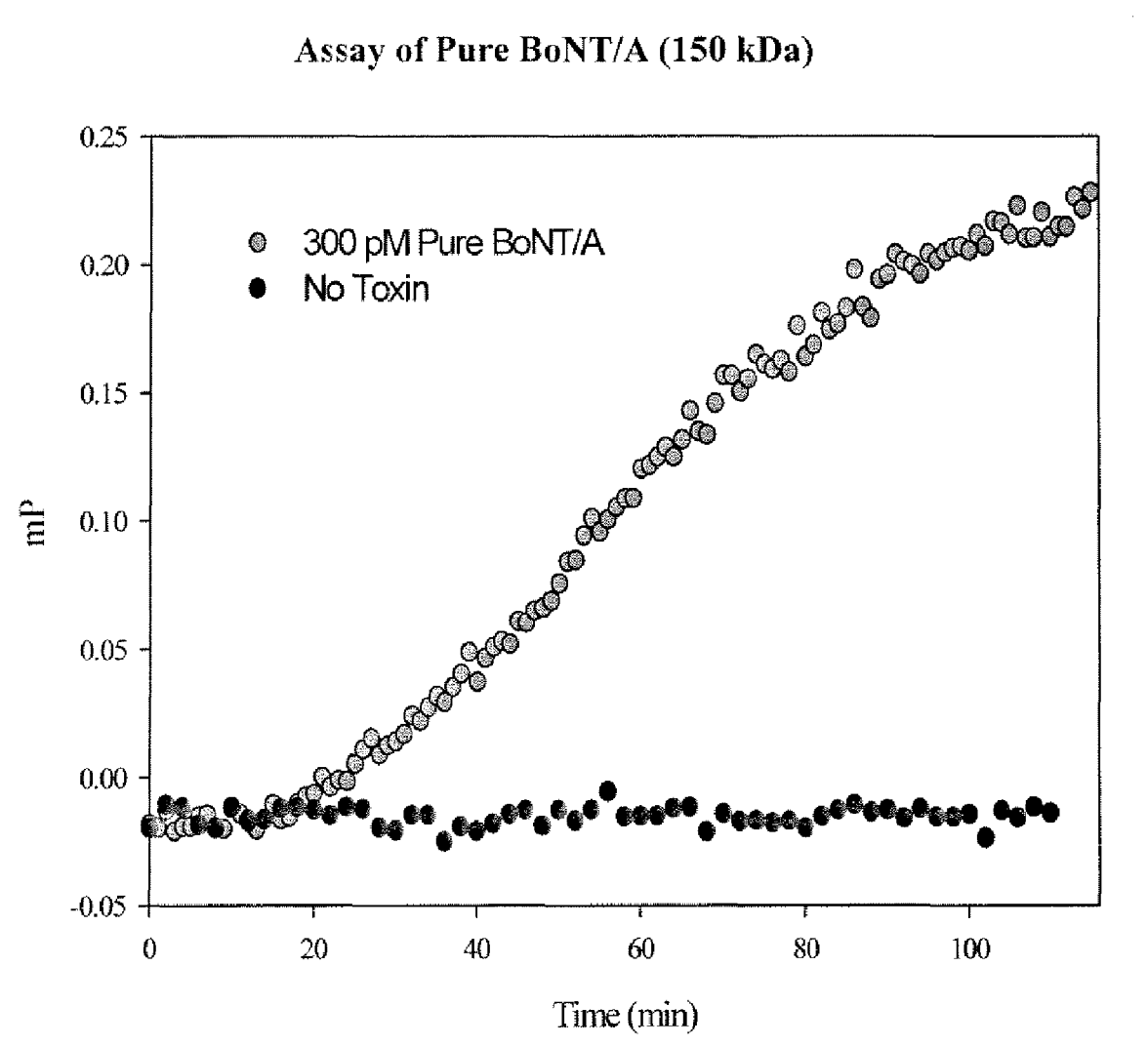

FIG. 2 shows the DARET assay of purified BoNT/A (150 kDa) with the GFP-SNAP25-2×BFP substrate in the cuvette-based assay format.

Figure 3:
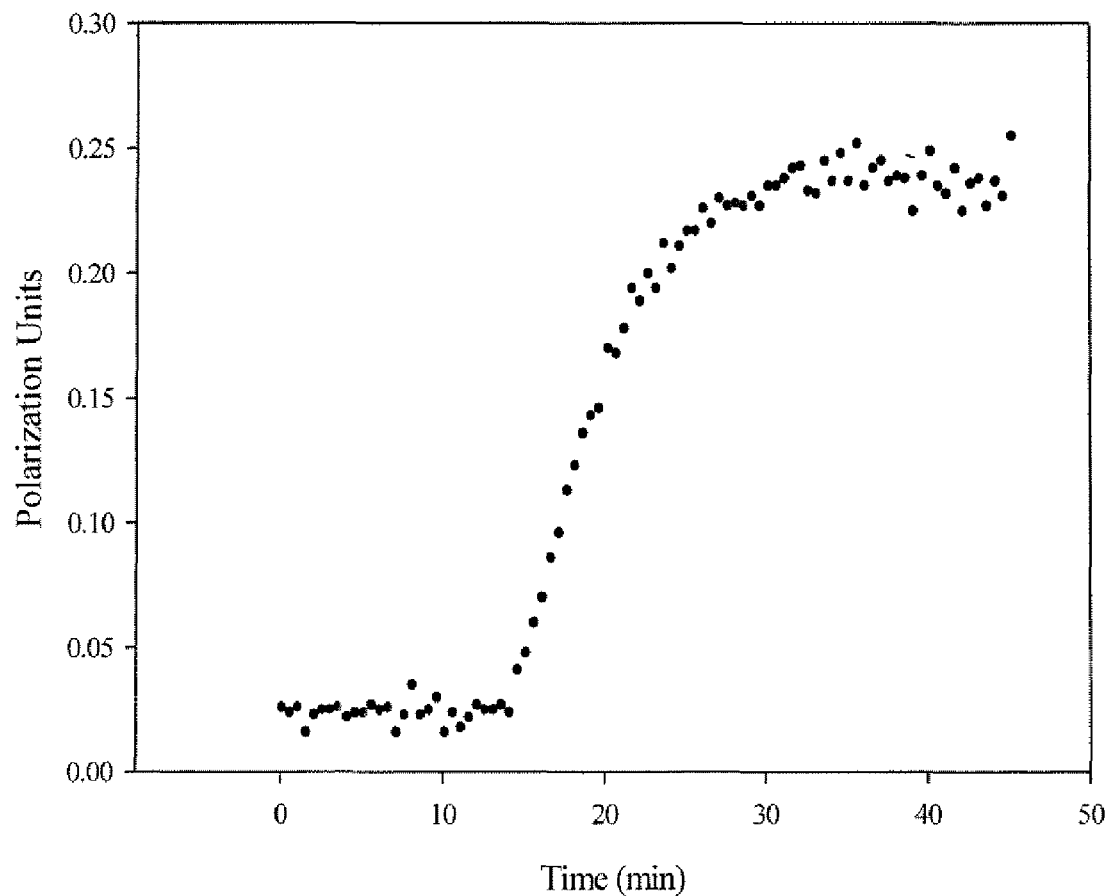

FIG. 3 shows the DARET assay of rLC/A using the GFP-SNAP25-2×BFP substrate in a cuvette-based format.

Figure 4:
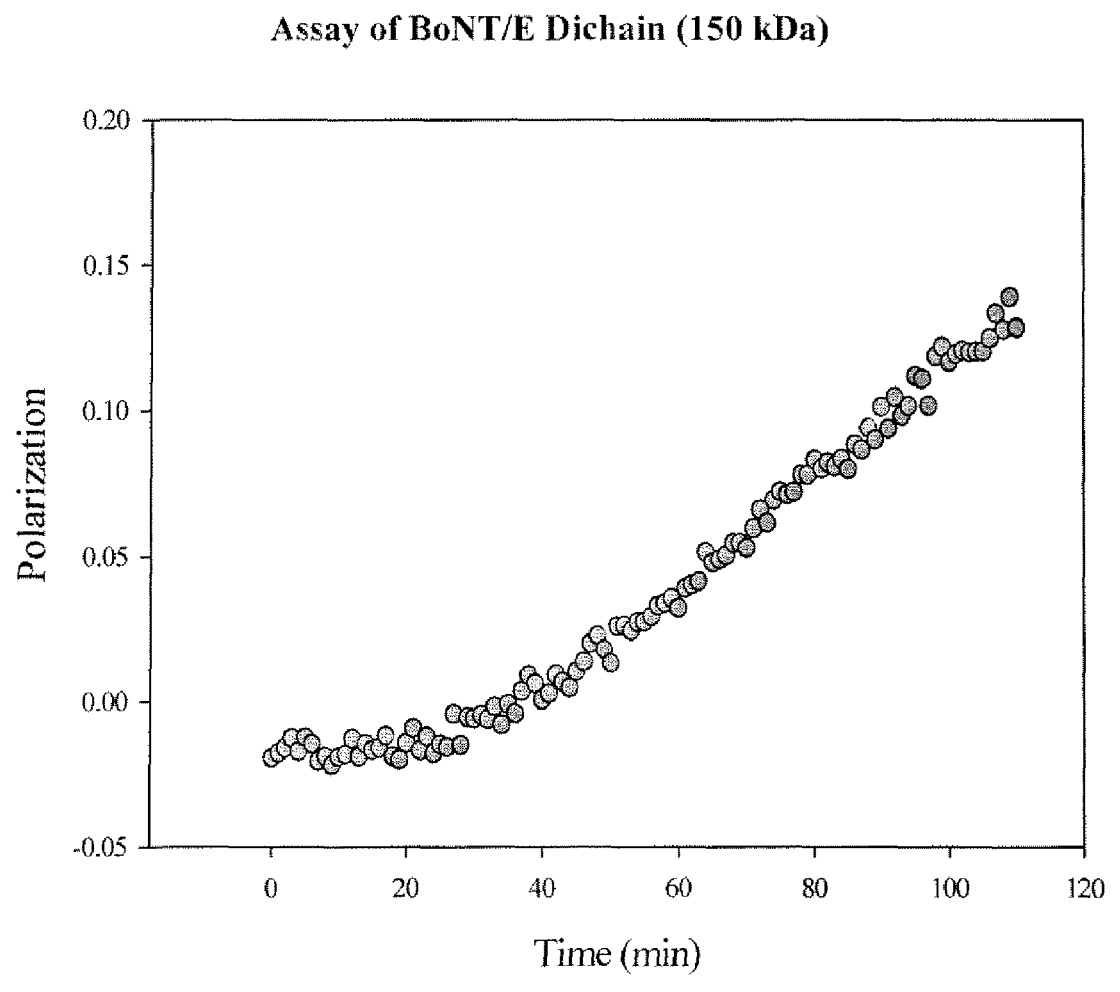

FIG. 4 shows a cuvette-based assay of BoNT/E activity using the DARET assay with the GFP-SNAP25-2×BFP substrate.

Figure 5:
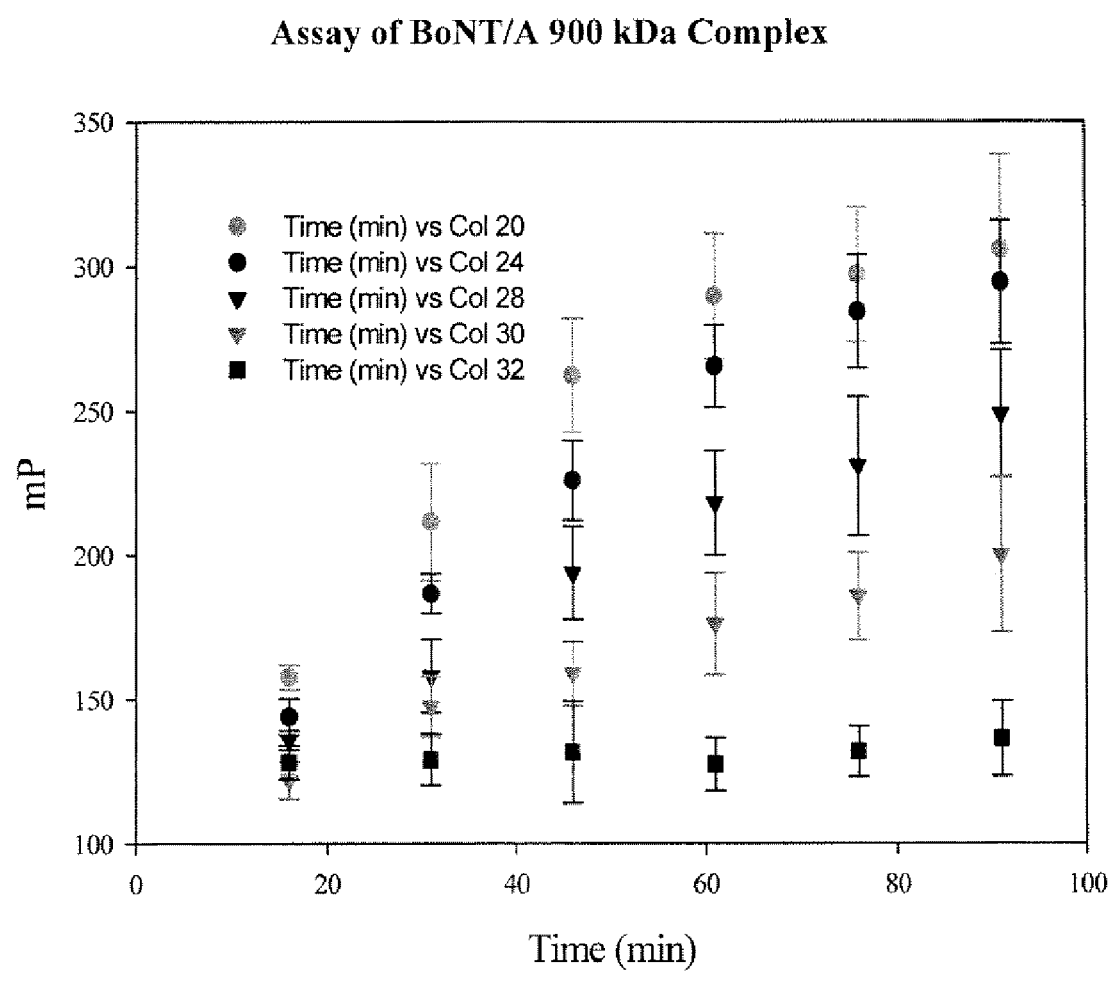

FIG. 5 shows the plate-based DARET assay of BoNT/A complex (900 kDa) with the GFP-SNAP25-1×BFP substrate.

Figure 6:
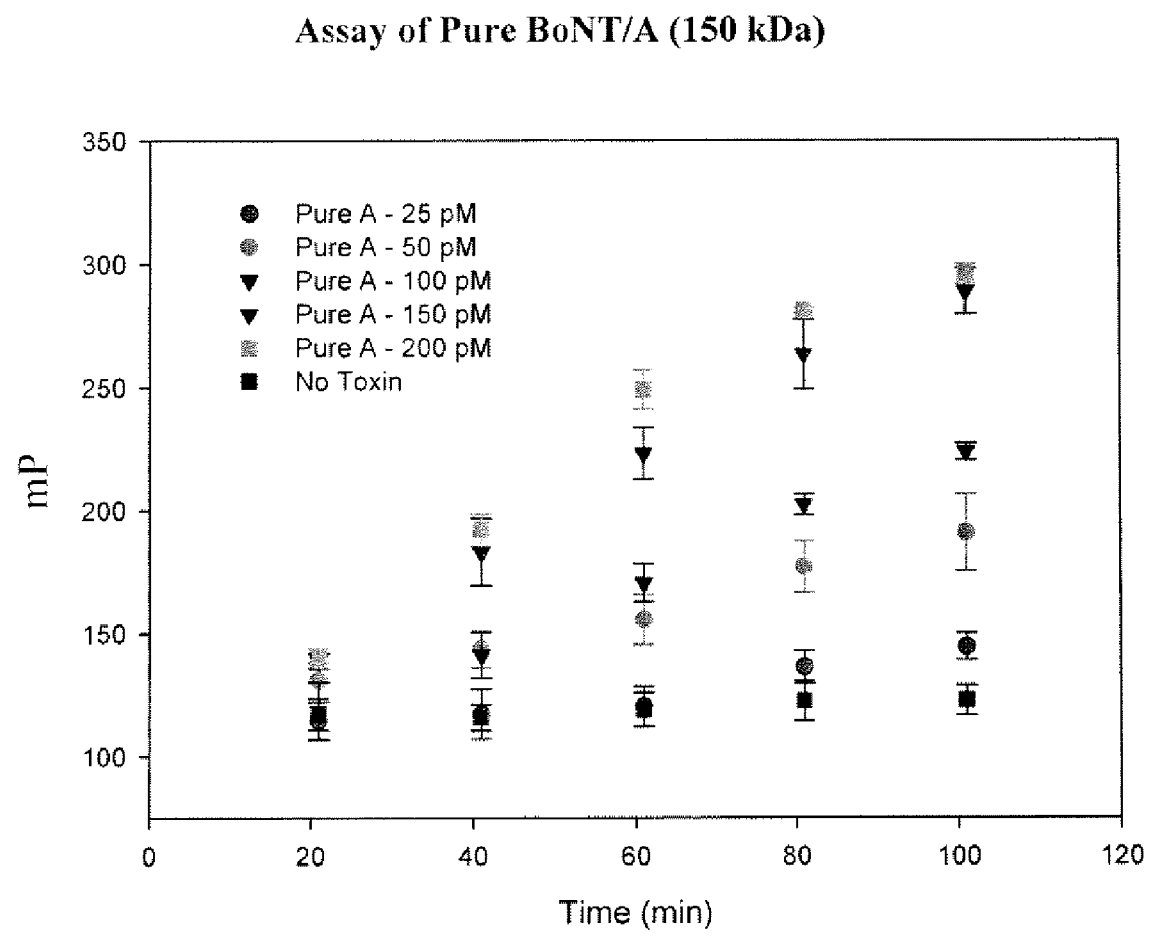
Figure 7:
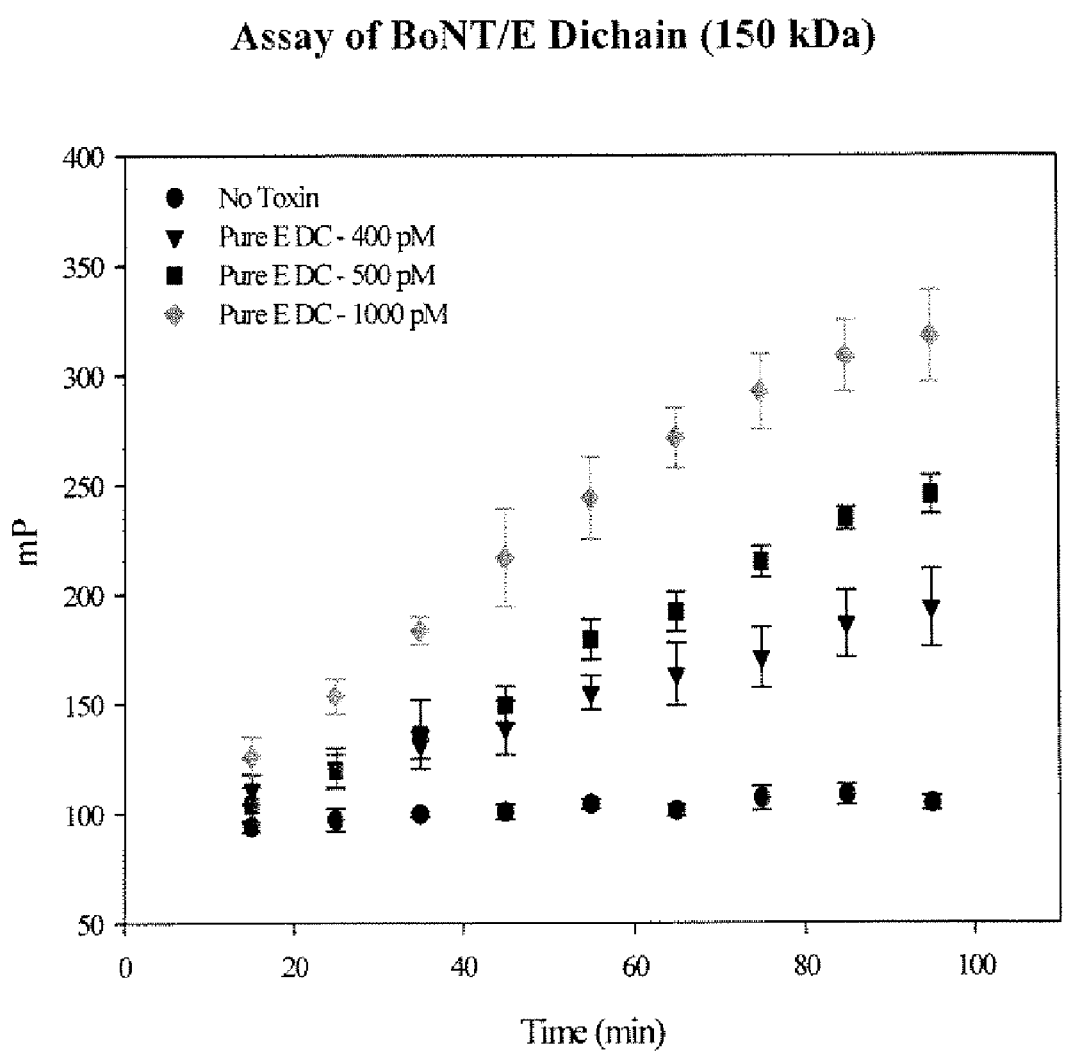
Figure 8:
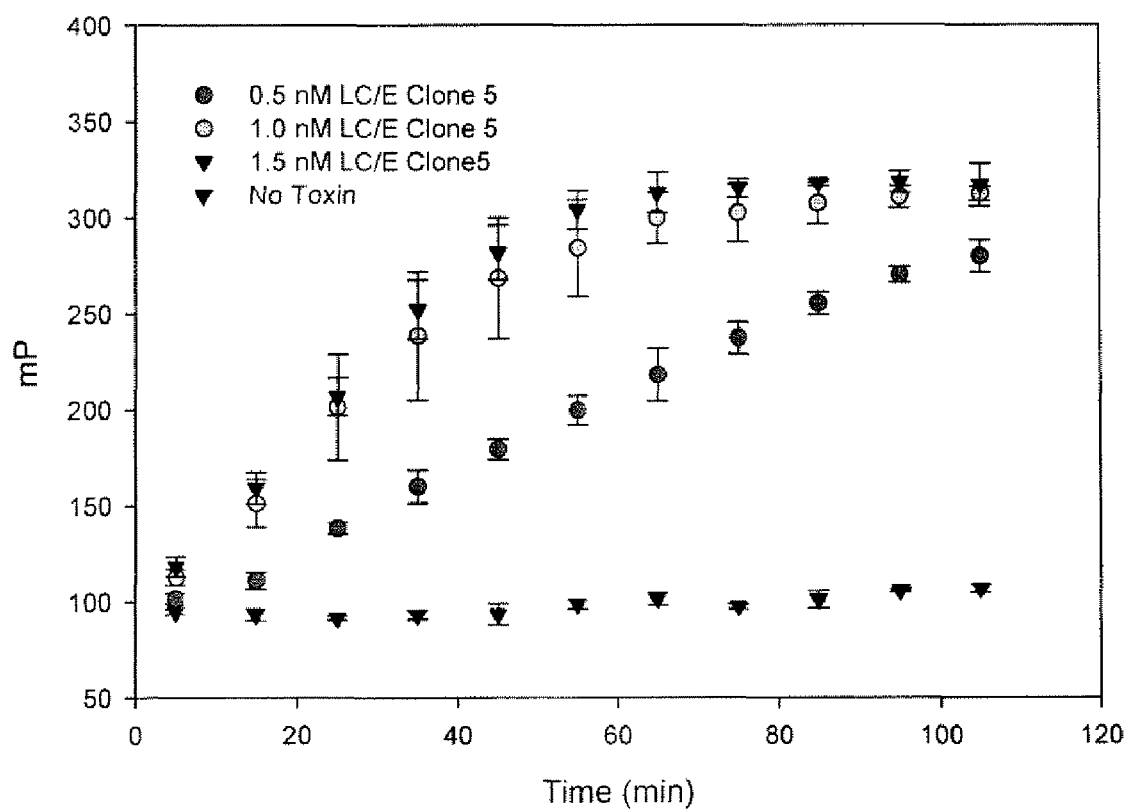

FIGS. 6, 7, and 8 show DARET assays of pure BoNT/A, BoNT/E and rLC/E, respectively, in similar plate-based assay formats using the GFP-SNAP25-1×BFP substrate.

Figure 9:
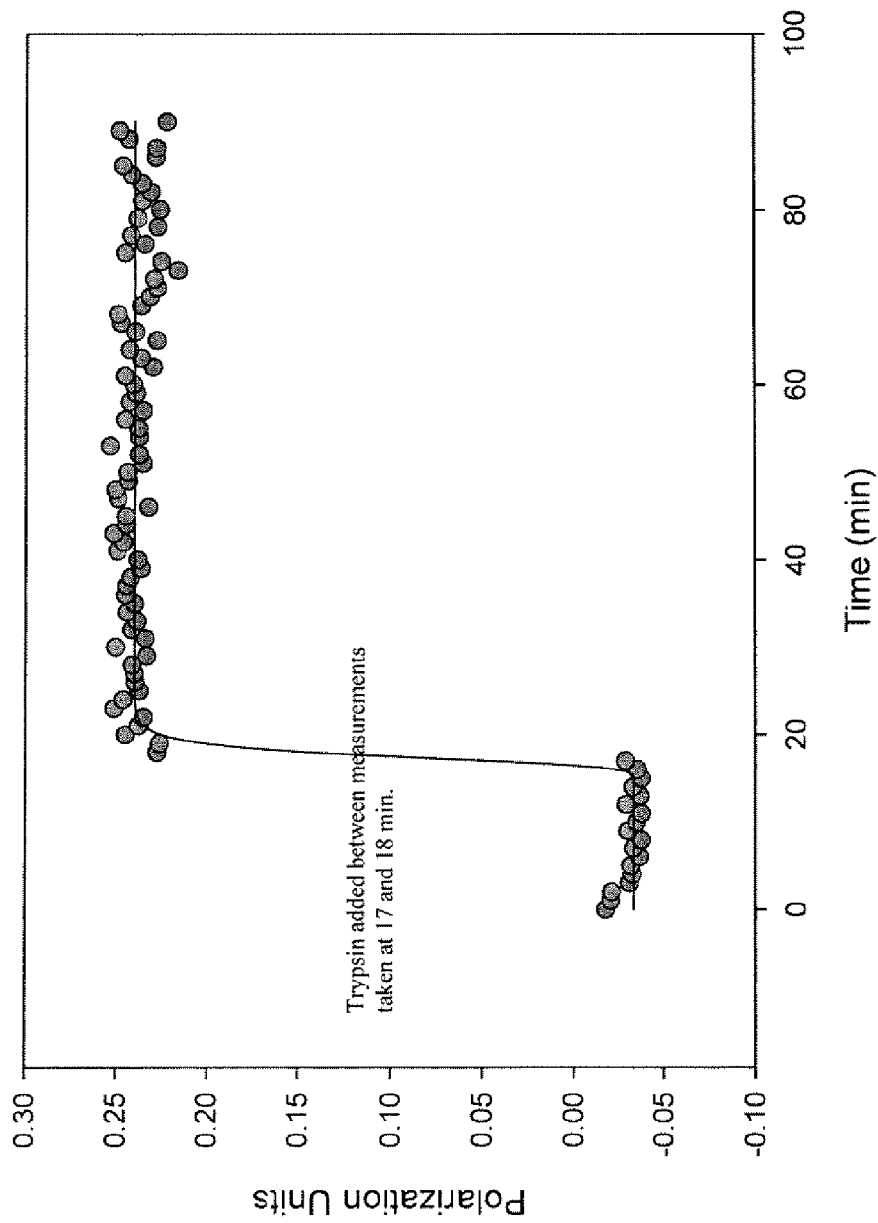

FIG. 9 shows the results of DARET upon the cleavage of GFP-SNAP25-1×BFP with added trypsin.

DETAILED DESCRIPTION

The present invention provides methods for monitoring the proximity of two or more molecular features located on the same molecule or on different molecules. Thus, as a non-limiting example, the present methods may be used in protease assays, particularly those employing a substrate useful for fluorescence polarization analysis, such as, for example, one having at least one donor and one acceptor fluorophore each joined to a molecular feature separated from another molecular feature by a protease cleavage site. The combination of resonance energy transfer and fluorescence polarization analysis results in extremely sensitive detection methods that may suffer less from interference due to fluorescent background in the sample than traditional FRET-based assays. Furthermore, the novel methods of the invention can be performed as homogeneous solution-phase assays and are amenable to automated high-throughput formats and real-time analysis without the need for sample consumption.

These methods are also suitable for other proximity analyses such as, without limitation, receptor-ligand binding studies, intracellular trafficking studies, co-localization of proteins and other molecules, membrane localization studies, kinase autophosphorylation assays and the like. See, e.g., D. Mochinsky et al., *J. Biomol. Screening, Vol.* 8, 447-452 (2003). Indeed, virtually any assay application for which FRET may currently be used is amenable to use in the DARET assays described herein. Thus, one may use the DARET assay methods of the present invention to investigate, for example and without limitation:

1) The structure and conformation of proteins (See e.g., Jonsson, T. et al., *Biochemistry* 35:4795-4802 (1996)); see e.g., Wells, et al., Method For Identifying Active Domains And Amino Acid Residues In Polypeptides And Hormone Variants, U.S. Pat. No. 6,428,954; Craig, et al., Methods and Compositions Using Protein Binding Partners, U.S. Pat. No. 9,672,198);

2) The spatial distribution and assembly of proteins (See e.g., Watson, B. S. et al., *Biochemistry* 34:7904-7912 (1995));

3) Receptor/ligand interactions (See e.g., Berger, W. et al., *Biochemistry* 33: 1875-11883 (1994); Nakayama et al., Fluorescence Polarization Method, U.S. Pat. No. 6,432,632; Lustig et al., Nuclear Hormone Receptor Drug Screens, U.S. Pat. No. 7,101,681; Huggins, et al., Specific Binding Assay Techniques, U.S. Pat. No. 4,211,762; Sippel et al., Method For The Cellular High-Throughput-Detection Of Receptor Ligand Interactions, U.S. Pat. No. 7,029,905);

4) Immunoassays (See e.g., Khanna, P. L. et al., *Anal. Biochem.* 108:156-161 (1980); Magnusson et al., Immunoassay Of Proteins, U.S. Pat. No. 4,455,381; Newman et al., Immunoassay Of Thymosin $\alpha_1$, U.S. Pat. No. 4,427,783; Hammerling et al., Process For Sex Determination In Man By Use Of Monoclonal Antibodies To The H-Y Antigen, U.S. Pat. No. 4,680,258; Forrest et al., Immunoassay Of Antigens, U.S. Pat. No. 4,659,678; Gay, Vitro Diagnostic Methods Using Monoclonal Antibodies Against Connective Tissue Proteins, U.S. Pat. No. 4,628,027; Ota et al., Amyloid-β Protein Aggregation-Regulating Factors, U.S. Pat. No. 7,029, 860);

5) Structure And Conformation Of Nucleic Acids (See e.g., Clegg, R. M. et al., *Biophys. J.* 66:99-109 (1994); Weiss et al., Semiconductor Nanocrystal Probes For Biological Applications And Process For Making And Using Such Probes U.S. Pat. No. 6,207,392);

6) Real-time PCR assays and SNP detection (See e.g., Lee, L. G., *Biotechniques* 27:342-349 (1999); Myakishev, M. V., *Genome Res.* 11:163-169. 2001; Cockerill et al., Detection of Legionella, U.S. Pat. No. 6,830,888; Parkhurst et al., Method For Detecting Point Mutations In DNA Utilizing Fluorescence Energy Transfer, U.S. Pat. No. 6,248,518;

7) Nucleic Acid Hybridization (See e.g., Parkhurst, K. M. et al., Biochemistry 34:285-292 (1995)); Clark et al, Diagnostics and Therapeutics for Glaucoma, U.S. Pat. No. 7,033, 755; Stefano et al., Methods, Kits And Compositions For Detecting And Quantitating Target Sequences U.S. Pat. No. 6,287,772; Gellibolian et al., Methods And Compositions For High Throughput Identification Of Protein/Nucleic Acid Binding Pairs U.S. Pat. No. 6,713,262; Smith et al., Detection Of Herpes Simplex Virus U.S. Pat. No. 6,958,210; Cockerill et al., Detection Of Vancomycin-Resistant *Enterococcus* spp. U.S. Pat. No. 7,074,598);

8) Distribution And Transport Of Lipids (See e.g., Nichols, J. W. et al., J. Biol. Chem. 258:5368-5371 (1983)); Normant et al, Methods And Compositions For Screening Modulators Of Lipid Kinases, U.S. Pat. No. 6,723,525; Hammock et al., Linoleic Acid Diol And Glucuronide Conjugate Levels As Diagnostic Markers Of Disorders Of Abnormal Regulation Of Cytochrome P450 Metabolism Of Unsaturated Fatty Acids, U.S. Pat. No. 6,756,210; Kreiger et al., Methods For Modulation Of Lipid Uptake, U.S. Pat. No. 5,925,333; Drees et al., Assaying Apparatus, Kit, And Method For Lipids And Associated Enzymes, U.S. Pat. No. 7,067,269; Lusk et al., Monoclonal Antibodies For Assaying Lipid Transfer Proteins, U.S. Pat. No. 6,423,546);

9) Membrane Fusion Assays (See e.g., Uster P. S., *Methods Enzymol.* 221:239-246 (1993));

10) Membrane Potential Sensing (See e.g., Hoffman, R. et al., Bio-Tek Application Not)e. http:www.biotek.com/products/tech_res_detail.php?id=135; Gonzalez, J. E. et al., Biophys. J. 69:1272-1280 (1995)); Farinas et al., Use Of Nernstein Voltage Sensitive Dyes In Measuring Transmembrane Voltage; U.S. Pat. No. 6,979,553; Tsien et al., Detection Of Transmembrane Potentials By Optical Methods, U.S. Pat. No. 6,107,066; Negulescu et al., Photon Reducing Agents For Reducing Undesired Light Emission In Assays U.S. Pat. No. 6,214,563; Tsien et al., Detection Of Transmembrane Potentials By Optical Methods, U.S. Pat. No. 6,596,522; Tsien et al., Detection Of Transmembrane Potentials By Optical Methods, U.S. Pat. No. 6,342,379);

11) Protease Assays (See e.g., Matayoshi E. D., et al., Science 247, 954-958 (1990); Shone et al., Toxin Assay U.S. Pat. No. 6,337,386; Auld, Methods for Measuring Kinase Activity U.S. Pat. No. 6,942,987; Darrow et al., Methods for Identifying Modulators of Serine Protease EOS, U.S. Pat. No. 6,806,059; Shine et al., Substrate Peptides And Assays For Detecting And Measuring Proteolytic Activity Of Serotype A Neurotoxin From *Clostridium Botulinum*, U.S. Pat. No. 6,504,006; Darrow et al., DNA encoding the human serine protease T, U.S. Pat. No. 6,458,564; Darrow et al., Zymogen Activation System U.S. Pat. No. 6,420,157); and 12) Indicators for cyclic AMP (See e.g., Adams S. R. et al., Optical Probes for Cyclic AMP, Fluorescent and Luminescent Probes for Biological Activity, pp. 133-149 (Mason W. T., Ed. (1993) Tomlinson, Cloning And Characterization Of A Human Adenylyl Cyclase, U.S. Pat. No. 7,115,570; Reymond, Use Of The Regulatory Subunit Of The Camp Dependent Protein Kinase (Pka) From *Dictyostelium* For Camp Measurements U.S. Pat. No. 6,573,059; Garman, Fluorescence Energy Transfer Substrates; U.S. Pat. No. 6,291,201).

Each of the above referenced publications and patents are hereby incorporated herein by reference as part of the present specification.

In a particularly useful aspect of the invention, the present methods may be useful for determining the presence or activity of clostridial toxins including botulinum toxins of all serotypes as well as tetanus toxins. These aspects of the invention, which rely on a clostridial toxin substrate useful for DARET analysis, reduce the need for animal toxicity studies and can be used to analyze crude and bulk samples of clostridial neurotoxin as well as highly purified dichain or single chain toxins, toxin complexes, formulated toxin products or the toxin derivatives, such as those disclosed in U.S. Pat. No. 6,843,998.

In the DARET methods of the invention, the method involves a molecular feature which include, in part, a donor fluorophore or an acceptor fluorophore, or both. As used herein, the term "fluorophore" means a molecule that, when irradiated with light of a certain wavelength, emits light of a different wavelength. The term fluorophore is synonymous in the art with the term "fluorochrome." A "donor fluorophore" is a molecule that, when irradiated with light of a certain wavelength transfers energy to the acceptor via a non-radiative resonance energy transfer. As used herein, the term "acceptor fluorophore" means a molecule that can absorb energy from, and upon excitation of, a donor fluorophore.

It is envisioned that any and all fluorophores can serve as a donor fluorophore or an acceptor fluorophore for DARET, including, without limitation, a fluorescent protein, a fluorophore binding protein and a fluorescent dye. One skilled in the art understands that these as well as other fluorophores suitable for DARET are known in the art and can be useful in the methods of the invention.

A donor fluorophore or an acceptor fluorophore disclosed in the present specification can be, in part, a fluorescent protein. As used herein, the term "fluorescent protein" means a peptide which absorbs light energy of a certain wavelength and emits light energy of a different wavelength and encompasses those which emit in a variety of spectra, including violet, blue, cyan, green, yellow, orange and red, see Table 1. It is envisioned that fluorescent proteins derived from any of a variety of species can be useful in aspects of the present invention including, but not limited to, *Aequorea* fluorescent proteins, *Anemonia* fluorescent proteins, *Anthozoa* fluorescent proteins, *Discosema* fluorescent proteins, *Entacmeae* fluorescent proteins, *Heteractis* fluorescent proteins, *Montastrea* fluorescent proteins, *Renilla* fluorescent proteins, *Zoanthus* fluorescent proteins, and fluorescent proteins from other organisms. Fluorescent proteins useful in the invention encompass, without limitation, wild type fluorescent proteins, naturally occurring variants, and genetically engineered variants, produced, e.g., by random mutagenesis or rational designed, and active peptide fragments derived from an organism. Fluorescent proteins useful in aspects of the invention include, e.g., those which have been genetically engineered for superior performance such as, without limitation, altered excitation or emission wavelengths; enhanced brightness, pH resistance, stability or speed of fluorescent protein formation; photoactivation; or reduced oligomerization or photobleaching, see, e.g., Brendan P. Cormack et al., *FACS-optimized Mutants of the Green Fluorescent Protein (GFP)*, U.S. Pat. No. 5,804,387 (Sep. 8, 1998); Roger Y. Tsien & Roger Heim, *Modified Green Fluorescent Proteins*, U.S. Pat. No. 6,800,733 (Oct. 5, 2004); Roger Y. Tsien et al., *Long Wavelength Engineered Fluorescent Proteins*, U.S. Pat. No. 6,780,975 (Aug. 24, 2004); and Roger Y. Tsien et al., *Fluorescent Protein Sensors For Measuring the pH of a Biological Sample*, U.S. Pat. No. 6,627,449 (Sep. 30, 2003). It is understood that a fluorescent protein can be engineered for improved protein expression by converting wild type codons to other codons more efficiently utilized in the cells which serve to express the Clostridial toxin substrate, see, e.g., Brian Seed and Jurgen Haas, *High Level Expression of Proteins*, U.S. Pat. No. 5,795,737 (Aug. 18, 1998). A fluorescent protein can be operably-linked to a molecular feature comprising a polypeptide to create a fusion protein using standard molecular genetic techniques. Additionally, a fluorescent protein can be specifically linked to the amino- or carboxyl-terminus of a molecular feature comprising a polypeptide using well known chemical methods, see, e.g., *Chemical Approaches to Protein Engineering*, in *Protein Engineering: A Practical Approach* (Eds. Rees et al., Oxford University Press, 1992).

TABLE 1

Excitation and Emission Maxima of Exemplary Fluorescent Proteins

| Fluorescent protein | Excitation maxima (nm) | Emission maxima (nm) |
|---|---|---|
| EBFP | 380 | 440 |
| ECFP | 439 | 476 |
| AmCyan | 458 | 489 |
| AcGFP | 475 | 505 |
| ZsGreen | 493 | 505 |
| Vitality ® hrGFP | 500 | 506 |
| EGFP | 484 | 510 |
| Monster Green ® | 505 | 515 |
| EYFP | 512 | 529 |
| ZsYellow | 529 | 539 |
| DsRed-Express | 557 | 579 |
| DsRed2 | 563 | 582 |
| DsRed | 558 | 583 |
| AsRed2 | 576 | 592 |
| HcRed1 | 588 | 618 |

It is also envisioned that any of a variety of active protein fragments of a fluorescent protein can be useful in aspects of the present invention with the proviso that these active fragments retain the ability to emit light energy in a range suitable for the proper operation of aspects of the present invention, such as, e.g. 420-460 nm for blue emitting fluorescent proteins, 460-500 nm for cyan emitting fluorescent proteins, 500-520 nm for green emitting fluorescent proteins, 520-550 nm for yellow emitting fluorescent proteins and for 550-740 nm for red emitting fluorescent proteins. Thus, aspects of this embodiment can include active fragments of fluorescent proteins that retain the ability to emit light energy in a range suitable for the proper operation of aspects of the present invention having a length of, e.g., at least 50 amino acids, at least 60 amino acids, at least 70 amino acids, at least 80 amino acids, at least 90 amino acids, at least 100 amino acids, at least 125 amino acids, at least 150 amino acids, at least 175 amino acids and at least 200 amino acids. Other aspects of this embodiment, can include active fragments of fluorescent proteins that retain the ability to emit light energy in a range suitable for the proper operation of aspects of the present invention having a length of, e.g., at most 50 amino acids, at most 60 amino acids, at most 70 amino acids, at most 80 amino acids, at most 90 amino acids, at most 100 amino acids, at most 125 amino acids, at most 150 amino acids, at most 175 amino acids and at most 200 amino acids.

Thus, in an embodiment, a donor fluorophore or an acceptor fluorophore is a fluorescent protein. In aspects of this embodiment, a donor fluorophore or an acceptor fluorophore is a blue fluorescent protein, a cyan fluorescent protein, a green fluorescent protein, a yellow fluorescent protein, a red fluorescent protein or an ultraviolet fluorescent protein. In other aspects of this embodiment, both a donor fluorophore and an acceptor fluorophore can be a blue fluorescent protein, a cyan fluorescent protein, a green fluorescent protein, a yellow fluorescent protein, a red fluorescent protein or an ultraviolet fluorescent protein.

A donor fluorophore or an acceptor fluorophore disclosed in the present specification can be, in part, a fluorophore binding protein that is subsequently associated with a fluorophore. A fluorophore binding protein establishes a covalent bond, or strong non-covalent interaction, with the fluorophore in a selective chemical or biochemical reaction. Non-limiting examples of such fluorophore binding proteins and corresponding fluorophores include the bis-arsenical tetracysteine system, see, e.g., B. Albert Griffin et al., *Specific covalent labeling of recombinant protein molecules inside live cells*, 281(5374) Science 269-272 (1998); and B. Albert Griffin et al., *Fluorescent labeling of recombinant proteins in living cells with FlAsH*, 327 Methods Enzymol. 565-578 (2000); the alkylguanine-DNA-alkyltransferase (AGT) system, see, e.g., Antje Keppler et al, *A General Method for the Covalent Labeling of Fusion proteins with Small Molecules in vivo*, 21 (1) Nat. Biotech 86-89 (2003); Antje Keppler et al, *Labeling of fusion proteins of O6-alkylguanine-DNA alkyl-transferase with small molecules in vivo and in vitro*, 32(4) Methods 437-444 (2004); and Antje Keppler et al, *Labeling of Fusion Proteins with Synthetic Fluorophores in Live Cells*, 101(27) Proc. Natl. Acad. Sci. USA 9955-9959 (2004); and the dehalogenase system. In addition, non-limiting examples of fluorophore binding proteins and corresponding fluorophores, as well as well-characterized reagents, conditions and protocols are readily available from commercial vendors that include, without limitation, TC-FlAsH™ TC-ReAsH™ In-Cell Tetracysteine Tag Detection Kit (Invitrogen Corp., Carlsbad, Calif.); SNAP-tag™ multi-purpose protein tag system (Covalys Biosciences AG, Switzerland); and HaloTag™ Interchangeable Labeling Technology (Promega Corp., Madison Wis.) (see Table 2). These protocols are routine procedures well within the scope of one skilled in the art and from the teaching herein. A fluorophore binding protein can be operably-linked to a molecular feature comprising a polypeptide to create a fusion protein using standard molecular genetic techniques. Additionally, a fluorophore binding protein can be specifically linked to the amino or carboxyl-terminus of a molecular feature comprising a polypeptide using well known chemical methods, see, e.g., Chemical Approaches to Protein Engineering, in PROTEIN ENGINEERING: A PRACTICAL APPROACH (Eds. Rees et al., Oxford University Press, 1992).

TABLE 2

Excitation and Emission Maxima of Exemplary Fluorophores for Fluorophore Binding Proteins

| Name | Dye | Excitation maxima (nm) | Emission maxima (nm) |
| --- | --- | --- | --- |
| bis-Arsenical Tetracysteine System | | | |
| FlAsH | fluorescein arsenical hairpin binding dye | 508 | 528 |
| ReAsH | resorufin arsenical hairpin binding dye | 593 | 608 |
| AGT/SNAP-Tag System | | | |
| BG-430 | para-benzyl guanine diethylaminocoumarin | 421 | 444 and 484 |
| BG-DAF | para-benzyl guanine diacetylfluorescein | 500 | 524 |
| BG-505 | para-benzyl guanine dyomic DY-505-05 | 504 | 532 |
| BG-488 | para-benzyl guanine ATTO 488 | 506 | 526 |
| BG-532 | para-benzyl guanine ATTO 532 | 536 | 554 |
| BG-547 | para-benzyl guanine dyomic DY-547 | 554 | 568 |
| TMR-Star | para-benzyl guanine tetramethylrhodamine | 554 | 580 |
| BG-600 | para-benzyl guanine ATTO 600 | 606 | 626 |
| BG-632 | para-benzyl guanine dyomic DY-632 | 636 | 656 |
| BG-647 | para-benzyl guanine dyomic DY-647 | 660 | 673 |
| BG-732 | para-benzyl guanine dyomic DY-732 | 732 | 747 |
| BG-747 | para-benzyl guanine dyomic DY-747 | 752 | 763 |
| Dehalogenase/HaloTag ™ System | | | |
| HaloTag Coumarian | Coumarian derivative | 353 | 434 |
| HaloTag diAcFAM | nonfluorescent diacetyl fluorescein derivative | 494 | 526 |
| HaloTag TMR | tetramethyl rhodamine derivative | 555 | 585 |

Thus in an embodiment, a donor fluorophore or an acceptor fluorophore is a fluorophore binding protein which strongly interacts with a fluorophore. In another embodiment, a donor fluorophore or an acceptor fluorophore is a tetracysteine peptide which strongly interacts with a fluorophore. In aspects of this embodiment, a donor fluorophore or an acceptor fluorophore is a tetracysteine peptide which strongly interacts with a nonfluorescent biarsenical derivatives of fluorescein or a nonfluorescent biarsenical derivatives of resorufin. In another embodiment, a donor fluorophore or an acceptor fluorophore is an AGT polypeptide which strongly interacts with a fluorophore. In aspects of this embodiment, a donor fluorophore or an acceptor fluorophore is an AGT that strongly interacts with a para-substituted benzyl guanine derivative comprising a diethylaminocoumarin, a diacetylfluorescein, a dyomic DY-505-05, an ATTO 488, an ATTO 532, a DY-547, a tetramethylrhodamine, an ATTO 600, a dyomic DY-632, a dyomic DY-647, a dyomic DY-732 or a dyomic DY-747. In another embodiment, a donor fluorophore or an acceptor fluorophore is a dehalogenase polypeptide which strongly interacts with a fluorophore. In aspects of this embodiment, a donor fluorophore or an acceptor fluorophore is a dehalogenase that strongly interacts with a coumarian derivative such as HaloTag Coumarian, a fluorescein derivative such as HaloTag diAcFAM or a tetramethyl rhodamine derivative such as HaloTag TMR.

In another embodiment, both a donor fluorophore and an acceptor fluorophore can be a fluorophore binding protein which strongly interacts with a fluorophore. In another embodiment, both a donor fluorophore and an acceptor fluorophore can be a tetracysteine peptide which strongly interacts with a fluorophore. In aspects of this embodiment, both a donor fluorophore and an acceptor fluorophore can be a tetracysteine peptide which strongly interacts with a nonfluorescent biarsenical derivatives of fluorescein or a nonfluorescent biarsenical derivatives of resorufin. In another embodiment, both a donor fluorophore and an acceptor fluorophore can be an AGT polypeptide which strongly interacts with a fluorophore. In aspects of this embodiment, a both a donor fluorophore and an acceptor fluorophore can be an AGT that strongly interacts with a para-substituted benzyl guanine derivative comprising a diethylaminocoumarin, a diacetylfluorescein, a dyomic DY-505-05, an ATTO 488, an ATTO 532, a DY-547, a tetramethylrhodamine, an ATTO 600, a dyomic DY-632, a dyomic DY-647, a dyomic DY-732 or a dyomic DY-747. In another embodiment, both a donor fluorophore and an acceptor fluorophore can be a dehalogenase polypeptide which strongly interacts with a fluorophore. In aspects of this embodiment, both a donor fluorophore and an acceptor fluorophore can be a dehalogenase that strongly interacts with a coumarian derivative such as HaloTag Coumarian, a fluorescein derivative such as HaloTag diAcFAM or a tetramethyl rhodamine derivative such as HaloTag TMR.

A donor fluorophore or an acceptor fluorophore disclosed in the present specification can be, in part, a fluorescent dye. As used herein, the term "fluorescent dye" means a molecule which absorbs light energy of a certain wavelength, including, e.g., violet, blue, cyan, green, yellow-green, yellow, orange, red-orange, red, far-red or infrared, and emits light energy of a different wavelength and encompass those which emit in a variety of spectra, including violet, blue, cyan, green, yellow-green, yellow, orange, red-orange, red, far-red or infrared, see Table 3 for non-limiting examples. Non-limiting examples of a fluorescent dye include dyes derived from, e.g., a coumarin, a cyanine, a fluorescein, an isocyanate, an isothiocyanate, an indocarbocyanine, an indodicarbocyanine, a pyridyloxazole, a phycoerythrin, a phycocyanin, an o-phthaldehyde and a rhodamine. As another non-limiting example, a fluorescent dye can be a blue fluorescent dye, such as, e.g., 7-amino-4-methylcoumarin-3-acetic acid (AMCA), Cascade Blue, Alexa Fluor® 350 and Alexa Fluor® 405. As still another non-limiting example, a fluorescent dye can be a green fluorescent dye, such as, e.g., fluorescein, fluorescamine, carboxyfluorescein (FAM), fluorescein isothiocyanate (FITC), Cy2, BODIPY FL, BODIPY 493/503, BODIPY 499/508, Alexa Fluor® 488, Oregon Green® 488 and Alexa Fluor® 500. As yet another non-limiting example, a fluorescent dye can be a yellow-green fluorescent dye, such as, e.g., rhodamine 6G, BODIPY R6G, Alexa Fluor® 430 and Alexa Fluor® 514. As a further non-limiting example, a fluorescent dye can be a yellow fluorescent dye, such as, e.g., Lucifer Yellow, BODIPY 507/545, BODIPY 530/550, Alexa Fluor® 532. As a still further non-limiting example, a fluorescent dye can be an orange fluorescent dyes, such as, e.g., tetramethyl rhodamine (TAMRA), tetramethyl rhodamine-5-isothiocyanate (5-TRITC), tetramethyl rhodamine-6-isothiocyanate (6-TRITC), Cy3, BODIPY TMR, BODIPY 581/591, Alexa Fluor® 546. As a yet further non-limiting example, a fluorescent dye can be a red-orange fluorescent dye, such as, e.g., Lissamine Rhodamine B, Alexa Fluor® 555 and Alexa Fluor® 568. As another non-limiting example, a fluorescent dye can be a red fluorescent dye, such as, e.g., Texas Red, BODIPY TR, BODIPY 577/618, Alexa Fluor® 594 and Alexa Fluor® 610. As still another non-limiting example, a fluorescent dye can be a far-red fluorescent dye, such as, e.g., Cy5, BODIPY 630/650, BODIPY 650/665, Alexa Fluor® 633, Alexa Fluor® 635 and Alexa Fluor® 647; and near infrared fluorescent dyes, such as, e.g., allophycocyanin (APC), Cy5.5, Cy7, Alexa Fluor® 660, Alexa Fluor® 680, Alexa Fluor® 700 and Alexa Fluor® 750.

A fluorescent dye disclosed in the present specification can be attached to a molecular feature using standard conjugation chemistry methods known in the art, see, e.g., Richard P. Haugland, *A Guide to Fluorescent Probes and Labeling Technologies*, (Michelle T. Z. Spence ed., Invitrogen Corp., 10th ed., 2005). A variety of reactive groups can be used to couple a donor fluorophore or acceptor fluorophore to the desired position in a molecular feature disclosed in the present specification. One method of labeling a molecular feature disclosed in the present specification is to attach a fluorescent dye to a free amine group present in lysine residues and at the amino-terminus of a polypeptide. Another method of labeling a molecular feature disclosed in the present specification is to attach a fluorescent dye to a free reactive group present in nucleotides and at the 5'-terminus of a polynucleotide. Amine-reactive dyes are mostly acylating reagents that form carboxamides, sulfonamides or thioureas upon reaction with the amines. Reactive groups usually present on amine-reactive fluorescent dyes, include, without limitation, a succinimidyl ester group, a sulfosuccinimidyl ester group, a tetrafluorophenyl ester group, a carbonyl azide group, an isocyanate group, a sulfonyl chloride group or an aldehyde-containing group, such as, e.g., o-phthaldialdehyde (OPA), naphthalenedicarboxaldehyde (NDA) and 3-acylquinolinecarboxaldehyde (ATTO-TAG). Another method of labeling a molecular feature disclosed in the present specification is to attach a fluorescent dye to a free thiol group (also called mercaptans or sulfhydryls) present in cysteine residues of a polypeptide. Reactive groups usually present on thiol-reactive fluorescent dyes, include, without limitation, a maleimide group, an iodoacetamide group, a phenylmercury group, a thiosulfate group or a methyl bromide group. Yet another method of labeling a molecular disclosed in the present specification is to attach a fluorescent dye to a free carboxylic acid group. Reactive groups usually present on carboxylic acid-reactive fluorescent dyes, include, without limitation, a hydrazide group, a hydroxylamine group, a cadaverine group or an amine group. A fluorescent dye can also be attached using a cross-linker moiety, including, without limitation, homo- and hetero-bifunctional cross-linkers, such as, e.g., BMH and SPDP.

TABLE 3

Excitation and Emission Maxima of Exemplary Fluorescent Dyes

| Dye | Excitation maxima (nm) | Emission maxima (nm) |
|---|---|---|
| Alexa Fluor ® 350 | 346 | 440 |
| Alexa Fluor ® 405 | 402 | 421 |
| Alexa Fluor ® 430 | 430 | 540 |
| Alexa Fluor ® 488 | 495 | 519 |
| Alexa Fluor ® 500 | 503 | 525 |
| Alexa Fluor ® 514 | 518 | 540 |
| Alexa Fluor ® 532 | 532 | 553 |
| Alexa Fluor ® 546 | 556 | 575 |
| Alexa Fluor ® 555 | 555 | 565 |
| Alexa Fluor ® 568 | 578 | 603 |
| Alexa Fluor ® 594 | 590 | 617 |
| Alexa Fluor ® 610 | 612 | 628 |
| Alexa Fluor ® 633 | 632 | 647 |
| Alexa Fluor ® 647 | 650 | 665 |
| Alexa Fluor ® 660 | 663 | 690 |
| Alexa Fluor ® 680 | 679 | 702 |
| Alexa Fluor ® 700 | 696 | 719 |
| Alexa Fluor ® 750 | 749 | 775 |
| BODIPY FL | 505 | 513 |
| BODIPY TMR | 544 | 570 |

TABLE 3-continued

Excitation and Emission Maxima of Exemplary Fluorescent Dyes

| Dye | Excitation maxima (nm) | Emission maxima (nm) |
|---|---|---|
| BODIPY 493/503 | 493 | 503 |
| BODIPY 499/508 | 499 | 508 |
| BODIPY 507/545 | 508 | 543 |
| BODIPY 530/550 | 534 | 554 |
| BODIPY 577/618 | 577 | 618 |
| BODIPY 581/591 | 584 | 592 |
| BODIPY 630/650 | 625 | 640 |
| BODIPY 650/665 | 646 | 660 |
| Cy-2 | 492 | 510 |
| Cy-3 | 550 | 570 |
| Cy-5 | 650 | 670 |
| Cy-7 | 740 | 760 |
| Eosin | 524 | 544 |
| Fluo-4 | 494 | 516 |
| Fluorescein | 494 | 518 |
| Lucifer yellow | 426 | 531 |
| NBD | 478 | 541 |
| Oregon Green 488 | 496 | 524 |
| PyMPO | 415 | 570 |
| Rhodamine Red | 570 | 590 |
| Sulfonerhodamine | 555 | 580 |
| Tetramethylrhodamine | 555 | 580 |
| Texas Red | 595 | 615 |

Thus, in an embodiment, a donor fluorophore is a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye or an infrared fluorescent dye. In another embodiment, an acceptor fluorophore is a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye or an infrared fluorescent dye. In another embodiment, both a donor fluorophore and an acceptor fluorophore can be a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye or an infrared fluorescent dye.

Fluorophores useful in the invention include those having fluorescence lifetimes suitable for fluorescence polarization analysis. Preferably, donor fluorophores have a long fluorescence lifetime and preferably acceptor fluorophores have a short fluorescence lifetime. In aspects of the invention, a fluorophore can have, without limitation, a fluorescence lifetime of at least 0.1 nanoseconds, or at least 0.5 nanoseconds, or at least 5 nanoseconds, or at least 10 nanoseconds, or less than 100 nanoseconds or between about 0.1 and about 100 nanoseconds. Some fluorophores, particularly those such as certain metal chelates, and pyrene may have fluorescence lifetimes as long as 1-2 mseconds. See e.g., Joseph R. Lakowicz, PRINCIPLES OF FLUORESCENCE SPECTROSCOPY, (2d ed. Kluwer Academic/Plenum Publishers, New York 1999), hereby incorporated by reference.

In many aspects of the present invention, a difference in molar volume between donor and acceptor (or the molecular features associated with each) is not necessary. However, in some situations, a bulking group may enhance the detection of changes in proximity of two or more molecular features using DARET.

As used herein, the term "bulking group" means a moiety having sufficient hydrodynamic volume such that, upon dissociation of an acceptor-associated molecular feature from a donor-associated molecular feature to which the bulking group is joined, there is a change in polarization of at least 3 millipolarization units (mP). A variety of bulking groups may be useful in certain aspects of the methods of the invention, including, without limitation, fluorescent proteins such as green fluorescent protein.

In one embodiment, a method of the invention is practiced such that the change in molecular mass upon the molecular features going from an associated to an unassociated state is at least about 1000 Da or at least about 1500 Da or at least about 1700 Da. In a further embodiment, a method of the invention is practiced such that the change in fluorescence polarization is at least 5 millipolarization units (mP). In still a further embodiment, a method of the invention is practiced such that the change in fluorescence polarization is at least 15 mP.

Although the use of fluorescent protein bulking groups such as GFP is often convenient, bulking groups need not be fluorophores. Indeed, in aspects of the invention employing bulking groups, any of a variety of moieties can be useful as a bulking group in a method of the invention, including physical, chemical and biological moieties which can be covalently or non-covalently incorporated into or linked to the donor-associated molecular feature. When the present methodology is used as an assay of, for example, protease cleavage (and a bulking group is employed), the bulking group may be expressed as a fusion protein with another component of the protease substrate.

Bulking groups useful in such aspects of the present invention encompass natural and man-made moieties and further encompass, without limitation, inert moieties as well as those with biological or other activity. A bulking group useful in the invention can be, without limitation, an inert or active protein, peptide or peptidomimetic; an antibody; organic chemical; latex or other bead; or moiety such as streptavidin. Additional bulking groups useful in the invention encompass, without limitation, phage and other viruses; cells; liposomes; cellular membranes, polymeric and non-polymeric matrices; gold and other particles; and microdevices and nanodevices. As non-limiting examples, a bulking group useful in the invention can be a fluorescent protein such as GFP or BFP, or a fragment thereof; a protein useful for affinity purification such as glutathione-S-transferase (GST) or maltose-binding protein (MBP); or an antibody such as, without limitation, an anti-polyhistidine, an anti-FLAG, anti-hemagluttinin (HA) or anti-myc antibody. Streptavidin also can be a bulking group useful in the invention.

It is understood that molecular features useful in the invention optionally can include one or more additional components. As a non-limiting example, a flexible spacer sequence such as GGGGS (SEQ ID NO: 1) and EAAAK (SEQ ID NO. 2) can be included in a protease or other peptide substrate useful in the invention. A useful peptide substrate further can include, without limitation, one or more of the following: an affinity tag such as polyhistidine; biotin or a biotinylation sequence; or an epitope such as FLAG, hemagluttinin (HA), c-myc, or AU1; an immunoglobulin hinge region; an N-hydroxysuccinimide linker; a peptide or peptidomimetic hairpin turn; or a hydrophilic sequence or another component or sequence that, for example, facilitates purification or promotes the solubility or stability of the clostridial toxin substrate.

Conditions suitable for DARET assays generally must take place at temperatures in which at least one fluorophore-linked molecular feature is in the fluid phase. Thus, depending upon the characteristics of the fluid, such temperatures may even be less than 0° C., although in aqueous phases such temperatures are generally above zero, such as from about 4° C. to about 45° C. More commonly, the temperatures may be in the range of about 20° C. to about 45° C., for example, in the range of 25° C. to 40° C., or the range of 35° C. to 39° C. Assay volumes often are in the range of about 5 to about 200 µl, for example, in the range of about 10 µl to 100 µl or about 0.5 µl to 100 µl, although nanoliter reaction volumes also can be used with the methods of the invention. Assay volumes also can be, for example, in the range of 100 µl to 2.0 ml or in the range of 0.5 ml to 1.0 ml.

Assay times can be varied as appropriate by the skilled artisan and generally depend, in part, on the concentration, purity and activity of the molecular features. Assay times generally vary, without limitation, in the range of about instantaneous to about 5 hours. As non-limiting examples, exemplary assay times include incubation, for example, at 37° C. for 1 second, at 37° C. for 5 second, at 37° C. for 30 second, at 37° C. for 1 minute, at 37° C. for 5 minute, at 37° C. for 15 minute, at 37° C. for 30 minutes, 45 minutes, 60 minutes, 75 minutes or 90 minutes. In particular embodiments, such as those involving protease assays, the molecular features are at least 5%, 10%, 20%, 30%, 40%, 50%, 60%, 70%, 80%, 90%, 95% or 100% dissociated. For example a protease activity may be detected when the substrate is at least 5%, 10%, 20%, 30%, 40%, 50%, 60%, 70%, 80%, 90%, 95% or 100% cleaved. For example, a protease reaction based on a substrate containing GFP as the donor fluorophore can be terminated by the addition of guanidinium chloride, for example, to a final concentration of 1 to 2 M. Protease reactions also can be terminated by addition of $H_2SO_4$; addition of about 0.5 to 1.0 M sodium borate, pH 9.0 to 9.5; addition of zinc chelators, or addition of effective concentrations of a denaturant such as urea or guanidinium chloride. One skilled in the art understands that protease and other enzymatic reactions can be terminated, if desired, prior to exciting the fluorophore or donor fluorophore with plane polarized light.

As demonstrated above, it is understood that the methods of the invention can be automated and can be configured in a high-throughput or ultra high-throughput format using, without limitation, 96-well, 384-well or 1536-well plates. Any of a variety of spectrofluorometers equipped with an appropriate polarizer can be used to assay the change in fluorescence polarization over time including, without limitation, a Cary Eclipse spectrofluorometer; the SpectraMax M5 microplate reader and other systems from, for example, Perkin-Elmer.

In the methods of the invention, the change in fluorescence polarization can be an increase or decrease in fluorescence polarization. In one embodiment, the donor fluorophore has a fluorescence lifetime of at least 0.5 nanoseconds. In another embodiment, the donor fluorophore has a fluorescence lifetime of at least 5 nanoseconds. Fluorescence lifetimes may range from about 10 pseconds, or about 100 psec, or about 200 psec to about 10 µsec, or about 25 µsec, or about 50 µsec, or about 100 µsec or milliseconds. BFP and GFP have fluorescence lifetimes of about 4 nsec. Fluorescent metal chelates such as ruthenium, which emits polarized light, may have fluorescent lifetimes in the micro- to milliseconds.

In the DARET methods of the invention, an acceptor fluorophore useful in a clostridial toxin substrate has an absorbance spectrum that overlaps the emission spectrum of a donor fluorophore included in the substrate. An acceptor useful in the invention generally has rather low absorption at a wavelength suitable for excitation of the donor fluorophore.

As set forth above, an acceptor has an absorbance spectrum that overlaps the emission spectrum of the donor fluorophore. The term "overlapping," as used herein in reference to the absorbance spectrum of an acceptor and the emission spectrum of a donor fluorophore, means an absorbance spectrum and emission spectrum that are partly or entirely shared. Thus, in such overlapping spectra, the high end of the range of the donor fluorophore's emission spectrum is higher (i.e., has a longer wavelength) than the low end of the range of the acceptor's absorbance spectrum. Thus, whether a fluorophore is a donor or an acceptor depends on the spectral characteristics of the other fluorophore to which it is to be paired.

As set forth above, any of a variety of donor fluorophores and acceptor fluorophores can be useful in the invention, including, without limitation, a fluorescent protein, such as, e.g., a BFP, a CFP, a GFP, a YFP and a RFP; a fluorophore binding protein which strongly interacts with a fluorophore, such as, e.g., a tetracysteine, a AGT polypeptide or a dehalogenase; and a fluorescent dye, such as, e.g., a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye or an infrared fluorescent dye.

Exemplary donor fluorophore-acceptor pairs which exhibit DARET and are useful in the methods of the invention encompass, without limitation, GFP and BFP, GFP and Alexa Fluor® 546; fluorescein and tetramethylrhodamine; Dansyl and octadecylrhodamine (Table 4). Other known DARET pairs include, without limitation,

TABLE 4

Exemplary DARET Donor Fluorophore-Acceptor Fluorophore Pairs

| Donor | Acceptor |
| --- | --- |
| Alexa Fluor ® 350 | Alexa Fluor ® 488 |
| Alexa Fluor ® 488 | Alexa Fluor ® 546, Alexa Fluor ® 555, Alexa Fluor ® 568, Alexa Fluor ® 594, Alexa Fluor ® 647 |
| Alexa Fluor ® 546 | Alexa Fluor ® 568, Alexa Fluor ® 594, Alexa Fluor ® 647 |
| Alexa Fluor ® 555 | Alexa Fluor ® 594, Alexa Fluor ® 647 |
| Alexa Fluor ® 568 | Alexa Fluor ® 647 |
| Alexa Fluor ® 594 | Alexa Fluor ® 647 |
| fluorescein | Fluorescein |
| IAEDANS | Fluorescein |
| EDANS | Dabsyl |
| BODIPY FL | BODIPY FL |

One skilled in the art understands that the listed donor fluorophores and other donor fluorophores suitable for DARET can be paired with any of a variety of acceptors having an absorbance spectrum that overlaps the emission spectrum of the donor fluorophore.

As described above, recombinant methods may in particular cases be used to produce one or more molecular features according to the present invention. Additionally, a donor and/or acceptor fluorophore may comprise a fluorescent protein or a fluorescent binding protein, and may be linked to a molecular feature by way of a peptide bond. Alternatively, a cysteine or other reactive moiety may be incorporated and used for attachment of a fluorophore to a proteinacious recombinant molecular feature. In other embodiments, fluorophores may be conjugated to proteins using, for example, a bifunctional reagent or linker.

Chemical methods for modifying a protein, peptide or peptidomimetic to contain a fluorophore and/or bulking group, or a donor fluorophore and acceptor, are well known in the art (Fairclough and Cantor, *Methods Enzymol.* 48:347-379 (1978); Glaser et al., *Chemical Modification of Proteins*

Elsevier Biochemical Press, Amsterdam (1975); Haugland, *Excited States of Biopolymers* (Steiner Ed.) pp. 29-58, Plenum Press, New York (1983); Means and Feeney, *Bioconjugate Chem.* 1:2-12 (1990); Matthews et al., *Methods Enzymol.* 208:468-496 (1991); Lundblad, *Chemical Reagents for Protein Modification* 2nd Ed., CRC Press, Boca Ratan, Fla. (1991); Haugland, supra, 1996). A variety of groups can be used to couple a bulking group (if employed), donor fluorophore and/or acceptor fluorophore, for example, to a peptide or peptidomimetic. A thiol group, for example, can be used to couple a fluorophore, bulking group, donor fluorophore or acceptor to the desired position in a peptide or peptidomimetic to produce a labeled molecular feature according to the present invention. Haloacetyl and maleimide labeling reagents also can be used to couple a fluorophore, bulking group, donor fluorophore and/or acceptor in preparing a molecular feature useful in the invention. See, for example, Wu and Brand, supra, 1994.

Cross-linker moieties also can be useful for preparing a fluorophore-labeled molecular feature. Cross-linkers are well known in the art and include homo- and hetero-bifunctional cross-linkers such as BMH and SPDP. Where a fluorophore, bulking group, donor fluorophore and/or acceptor is a protein, well-known chemical methods for specifically linking molecules to the amino- or carboxy-terminus of a protein can be employed. See, for example, "Chemical Approaches to Protein Engineering" in *Protein Engineering: A Practical Approach* Rees et al. (Eds) Oxford University Press, 1992.

Where a protease assay is designed for DARET in accordance with the present invention, the protease substrate contains a donor fluorophore and an acceptor, the protease cleavage site is positioned between the donor fluorophore and the acceptor fluorophore. In one embodiment, the donor fluorophore is positioned amino-terminal of the cleavage site while the acceptor is positioned carboxy-terminal of the cleavage site. In another embodiment, the donor fluorophore is positioned carboxy-terminal of the cleavage site while the acceptor is positioned amino-terminal of the cleavage site.

One skilled in the art understands that there are several considerations in selecting and positioning a bulking group (if such is to be used), a donor fluorophore and an acceptor fluorophore, in a manner useful in the invention. The donor fluorophore and acceptor fluorophore, generally are positioned to minimize interference with binding or interaction between molecular features. Thus, a donor fluorophore and acceptor, can be selected and positioned, for example, so as to minimize the disruption of bonded and non-bonded interactions that are important for binding, and to minimize steric hindrance. In addition, as discussed further below, the spatial distance between an acceptor and donor fluorophore generally is limited to achieve efficient energy transfer from the donor fluorophore to the acceptor—and such distance should be within the range between about 5 Å and about 100 Å, preferably between about 10 Å and about 50 Å, or about 10 Å and about 30 Å, or about 30 Å and about 100 Å, or about 70 Å and about 100 Å.

As discussed above, efficiency of energy transfer from a donor fluorophore to an acceptor is dependent, in part, on the spatial separation of the donor fluorophore and acceptor molecule. As the distance between the donor fluorophore and acceptor increases (and/or the dipole orientation varies), there is less energy transfer to the acceptor, and the donor fluorescence signal therefore increases. The overall energy transfer between the donor fluorophore and acceptor is dependent upon many factors, including the separation distance between the donor fluorophore and acceptor, the spectral overlap between donor fluorophore and acceptor, and the relative dipole orientations of the donor and acceptor. One skilled in the art understands that, as the concentration of the molecular features increases, intermolecular quenching of the donor can become a factor. This phenomenon is denoted the "inner filter effect." One skilled in the art further understands that the concentration of substrate can be controlled to minimize this.

The Förster distance, which is the separation between a donor fluorophore and an acceptor yielding 50% non-radiative energy transfer, represents a spatial separation between donor fluorophore and acceptor that provides a good sensitivity. For peptide substrates, adjacent residues are separated by a distance of approximately 3.6 Å in the most extended conformation. For example, the calculated Förster distance for a fluorescein/tetramethylrhodamine pair is 55 Å, which would represent a spatial separation between fluorescein and tetramethylrhodamine of about 15 amino acid residues in the most extended conformation. Because peptides and peptidomimetics in solution rarely have a fully extended conformation, and are capable of substantial flexibility, donor fluorophores and acceptors can be more widely separated than expected based on a calculation performed using a distance of 3.6 Å per residue and still remain within the Förster distance. This is shown, for example, by the occurrence of FRET between donor-acceptor pairs separated by about 50 amino acids (Graham et al., *Anal. Biochem.* 296: 208-217 (2001)).

Förster theory is based on very weak interactions between a donor fluorophore and an acceptor; spectroscopic properties such as absorption of one fluorophore should not be altered in the presence of the other, defining the shortest distance range over which the theory is valid. It is understood that, for many donor fluorophore-acceptor pairs, Förster theory is valid when donor fluorophores and acceptors are separated by about 10 Å to 100 Å. However, for particular donor fluorophore-acceptor pairs, Förster theory is valid at distances below 10 Å (such as 5 Å or less) as determined by subpicosecond techniques (Kaschke and Ernsting, *Ultrafast Phenomenon in Spectroscopy* (Klose and Wilhelmi (Eds.)) Springer-Verlag, Berlin 1990).

The Förster equation for $R_0$, the Förster radius, is: $R_0 = [8.8 \times 10^{23} * \kappa^2 * n^4 * QY_D * J(\lambda)]^{1/6}$ Angstroms, where $\kappa^2$ is the dipole orientation factor (range from 0 to 4; $2/3$ for randomly oriented donors and acceptors; $QY_D$ is the fluorescence quantum yield of the donor in the absence of the acceptor; n is the refractive index, $J(\lambda)$ is the spectral overlap integral $\int \epsilon_A(\lambda) \cdot F_D (\lambda) \cdot \lambda^4 d\lambda$ cm$^3$M$^{-1}$, where $\epsilon_A$ is the extinction coefficient of acceptor; and $F_D$ is the fluorescence coefficient intensity of the donor expressed as a fraction of the total integrated intensity.

In particular embodiments, the invention provides a method for determining the proximity of molecular features in which the donor fluorophore is separated from the acceptor by a distance of at most about 100 Å. In other embodiments, the invention provides a method for determining the proximity of molecular features in which the donor fluorophore is separated from the acceptor by a distance of at most 90 Å, 80 Å, 70 Å, 60 Å, 50 Å, 40 Å, 30 Å, 20 Å, 10 Å, or 5 Å. In further embodiments, the invention provides a method for determining the proximity of molecular features in which the donor fluorophore is separated from the acceptor by a distance of 5 Å to 100 Å, 10 Å to 80 Å, 10 Å to 60 Å, 10 Å to 40 Å, 10 Å to 20 Å, 20 Å to 100 Å, 20 Å to 80 Å, 20 Å to 60 Å, 20 Å to 40 Å, 40 Å to 100 Å, 40 Å to 80 Å or 40 Å to 60 Å. In still further embodiments, the invention provides a method for determining the proximity of molecular features between proteins, or regions of a protein, in which the donor fluorophore and the acceptor are separated by at most six amino acid residues, at most eight residues, at most ten residues, at most twelve residues, at most fifteen residues, at most twenty residues, at most twenty-five residues, at most thirty residues, at most thirty-five residues, at most forty residues, at most forty-five residues, at most fifty residues, at most sixty residues, at most seventy residues, at most eighty residues, at most ninety residues, at most 100 residues, at most 150 residues, or at most 200 residues. It is understood that molecular features may be associated with widely distant amino acid residues but may nevertheless be in proximity due to conformational folding.

When attempting to determine the proximity of molecular features within a single molecule, such as in a protease assay, or when detecting changes in conformation of a protein, one skilled in the art understands that a peptide substrate useful in the invention can be designed, if desired, to optimize the efficiency of DARET. One skilled in the art understands that a donor fluorophore can be selected, if desired, with a high quantum yield, and an acceptor can be selected, if desired, with a high extinction coefficient to maximize the Förster distance. One skilled in the art further understands that fluorescence arising from direct excitation of an acceptor can be difficult to distinguish from fluorescence resulting from resonance energy transfer. Thus, it is recognized that a donor fluorophore and acceptor can be selected which have relatively little overlap of their excitation spectra such that the donor can be excited at a wavelength that results in minimal direct excitation of the acceptor. It further is recognized that a substrate containing molecular features and a donor and acceptor fluorophore useful in the invention can be designed so that the emission spectra of the donor fluorophore and acceptor overlap relatively little such that the two emissions can be readily distinguished.

A substrate, such as a substrate containing a protease cleavage site, a phosphorylation site (or both), or two or more molecular features whose proximity is to be determined, can have one or multiple modifications as compared to a naturally occurring molecule. As an example, such a molecule can be a fusion protein comprising either one or two fluorescent protein moieties. Additionally, such a molecule can be made to contain one or more amino acid residues able to form a linkage to a fluorophore, either directly or through a linker. In one embodiment, such a residue is a cysteine residue.

As used herein, the term "peptidomimetic" is used broadly to mean a peptide-like molecule that is able to serve as a model for a peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an $N^\alpha$-$C^\alpha$ cyclized amino acid; an $N^\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an $NC^\delta$ or $C^\alpha$-$C^\delta$ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein. The term "polypeptide" shall include peptidomimetics unless expressly indicated otherwise.

Example 1

BoNT-A DARET Assay

GFP/Alexa Fluor 546-Labeled Substrate

As an example of one aspect of the present invention, the molecular features whose proximity was to be determined comprised a) the amino terminal portion and b) the carboxyl terminal portion of a template comprising the recognition and cleavage site (contained in residues 134-206) of the SNARE protein SNAP-25 by *C. botulinum* type A neurotoxin (BONT-A) and located between these two molecular features.

Vector pQBI GFP-SNAP25(134-206) comprises a nucleic acid region encoding a GFP-SNAP-25 fusion protein. This vector was constructed as follows in two phases: First, vector pQBI T7-GFP was PCR-modified to remove the stop codon at the 3' terminus of the GFP-coding sequence and to insert the coding sequence for a portion of the peptide linker separating GFP from the SNAP-25 fragment. Second, a DNA fragment coding for SNAP-25 (134-206) was PCR amplified from pQE50/BirASNAP (128-206). The PCR primers were designed to incorporate the coding sequence for the remainder of the peptide linker fused 5' to the SNAP-25(134-206) gene and a 6×His affinity tag fused 3' of the gene. The resultant PCR product was cloned into the modified pQBI vector to yield the desired pQBI GFP-SNAP25(134-206) plasmid.

This vector was modified to create two derivative vectors having newly-incorporated cysteine residues at different locations in order to place a second fluorophore, Alexa Fluor® 546, on the carboxyl terminal side of the BONT-A cleavage site. In the first such construct, the cysteine was placed as the last C-terminal residue of the fusion protein, and in the second construct, the cysteine was placed between the SNAP-25 sequence and the HIS6 tag. These constructs were termed pQBI GFP-SNAP25(Cys-Stop) and pQBI GFP-SNAP25 (Cys-6His).

Vector pQBI GFP-SNAP25(134-206) was subjected to 2 separate polymerase chain reactions (PCR) to create the constructs mentioned above using primers Cys-Stop and Cys-6His along with their complementary sequences as "opposite strand" primers.

```
Primer Cys-Stop (SEQ ID NO: 3):
5'-GTTATTGCTCAGCTTTAGCAGTGATGGTGATGGTG-3'

Primer Cys-6His (SEQ ID NO: 4):
5'-GATGGTGATGGTGATGACAGCCGCCACCGCCACC-3'
```

Six 50 µL PCR reactions were assembled for each pair of primers. Every reaction contained the following PCR buffer: 5 µL 10× Pfu Buffer (Stratagene), 1 µL dNTPs (12.5 mM each; Promega), 1 µL Pfu Turbo DNA polymerase (Stratagene; hot start addition), template DNA (20, 30, or 40 ng pQBI GFP-SNAP25(134-206), and each primer of the appropriate pair at a final concentration of 0.2 µM. The reaction mixtures were brought to a final volume of 50 µL with nuclease-free water, and the samples incubated according to the following thermocycler conditions:

| Step 1 | 95° C.       | 2 min   |
|--------|--------------|---------|
| Step 2 | 95° C.       | 1 min   |
| Step 3 | 50 or 55° C. | 30 sec  |
| Step 4 | 72° C.       | 12 min  |
| Step 5 | 72° C.       | 7 min   |
| Step 6 | 10° C.       | Hold    |

Steps 2-4 were repeated 25 times, before proceeding to Steps 5 and 6. Following thermocycling, 1 µL Dpn I restriction enzyme (Stratagene) was added to each reaction and incubated for 1 h 15 minutes at 37° C. to digest template DNA. The reactions were purified by QIAquick kit (Qiagen) and analyzed by agarose gel electrophoresis. All but two of the reactions produced full-length plasmid. Sequencing of candidate plasmids identified one plasmid of each type containing the desired change, and these two samples were selected to proceed with.

The first plasmid contained a open reading frame containing the nucleotide sequences coding for the GFP/SNAP-25 fusion protein, in which the cysteine was incorporated as the last C-terminal residue. This amino acid and corresponding nucleotide sequence is set forth below and as sequences SEQ ID NO: 5 and SEQ ID NO: 6, respectively.

```
                                  GFP
~~~~~~~~~~~~~~~~~~~~~~~~~~~~~~~~~~~~~~~~~~~~~~~~~~~~~~~~~~~~~~~~~~~~~~~~
    M    A    S    K    G    E    E    L    F    T    G    V    V    P    I    L    V    E    L    D    G
ATGGCTAGC AAAGGAGAA GAACTCTTC ACTGGAGTT GTCCCAATT CTTGTTGAA TTAGATGGT

GFP
~~~~~~~~~~~~~~~~~~~~~~~~~~~~~~~~~~~~~~~~~~~~~~~~~~~~~~~~~~~~~~~~~~~~~~~~
    D    V    N    G    H    K    F    S    V    S    G    E    G    E    G    D    A    T    Y    G    K
GATGTTAAC GGCCACAAG TTCTCTGTC AGTGGAGAG GGTGAAGGT GATGCAACA TACGGAAAA

GFP
~~~~~~~~~~~~~~~~~~~~~~~~~~~~~~~~~~~~~~~~~~~~~~~~~~~~~~~~~~~~~~~~~~~~~~~~
    L    T    L    K    F    I    C    T    T    G    K    L    P    V    P    W    P    T    L    V    T
CTTACCCTG AAGTTCATC TGCACTACT GGCAAACTG CCTGTTCCA TGGCCAACA CTAGTCACT

GFP
~~~~~~~~~~~~~~~~~~~~~~~~~~~~~~~~~~~~~~~~~~~~~~~~~~~~~~~~~~~~~~~~~~~~~~~~
    T    L    C    Y    G    V    Q    C    F    S    R    Y    P    D    H    M    K    R    H    D    F
ACTCTGTGC TATGGTGTT CAATGCTTT TCAAGATAC CCGGATCAT ATGAAACGG CATGACTTT

GFP
~~~~~~~~~~~~~~~~~~~~~~~~~~~~~~~~~~~~~~~~~~~~~~~~~~~~~~~~~~~~~~~~~~~~~~~~
    F    K    S    A    M    P    E    G    Y    V    Q    E    R    T    I    F    F    K    D    D    G
TTCAAGAGT GCCATGCCC GAAGGTTAT GTACAGGAA AGGACCATC TTCTTCAAA GATGACGGC

GFP
~~~~~~~~~~~~~~~~~~~~~~~~~~~~~~~~~~~~~~~~~~~~~~~~~~~~~~~~~~~~~~~~~~~~~~~~
    N    Y    K    T    R    A    E    V    K    F    E    G    D    T    L    V    N    R    I    E    L
AACTACAAG ACACGTGCT GAAGTCAAG TTTGAAGGT GATACCCTT GTTAATAGA ATCGAGTTA

GFP
~~~~~~~~~~~~~~~~~~~~~~~~~~~~~~~~~~~~~~~~~~~~~~~~~~~~~~~~~~~~~~~~~~~~~~~~
    K    G    I    D    F    K    E    D    G    N    I    L    G    H    K    L    E    Y    N    Y    N
AAAGGTATT GACTTCAAG GAAGATGGC AACATTCTG GGACACAAA TTGGAATAC AACTATAAC

GFP
~~~~~~~~~~~~~~~~~~~~~~~~~~~~~~~~~~~~~~~~~~~~~~~~~~~~~~~~~~~~~~~~~~~~~~~~
    S    H    N    V    Y    I    M    A    D    K    Q    K    N    G    I    K    V    N    F    K    T
TCACACAAT GTATACATC ATGGCAGAC AAACAAAAG AATGGAATC AAAGTGAAC TTCAAGACC

GFP
~~~~~~~~~~~~~~~~~~~~~~~~~~~~~~~~~~~~~~~~~~~~~~~~~~~~~~~~~~~~~~~~~~~~~~~~
    R    H    N    I    E    D    G    S    V    Q    L    A    D    H    Y    Q    Q    N    T    P    I
CGCCACAAC ATTGAAGAT GGAAGCGTT CAACTAGCA GACCATTAT CAACAAAAT ACTCCAATT

GFP
~~~~~~~~~~~~~~~~~~~~~~~~~~~~~~~~~~~~~~~~~~~~~~~~~~~~~~~~~~~~~~~~~~~~~~~~
    G    D    G    P    V    L    L    P    D    N    H    Y    L    S    T    Q    S    A    L    S    K
GGCGATGGC CCTGTCCTT TTACCAGAC AACCATTAC CTGTCCACA CAATCTGCC CTTTCGAAA

GFP
~~~~~~~~~~~~~~~~~~~~~~~~~~~~~~~~~~~~~~~~~~~~~~~~~~~~~~~~~~~~~~~~~~~~~~~~
    D    P    N    E    K    R    D    H    M    V    L    L    E    F    V    T    A    A    G    I    T
GATCCCAAC GAAAAGAGA GACCACATG GTCCTTCTT GAGTTTGTA ACAGCTGCT GGGATTACA
```

```
                                    Linker
                   ~~~~~~~~~~~~~~~~~~~~~~~~~~~~~~~~~~~~~~
          GFP
~~~~~~~~~~~~~~~~~~~~~~~~                                        ~~~~~~~~~~
  H   G   M   D   E   L   Y   N   G   G   A   G   S   G   A   G   G   G   G   I   R
CATGGCATG GATGAACTG TACAACGGC GGTGCAGGA TCCGGTGCG GGTGGCGGT GGCATCCGG SNAP25 (134-206)
          ~~~~~~~~~~~~~~~~~~~~~~~~~~~~~~~~~~~~~~~~~~~~~~~~~~~~~~~
  R   V   T   N   D   A   R   E   N   E   M   D   E   N   L   E   Q   V   S   G   I
AGGGTAACA AACGATGCC CGGGAAAAT GAGATGGAT GAGAACCTG GAGCAGGTG AGCGGCATC SNAP25 (134-206)
          ~~~~~~~~~~~~~~~~~~~~~~~~~~~~~~~~~~~~~~~~~~~~~~~~~~~~~~~
  I   G   N   L   R   H   M   A   L   D   M   G   N   E   I   D   T   Q   N   R   Q
ATCGGAAAC CTCCGCCAT ATGGCTCTA GACATGGGC AATGAGATT GACACCCAG AATCGCCAG SNAP25 (134-206)
          ~~~~~~~~~~~~~~~~~~~~~~~~~~~~~~~~~~~~~~~~~~~~~~~~~~~~~~~
  I   D   R   I   M   E   K   A   D   S   N   K   T   R   I   D   E   A   N   Q   R
ATCGACAGG ATCATGGAG AAGGCTGAT TCCAACAAA ACCAGAATT GATGAAGCC AACCAACGT Linker                                    Cys
    SNAP25 (134-206)      ~~~~~~~~~~~~      6xHis Tag              ~~~
~~~~~~~~~~~~~~~~~~~~~~    ~~~~~~~~~~    ~~~~~~~~~~~~~~~~~~~~
  A   T   K   M   L   G   S   G   G   G   G   G   H   H   H   H   H   H   C   *
GCAACAAAG ATGCTGGGA AGTGGTGGC GGTGGCGGC CATCACCAT CACCATCAC TGCTAA
```

The second plasmid contained an open reading frame containing the nucleotide sequences coding for the GFP/SNAP-25 fusion protein, in which the cysteine was incorporated between the HIS6 tag and the SNAP-25 region. This amino acid and corresponding nucleotide sequence is set forth below and as sequences SEQ ID NO: 7 and SEQ ID NO: 8, respectively.

```
                              GFP
          ~~~~~~~~~~~~~~~~~~~~~~~~~~~~~~~~~~~~~~~~~~~~~~~~~~~~~~~~~~~~
  M   A   S   K   G   E   E   L   F   T   G   V   V   P   I   L   V   E   L   D   G
ATGGCTAGC AAAGGAGAA GAACTCTTC ACTGGAGTT GTCCCAATT CTTGTTGAA TTAGATGGT

GFP
          ~~~~~~~~~~~~~~~~~~~~~~~~~~~~~~~~~~~~~~~~~~~~~~~~~~~~~~~~~~~~
  D   V   N   G   H   K   F   S   V   S   G   E   G   E   G   D   A   T   Y   G   K
GATGTTAAC GGCCACAAG TTCTCTGTC AGTGGAGAG GGTGAAGGT GATGCAACA TACGGAAAA

GFP
          ~~~~~~~~~~~~~~~~~~~~~~~~~~~~~~~~~~~~~~~~~~~~~~~~~~~~~~~~~~~~
  L   T   L   K   F   I   C   T   T   G   K   L   P   V   P   W   P   T   L   V   T
CTTACCCTG AAGTTCATC TGCACTACT GGCAAACTG CCTGTTCCA TGGCCAACA CTAGTCACT

GFP
          ~~~~~~~~~~~~~~~~~~~~~~~~~~~~~~~~~~~~~~~~~~~~~~~~~~~~~~~~~~~~
  T   L   C   Y   G   V   Q   C   F   S   R   Y   P   D   H   M   K   R   H   D   F
ACTCTGTGC TATGGTGTT CAATGCTTT TCAAGATAC CCGGATCAT ATGAAACGG CATGACTTT

GFP
          ~~~~~~~~~~~~~~~~~~~~~~~~~~~~~~~~~~~~~~~~~~~~~~~~~~~~~~~~~~~~
  F   K   S   A   M   P   E   G   Y   V   Q   E   R   T   I   F   F   K   D   D   G
TTCAAGAGT GCCATGCCC GAAGGTTAT GTACAGGAA AGGACCATC TTCTTCAAA GATGACGGC

GFP
          ~~~~~~~~~~~~~~~~~~~~~~~~~~~~~~~~~~~~~~~~~~~~~~~~~~~~~~~~~~~~
  N   Y   K   T   R   A   E   V   K   F   E   G   D   T   L   V   N   R   I   E   L
AACTACAAG ACACGTGCT GAAGTCAAG TTTGAAGGT GATACCCTT GTTAATAGA ATCGAGTTA

GFP
          ~~~~~~~~~~~~~~~~~~~~~~~~~~~~~~~~~~~~~~~~~~~~~~~~~~~~~~~~~~~~
  K   G   I   D   F   K   E   D   G   N   I   L   G   H   K   L   E   Y   N   Y   N
AAAGGTATT GACTTCAAG GAAGATGGC AACATTCTG GGACACAAA TTGGAATAC AACTATAAC

GFP
          ~~~~~~~~~~~~~~~~~~~~~~~~~~~~~~~~~~~~~~~~~~~~~~~~~~~~~~~~~~~~
  S   H   N   V   Y   I   M   A   D   K   Q   K   N   G   I   K   V   N   F   K   T
TCACACAAT GTATACATC ATGGCAGAC AAACAAAAG AATGGAATC AAAGTGAAC TTCAAGACC

GFP
          ~~~~~~~~~~~~~~~~~~~~~~~~~~~~~~~~~~~~~~~~~~~~~~~~~~~~~~~~~~~~
  R   H   N   I   E   D   G   S   V   Q   L   A   D   H   Y   Q   Q   N   T   P   I
CGCCACAAC ATTGAAGAT GGAAGCGTT CAACTAGCA GACCATTAT CAACAAAAT ACTCCAATT
```

```
                                GFP
      ┌─────────────────────────────────────────────────────────────────┐
       G   D   G   P   V   L   L   P   D   N   H   Y   L   S   T   Q   S   A   L   S   K
      GGCGATGGC CCTGTCCTT TTACCAGAC AACCATTAC CTGTCCACA CAATCTGCC CTTTCGAAA

GFP
      ┌─────────────────────────────────────────────────────────────────┐
       D   P   N   E   K   R   D   H   M   V   L   L   E   F   V   T   A   A   G   I   T
      GATCCCAAC GAAAAGAGA GACCACATG GTCCTTCTT GAGTTTGTA ACAGCTGCT GGGATTACA

Linker
                  GFP                      ┌─────────────────────────────┐
      ┌──────────────────────────────────┐                                ┌─────────┐
       H   G   M   D   E   L   Y   N   G   G   A   G   S   G   A   G   G   G   I   R
      CATGGCATG GATGAACTG TACAACGGC GGTGCAGGA TCCGGTGCG GGTGGCGGT GGCATCCGG SNAP25 (134-206)
      ┌─────────────────────────────────────────────────────────────────┐
       R   V   T   N   D   A   R   E   N   E   M   D   E   N   L   E   Q   V   S   G   I
      AGGGTAACA AACGATGCC CGGGAAAAT GAGATGGAT GAGAACCTG GAGCAGGTG AGCGGCATC SNAP25 (134-206)
      ┌─────────────────────────────────────────────────────────────────┐
       I   G   N   L   R   H   M   A   L   D   M   G   N   E   I   D   T   Q   N   R   Q
      ATCGGAAAC CTCCGCCAT ATGGCTCTA GACATGGGC AATGAGATT GACACCCAG AATCGCCAG SNAP25 (134-206)
      ┌─────────────────────────────────────────────────────────────────┐
       I   D   R   I   M   E   K   A   D   S   N   K   T   R   I   D   E   A   N   Q   R
      ATCGACAGG ATCATGGAG AAGGCTGAT TCCAACAAA ACCAGAATT GATGAAGCC AACCAACGT SNAP25 (134-206)                      Cys
      ┌──────────────────────┐   Linker      ┌───┐      6xHis Tag
                              ┌─────────────┐      ┌──────────────────────┐
       A   T   K   M   L   G   S   G   G   G   G   G   C   H   H   H   H   H   *
      GCAACAAAG ATGCTGGGA AGTGGTGGC GGTGGCGGC TGTCATCAC CATCACCAT CACTAA
```

Plasmids pQBI GFP-SNAP25(Cys-Stop) and pQBI GFP-SNAP25(Cys-6His) were transformed into *E. coli* BL21-CodonPlus® (DE3)-RIL cells (obtained from Stratagene, Inc.) containing the T7 RNA polymerase gene. The transformed cells were spread onto Luria broth plates containing ampicillin (100 µg/ml) and incubated overnight at 37° C. Single colonies were used to inoculate 2-mL Luria broth+ampicillin (LB+amp) cultures, and 1 ml from each of these cultures was in turn used to inoculate a 500 mL LB+amp culture of each type.

These larger cultures were grown at 37° C. with shaking until the $A_{595}$ reached 0.5-0.6 absorbance units, at which time they were removed from the incubator and were allowed to cool. Protein expression, under inductive control of the lac repressor was induced by the addition of Isopropyl-β-D-thiogalactopyranoside (IPTG) to a final concentration of 1 mM and the cultures were incubated overnight at 16° C. with shaking. Cells from 250 mL aliquots of each culture were collected by centrifugation (6,000×g, 15 min, 4° C.) and stored at −80° C., unless the protein was to be purified immediately. The fusion proteins were purified as described below.

All purification steps were undertaken at 4° C. The cell pellet from each 250 mL culture was resuspended in 10 mL Fusion Protein Column Binding Buffer (25 mM HEPES, pH 8.0; 500 mM NaCl; 1 mM □-mercaptoethanol; 10 mM imidazole) to which had been added 100 µL (10 µL/mL) Protease Inhibitor Cocktail Set III (Calbiochem). The cells were lysed by sonication (1 minute 40 seconds in 10-sec pulses at 38% amplitude) and clarified by centrifugation (16,000 rpm, 4° C., 45 min). Affinity resin (8 mL Talon® SuperFlow Co$^{2+}$, B-D Biosciences) was equilibrated in 20 mL column supports (Bio-Rad) by rinsing with 8 column volumes of ddH$_2$O and 8 column volumes of Fusion Protein Column Binding Buffer. The clarified lysates were added to the resin and batch-bound by horizontal incubation for 1-1.5 h with gentle rocking. Following batch-binding, the columns were righted and the solutions drained, collected, and passed over the resin beds again. The columns were then washed with 8 column volumes of Fusion Protein Column Wash Buffer (25 mM HEPES, pH8.0; 500 mM NaCl; 1 mM □-mercaptoethanol; 20 mM imidazole) and proteins eluted with 15 mL Fusion Protein Column Elution Buffer (25 mM HEPES, pH 8.0; 500 mM NaCl; 1 mM □-mercaptoethanol; 500 mM imidazole), which was collected in fractions of ~1.4 mL. The green fractions were combined for each protein and concentrated to a total volume less than 5 mL in an Apollo 20-mL concentrator (QMWL 25 kDa, Orbital Biosciences). The proteins were then desalted by FPLC (BioRad Biologic DuoLogic, QuadTec UV-V is detector) with a HiPrep 26/10 size exclusion column (Pharmacia) and an isocratic mobile phase of chilled Fusion Protein Desalting Buffer (50 mM HEPES, pH 7.2, 4° C.) at a flow rate of 10 mL/min. The desalted proteins were collected as a single fraction and the concentration determined by BioRad Protein Assay. The protein solutions were divided into 500 µL aliquots, flash-frozen with liquid N$_2$ and stored at −80° C. Once defrosted, working aliquots are stored at 4° C., protected from light.

Alexa Fluor™ 546 was chosen as a complementary fluorophore capable of exhibiting DARET with GFP. Alexa Fluor™ 546 C$_5$ maleimide is a derivative of Alexa Fluor 546 comprising a linker designed to couple with, e.g., the free sulfhydryl groups of cysteine residues. The structure of Alexa Fluor™ 546 C$_5$ maleimide is shown below:

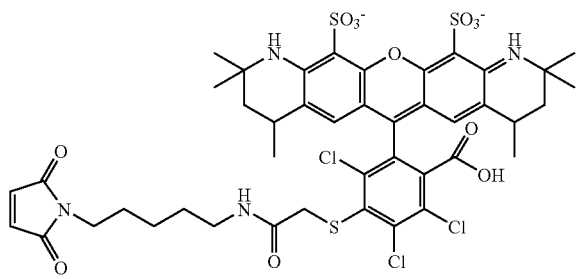

All reagents, buffers, and reactions were kept at 4° C. Four microliters of a 10 mM aqueous solution of Alexa 546 $C_5$ maleimide (MW 1,034.37; Molecular Probes) were added to 200 µL of GFP-SNAP25(Cys-Stop) (135 µM in 25 mM HEPES buffer, pH 7.2) and to a 200 µL solution of GFP-SNAP25(Cys-6His) (135 µM in 25 mM HEPES buffer, pH 7.2), mixed well, and incubated at 4° C. overnight. The reactions were transferred to Biomax Ultrafree centrifugal filters (30 KDa NMWL, Millipore), concentrated, and then concentrated two additional times from 25 mM HEPES, pH 7.2, to remove most of the excess unreacted Alexa Fluor 546. To remove the remaining unreacted Alexa 546, the concentrated solutions were transferred to Spin Microdialyzers (Harvard Apparatus) and each was dialyzed against 500 mL 20 mM HEPES, pH 6.9, for 1 h, and against 3×250 mL of that buffer for ~1.5 h each. Small aliquots were removed for fluorescence measurements and the balance of the reactions were flash-frozen in liquid $N_2$ and stored at –80° C.

DARET measurements were carried out in a Cary Eclipse spectrophotometer (Varian). Excitation of the Alexa 546 conjugates was at 474 nm, the excitation maximum of the GFP component. Emission was measured at the Alexa 546 fluorescence maximum of 570 nm. In all cases, a dual path length cuvette (10 mm by 2 mm) was utilized and the emission was viewed through the 2 mm path. A solution of 390 µL Toxin Reaction Buffer (50 mM HEPES, pH 7.2; 0.1% v/v TWEEN-20; 10 µM Zn $Cl_2$, 10 mM DTT) and 10 µL of either GFP-SNAP25(Cys-Stop)-Alexa 546 or GFP-SNAP25(Cys-6His)-Alexa 546 was placed in the cuvette and allowed to equilibrate to 30° C. When the DARET measurements, which were taken at 30 sec intervals, were stabilized, 10 µL of recombinant BONT-A light chain (rLC/A) at a concentration of 1.0 µg/µL, 0.5 µg/µL, 0.25 µg/µL, or 0.1 µg/µL was added to the cuvette. Measurements continued to be taken until the signal again stabilized.

The fusion protein substrate used as the starting material for construction of the cysteine-containing derivatives in this embodiment of the invention contains a linker region and a 6×His tag following the SNAP25 134-206 sequence. There are a total of four Cys residues in this substrate, all of them in the conformationally stable GFP domain. The GFP cysteines are not exposed on the surface of the GFP tertiary structure, and reportedly do not react with the maleimide linkers of fluorescent dyes such as Alexa Fluor 546. Plafker, K et al., *J. Biol. Chem.* 277:30121-30127 (2002). A Cys residue was therefore inserted on the C-terminal side of the Type A cleavage site contained in the SNAP-25 sequence as a chemical handle to attach a second fluorophore. Since there was no way to determine a priori what the best attachment position would be, both constructs, the one in which the cysteine was incorporated as the final C-terminal residue and the other variant (immediately before the 6×His tag) were used. The proteins were expressed, purified and used directly in labeling reactions.

The introduced cysteine residues add to the maleimide moiety of the Alexa Fluor 546 dye by Michael addition to form a thio-ether linkage to the fusion protein. A 2-4 M excess of the dye was added to an ice-cold solution of the fusion protein at pH 7.2, and the reaction was allowed to proceed overnight at 4° C. The reaction was quenched with β-mercaptoethanol and the excess dye removed by a combination of centrifugal filtration and dialysis. The dialyzed products were used without further purification for DARET studies. The labeled proteins were flash frozen with liquid $N_2$ and stored at –80° C. between uses.

In a typical fluorescence polarization (FP) assay, proteolysis of the substrate releases a fluorophore-labeled fragment that is significantly smaller (or less bulky) than the parent molecule. The tumbling rate of this fragment is therefore greater than that of the parent and a reduction in polarization of the smaller fragment, compared to the uncleaved fragment, is observed. In the DARET test in which our fusion protein conjugate was treated with rLC/A, however, an increase, rather than a decrease, in polarization was measured. The acceptor fluorophore was excited at the GFP absorbance maximum and DARET measurements were taken at the Alexa emission maximum.

Those of skill in the art will appreciate, however, that in other embodiments of the DARET assays of the present invention, a decrease in polarization may coincide with the disassociation of the molecular features and coincident cessation or diminution of resonance transfer energy.

While not wishing to be limited by theory, the present Applicants believe that the depolarization observed for the intact substrate in this experiment is due to resonance energy transfer between the initially excited acceptor fluorophores and those other (acceptor) molecules having a dipole moment oriented approximately (but not exactly) in the same direction. Since the excited acceptor molecule is not precisely in the same orientation as the originally excited donor fluorophore(s), a decrease in polarization is seen when the polarization of fluorescence from the acceptor fluorophore is measured. This effect is extinguished when resonance transfer energy can no longer occur—i.e., when the donor and acceptor fluorophores are greater than about 100 Angstroms from each other.

Figure 1:
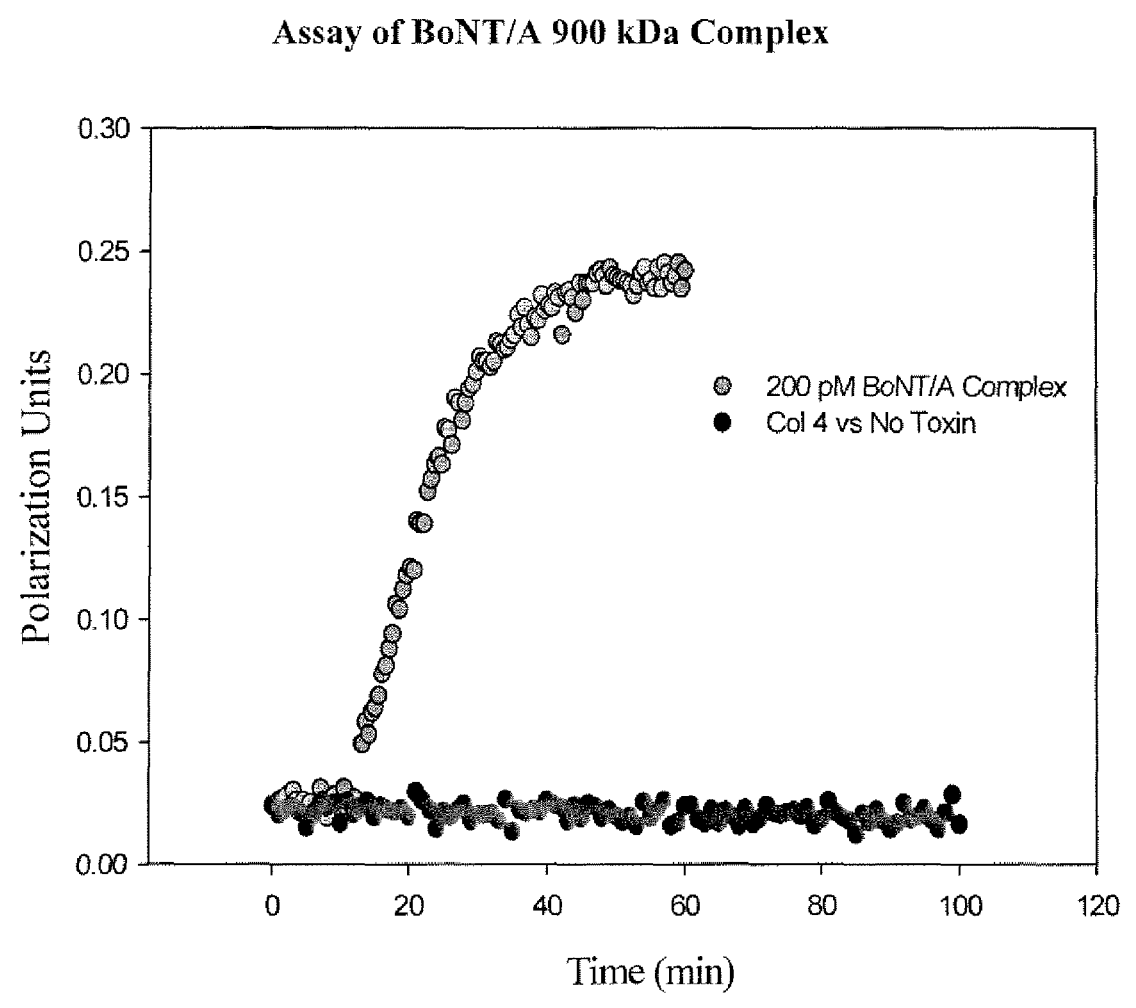

This DARET assay was repeated at different rLC/A concentrations (2.4, 6.0, and 12.0 ng/mL) with the same result. The data plots for two of the tests are shown in FIGS. 1A and 1B.

Example 2

BoNT Protease Assay

Recombinant Substrate and High Capacity Reading Format

In this Example, a DARET assay of BoNT/A and BoNT-E activity was performed using an entirely recombinant substrate molecule, and the results were obtained in both a cuvette-based format and a 96-well format compatible with high throughput screening.

The plasmids encoding the GFP-SNAP25-1×BFP and -2×BFP fusion protein substrates were prepared by modifying vector pQBI GFP to contain a region downstream from the GFP region, containing residues 134-206 of SNAP25, followed immediately by a restriction endonuclease Kpn I site and then a sequence encoding the HIS6 tag. The DNA encoding the blue fluorescent protein (BFP) was obtained from plasmid pQBI T7-BFP, purchased from Clontech (BD Biosciences). The BFP coding region was PCR-amplified using PCR primers designed to eliminate the initial methionine and to introduce Kpn I restriction sites at both ends.

```
Primer BFP-A:
                                      (SEQ ID NO: 9)
5'-GGTACCTTTGTATAGTTCATCCATG-3'

Primer BFP-B:
                                      (SEQ ID NO: 10)
5'-GGTACCGCAAGCAAAGGAGAAGAACTC-3'
```

Two sets of four 50 µL PCR reactions were assembled. Each reaction contained 5 µL 10× Pfu Buffer (Stratagene), 1 µL dNTPs (12.5 mM each; Promega), 1 µL Pfu Turbo DNA polymerase (Stratagene; hotstart addition), 20-50 ng template DNA (pQBI T7-BFP; Clontech), and each primer at a final concentration of 0.2 µM. The reactions were brought to a final volume of 50 µL with nuclease-free water. The PCR thermocycler conditions were:

| Step 1 | 95° C. | 2 min |
|---|---|---|
| Step 2 | 95° C. | 1 min |
| Step 3 | 50° C. | 30 sec |
| Step 4 | 72° C. | 18 min |
| Step 5 | 72° C. | 5 min |
| Step 6 | 10° C. | Hold |

Steps 2-4 were repeated for 25 cycles before steps 5 and 6 were performed. Following thermocycling, 1 µL Dpn I restriction enzyme (New England Biolabs) was added to each reaction and incubated overnight at 37° C. to digest template DNA. The reaction products were analyzed by agarose gel electrophoresis. All reactions contained products of the predicted size, and all were subcloned into the TOPO-Blunt vector, which facilitates the cloning of PCR fragments, which were then used to transform chemically competent E. coli TOP10 cells (Invitrogen). The transformants were selected on LB plates containing 50 µg/mL kanamycin, then grown in and purified from 5 mL overnight cultures by QIAprep Spin Miniprep Kit (Qiagen). Sequencing (Sequetech) identified three clones containing the correct anticipated BFP DNA sequence.

Plasmid pQBI GFP-SNAP25-1×BFP was prepared by ligating the BFP sequence as a Kpn I fragment from pBFP-TOPO into vector pQBI GFP-SNAP25 (KpnI). As a first step, both plasmids were digested with restriction enzyme Kpn I. The linearized pQBI GFP-SNAP25(KpnI) vector and the BFP insert were resolved by agarose gel electrophoresis and then purified by QIAquick® Gel Extraction Kit (Qiagen). The agarose-purified vector was dephosphorylated with shrimp alkaline phosphatase (Roche) and purified again using QIAquick® Gel Extraction Kit (Qiagen). Two ligation reactions were assembled with insert:vector molar ratios of 6:1 and 12:1 and incubated for approximately 20 hours at 16° C. The ligation reaction products were used to transform chemically competent E. coli TOP10 cells (Invitrogen), and electrocompetent E. coli TOP10 cells (Invitrogen) following a 40 min dialysis against sterile deionized water. Transformed colonies were selected on LB plates containing 100 µg/mL ampicillin, then grown in and purified from 5 mL overnight cultures by QIAprep Spin Miniprep Kit (Qiagen). Sequencing (Sequetech) identified three clones containing the correct DNA sequence.

Plasmid pQBI GFP-SNAP25-2×BFP was an unintended product of the ligation reaction which created the 1×BFP plasmid, being the result of a double insertion of the BFP coding region. The initial sequencing did not detect the presence of the two clones because the sequencing reactions that began upstream and downstream of the tandem BFP region did not extend far enough to fully sequence one of the BFP regions and extend into the next. Later, when this was done, the sequencing provided final confirmation that two plasmids had been created, one with a single BFP gene pQBI GFP-SNAP25-1×BFP and the other with two BFP genes in tandem, pQBI GFP-SNAP25-2×BFP.

The sequences of the GFP-SNAP-25-I×BFP DNA (SEQ ID NO: 11) and amino acid sequences (SEQ ID NO: 12) are as follows:

The GFP-SNAP25-1×BFP fusion protein and DNA coding sequences.

```
                                    GFP
~~~~~~~~~~~~~~~~~~~~~~~~~~~~~~~~~~~~~~~~~~~~~~~~~~~~~~~~~~~~~~~~~~~~
  M   A   S    K   G   E    E   L   F    T   G   V    V   P   I    L   V   E    L   D   G
ATGGCTAGC AAAGGAGAA GAACTCTTC ACTGGAGTT GTCCCAATT CTTGTTGAA TTAGATGGT

GFP
~~~~~~~~~~~~~~~~~~~~~~~~~~~~~~~~~~~~~~~~~~~~~~~~~~~~~~~~~~~~~~~~~~~~
  D   V   N    G   H   K    F   S   V    S   G   E    G   E   G    D   A   T    Y   G   K
GGATGTTAAC GGCCACAAG TTCTCTGTC AGTGGAGAG GGTGAAGGT GATGCAACA TACGGAAAA

GFP
~~~~~~~~~~~~~~~~~~~~~~~~~~~~~~~~~~~~~~~~~~~~~~~~~~~~~~~~~~~~~~~~~~~~
  L   T   L    K   F   I    C   T   T    G   K   L    P   V   P    W   P   T    L   V   T
CTTACCCTG AAGTTCATC TGCACTACT GGCAAACTG CCTGTTCCA TGGCCAACA CTAGTCACT

GFP
~~~~~~~~~~~~~~~~~~~~~~~~~~~~~~~~~~~~~~~~~~~~~~~~~~~~~~~~~~~~~~~~~~~~
  T   L   C    Y   G   V    Q   C   F    S   R   Y    P   D   H    M   K   R    H   D   F
ACTCTGTGC TATGGTGTT CAATGCTTT TCAAGATAC CCGGATCAT ATGAAACGG CATGACTTT

GFP
~~~~~~~~~~~~~~~~~~~~~~~~~~~~~~~~~~~~~~~~~~~~~~~~~~~~~~~~~~~~~~~~~~~~
  F   K   S    A   M   P    E   G   Y    V   Q   E    R   T   I    F   F   K    D   D   G
TTCAAGAGT GCCATGCCC GAAGGTTAT GTACAGGAA AGGACCATC TTCTTCAAA GATGACGGC

GFP
~~~~~~~~~~~~~~~~~~~~~~~~~~~~~~~~~~~~~~~~~~~~~~~~~~~~~~~~~~~~~~~~~~~~
  N   Y   K    T   R   A    E   V   K    F   E   G    D   T   L    V   N   R    I   E   L
AACTACAAG ACACGTGCT GAAGTCAAG TTTGAAGGT GATACCCTT GTTAATAGA ATCGAGTTA
```

-continued

GFP

| K | G | I | D | F | K | E | D | G | N | I | L | G | H | K | L | E | Y | N | Y | N |

AAAGGTATT GACTTCAAG GAAGATGGC AACATTCTG GACACAAA TTGGAATAC AACTATAAC

GFP

| S | H | N | V | Y | I | M | A | D | K | Q | K | N | G | I | K | V | N | F | K | T |

TCACACAAT GTATACATC ATGGCAGAC AAACAAAAG AATGGAATC AAAGTGAAC TTCAAGACC

GFP

| R | H | N | I | E | D | G | S | V | Q | L | A | D | H | Y | Q | Q | N | T | P | I |

CGCCACAAC ATTGAAGAT GGAAGCGTT CAACTAGCA GACCATTAT CAACAAAAT ACTCCAATT

GFP

| G | D | G | P | V | L | L | P | D | N | H | Y | L | S | T | Q | S | A | L | S | K |

GGCGATGGC CCTGTCCTT TTACCAGAC AACCATTAC CTGTCCACA CAATCTGCC CTTTCGAAA

GFP

| D | P | N | E | K | R | D | H | M | V | L | L | E | F | V | T | A | A | G | I | T |

GATCCCAAC GAAAAGAGA GACCACATG GTCCTTCTT GAGTTTGTA ACAGCTGCT GGGATTACA

GFP                                                                                   SNAP25 (134-206)

Linker

| H | G | M | D | E | L | Y | N | G | G | A | G | S | G | A | G | G | G | G | I | R |

CATGGCATG GATGAACTG TACAACGGC GGTGCAGGA TCCGGTGCG GGTGGCGGT GGCATCCGG

SNAP25 (134-206)

| R | V | T | N | D | A | R | E | N | E | M | D | E | N | L | E | Q | V | S | G | I |

AGGGTAACA AACGATGCC CGGGAAAAT GAGATGGAT GAGAACCTG GAGCAGGTG AGCGGCATC

SNAP25 (134-206)

| I | G | N | L | R | H | M | A | L | D | M | G | N | E | I | D | T | Q | N | R | Q |

ATCGGAAAC CTCCGCCAT ATGGCTCTA GACATGGGC AATGAGATT GACACCCAG AATCGCCAG

SNAP25 (134-206)

| I | D | R | I | M | E | K | A | D | S | N | K | T | R | I | D | E | A | N | Q | R |

ATCGACAGG ATCATGGAG AAGGCTGAT TCCAACAAA ACCAGAATT GATGAAGCC AACCAACGT

SNAP25 (134-206)                                                   BFP

Linker

| A | T | K | M | L | G | S | G | G | G | G | G | T | A | S | K | G | E | E | L | F |

GCAACAAAG ATGCTGGGA AGTGGTGGC GGTGGCGGT ACCGCAAGC AAAGGAGAA GAACTCTTC

BFP

| T | G | V | V | P | I | L | V | E | L | D | G | D | V | N | G | H | K | F | S | V |

ACTGGAGTT GTCCCAATT CTTGTTGAA TTAGATGGT GATGTTAAC GGCCACAAG TTCTCTGTC

BFP

| S | G | E | G | E | G | D | A | T | Y | G | K | L | T | L | K | F | I | C | T | T |

AGTGGAGAG GGTGAAGGT GATGCAACA TACGGAAAA CTTACCCTG AAGTTCATC TGCACTACT

BFP

| G | K | L | P | V | P | W | P | T | L | V | T | T | L | S | H | G | V | Q | C | F |

GGCAAACTG CCTGTTCCA TGGCCAACA CTAGTCACT ACTCTCTCT CATGGTGTT CAATGCTTT

BFP

| S | R | Y | P | D | H | M | K | R | H | D | F | F | K | S | A | M | P | E | G | Y |

TCAAGATAC CCGGATCAT ATGAAACGG CATGACTTT TTCAAGAGT GCCATGCCC GAAGGTTAT

BFP

| V | Q | E | R | T | I | F | F | K | D | D | G | N | Y | K | T | R | A | E | V | K |

GTACAGGAA AGGACCATC TTCTTCAAA GATGACGGC AACTACAAG ACACGTGCT GAAGTCAAG

```
                        BFP
       ────────────────────────────────────────────────────
    F   E   G   D   T   L   V   N   R   I   E   L   K   G   I   D   F   K   E   D   G
   TTTGAAGGT GATACCCTT GTTAATAGA ATCGAGTTA AAAGGTATT GATTTTAAA GAAGATGGA

BFP
       ────────────────────────────────────────────────────
    N   I   L   G   H   K   L   E   Y   N   Y   N   S   H   N   V   Y   I   M   A   D
   AACATTCTT GGACACAAA TTGGAATAC AACTATAAC TCACACAAT GTATACATC ATGGCAGAC

BFP
       ────────────────────────────────────────────────────
    K   Q   K   N   G   I   K   A   N   F   K   I   R   H   N   I   E   D   G   S   V
   AAACAAAAG AATGGAATC AAAGCGAAC TTCAAGATC CGCCACAAC ATTGAAGAT GGAAGCGTT

BFP
       ────────────────────────────────────────────────────
    Q   L   A   D   H   Y   Q   Q   N   T   P   I   G   D   G   P   V   L   L   P   D
   CAACTAGCA GACCATTAT CAACAAAAT ACTCCAATT GGCGATGGC CCTGTCCTT TTACCAGAC

BFP
       ────────────────────────────────────────────────────
    N   H   Y   L   S   T   Q   S   A   L   S   K   D   P   N   E   K   R   D   H   M
   AACCATTAC CTGTCCACA CAATCTGCC CTTTCGAAA GATCCCAAC GAAAAGAGA GACCACATG

BFP
       ────────────────────────────────────────────────────
                                                                            Linker
                                                                            ~~~
    V   L   L   E   F   V   T   A   A   G   I   T   H   G   M   D   E   L   Y   K   G
   GTCCTTCTT GAGTTTGTA ACAGCTGCT GGGATTACA CATGGCATG GATGAACTA TACAAAGGT Linker
   ~~~
              His Tag
       ─────────────────────
    T   H   H   H   H   H   H
   ACCCATCAC CATCACCAT CAC
```

The nucleotide sequence (SEQ ID NO: 13) and amino acid sequence (SEQ ID NO: 14) of GFP-SNAP25-2×BFP.

```
                        GFP
       ────────────────────────────────────────────────────
    M   A   S   K   G   E   E   L   F   T   G   V   V   P   I   L   V   E   L   D   G
   ATGGCTAGC AAAGGAGAA GAACTCTTC ACTGGAGTT GTCCCAATT CTTGTTGAA TTAGATGGT

GFP
       ────────────────────────────────────────────────────
    D   V   N   G   H   K   F   S   V   S   G   E   G   E   G   D   A   T   Y   G   K
   GATGTTAAC GGCCACAAG TTCTCTGTC AGTGGAGAG GGTGAAGGT GATGCAACA TACGGAAAA

GFP
       ────────────────────────────────────────────────────
    L   T   L   K   F   I   C   T   T   G   K   L   P   V   P   W   P   T   L   V   T
   CTTACCCTG AAGTTCATC TGCACTACT GGCAAACTG CCTGTTCCA TGGCCAACA CTAGTCACT

GFP
       ────────────────────────────────────────────────────
    T   L   C   Y   G   V   Q   C   F   S   R   Y   P   D   H   M   K   R   H   D   F
   ACTCTGTGC TATGGTGTT CAATGCTTT TCAAGATAC CCGGATCAT ATGAAACGG CATGACTTT

GFP
       ────────────────────────────────────────────────────
    F   K   S   A   M   P   E   G   Y   V   Q   E   R   T   I   F   F   K   D   D   G
   TTCAAGAGT GCCATGCCC GAAGGTTAT GTACAGGAA AGGACCATC TTCTTCAAA GATGACGGC

GFP
       ────────────────────────────────────────────────────
    N   Y   K   T   R   A   E   V   K   F   E   G   D   T   L   V   N   R   I   E   L
   AACTACAAG ACACGTGCT GAAGTCAAG TTTGAAGGT GATACCCTT GTTAATAGA ATCGAGTTA

GFP
       ────────────────────────────────────────────────────
    K   G   I   D   F   K   E   D   G   N   I   L   G   H   K   L   E   Y   N   Y   N
   AAAGGTATT GACTTCAAG GAAGATGGC AACATTCTG GACACAAA TTGGAATAC AACTATAAC
```

-continued

```
                                   GFP
     S   H   N       V   Y   I       M   A   D       K   Q   K       N   G   I       K   V   N       F   K   T
    TCACACAAT        GTATACATC       ATGGCAGAC       AAACAAAAG       AATGGAATC       AAAGTGAAC       TTCAAGACC

GFP
     R   H   N       I   E   D       G   S   V       Q   L   A       D   H   Y       Q   Q   N       T   P   I
    CGCCACAAC        ATTGAAGAT       GGAAGCGTT       CAACTAGCA       GACCATTAT       CAACAAAAT       ACTCCAATT

GFP
     G   D   G       F   V   L       L   P   D       N   H   Y       L   S   T       Q   S   A       L   S   K
    GGCGATGGC        CCTGTCCTT       TTACCAGAC       AACCATTAC       CTGTCCACA       CAATCTGCC       CTTTCGAAA

GFP
     D   P   N       E   K   R       D   H   M       V   L   L       E   F   V       T   A   A       G   I   T
    GATCCCAAC        GAAAAGAGA       GACCACATG       GTCCTTCTT       GAGTTTGTA       ACAGCTGCT       GGGATTACA

Linker
                 GFP                                                                            SNAP25 (134-206)
     H   G   M       D   E   L       Y   N   G       G   A   G       S   G   A       G   G   G       G   I   R
    CATGGCATG        GATGAACTG       TACAACGGC       GGTGCAGGA       TCCGGTGCG       GGTGGCGGT       GGCATCCGG SNAP25 (134-206)
     R   V   T       N   D   A       R   E   N       E   M   D       E   N   L       E   Q   V       S   G   I
    AGGGTAACA        AACGATGCC       CGGGAAAAT       GAGATGGAT       GAGAACCTG       GAGCAGGTG       AGCGGCATC SNAP25 (134-206)
     I   G   N       L   R   H       M   A   L       D   M   G       N   E   I       D   T   Q       N   R   Q
    ATCGGAAAC        CTCCGCCAT       ATGGCTCTA       GACATGGGC       AATGAGATT       GACACCCAG       AATCGCCAG SNAP25 (134-206)
     I   D   R       I   M   E       K   A   D       S   N   K       T   R   I       D   E   A       N   Q   R
    ATCGACAGG        ATCATGGAG       AAGGCTGAT       TCCAACAAA       ACCAGAATT       GATGAAGCC       AACCAACGT Linker
         SNAP25 (134-206)                                                 BFP
     A   T   K       M   L   G       S   G   G       G   G   G       T   A   S       K   G   E       E   I   F
    GCAACAAAG        ATGCTGGGA       AGTGGTGGC       GGTGGCGGT       ACCGCAAGC       AAAGGAGAA       GAACTCTTC BFP
     T   G   V       V   P   I       L   V   E       L   D   G       D   V   N       G   H   K       F   S   V
    ACTGGAGTT        GTCCCAATT       CTTGTTGAA       TTAGATGGT       GATGTTAAC       GGCCACAAG       TTCTCTGTC BFP
     S   G   E       G   E   G       D   A   T       Y   G   K       L   T   L       K   F   I       C   T   T
    AGTGGAGAG        GGTGAAGGT       GATGCAACA       TACGGAAAA       CTTACCCTG       AAGTTCATC       TGCACTACT BFP
     G   K   L       P   V   P       W   P   T       L   V   T       T   L   S       H   G   V       Q   C   F
    GGCAAACTG        CCTGTTCCA       TGGCCAACA       CTAGTCACT       ACTCTCTCT       CATGGTGTT       CAATGCTTT BFP
     S   R   Y       P   D   H       M   K   R       H   D   F       F   K   S       A   M   P       E   G   Y
    TCAAGATAC        CCGGATCAT       ATGAAACGG       CATGACTTT       TTCAAGAGT       GCCATGCCC       GAAGGTTAT BFP
     V   Q   E       R   T   I       F   F   K       D   D   G       N   Y   K       T   R   A       E   V   K
    GTACAGGAA        AGGACCATC       TTCTTCAAA       GATGACGGC       AACTACAAG       ACACGTGCT       GAAGTCAAG BFP
     F   E   G       D   T   L       V   N   R       I   E   L       K   G   I       D   F   K       E   D   G
    TTTGAAGGT        GATACCCTT       GTTAATAGA       ATCGAGTTA       AAAGGTATT       GATTTTAAA       GAAGATGGA
```

```
                              BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  N   I   L     G   H   K     L   E   Y     N   Y   N     S   H   N     V   Y   I     M   A   D
 AACATTCTT   GGACACAAA   TTGGAATAC   AACTATAAC   TCACACAAT   GTATACATC   ATGGCAGAC

BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  K   Q   K     N   G   I     K   A   N     F   K   I     R   H   N     I   E   D     G   S   V
 AAACAAAAG   AATGGAATC   AAAGCGAAC   TTCAAGATC   CGCCACAAC   ATTGAAGAT   GGAAGCGTT

BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  Q   L   A     D   H   Y     Q   Q   N     T   P   I     G   D   G     P   V   L     L   P   D
 CAACTAGCA   GACCATTAT   CAACAAAAT   ACTCCAATT   GGCGATGGC   CCTGTCCTT   TTACCAGAC

BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  N   H   Y     L   S   T     Q   S   A     L   S   K     D   P   N     E   K   R     D   H   M
 AACCATTAC   CTGTCCACA   CAATCTGCC   CTTTCGAAA   GATCCCAAC   GAAAAGAGA   GACCACATG

Linker
                                                                                       ~~~
                              BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  V   L   L     E   F   V     T   A   A     G   I   T     H   G   M     D   E   L     Y   K   G
 GTCCTTCTT   GAGTTTGTA   ACAGCTGCT   GGATTACA   CATGGCATG   GATGAACTA   TACAAAGGT Linker
                                                                                       ~~~
                            2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  T   A   S     K   G   E     E   L   F     T   G   V     V   P   I     L   V   E     L   D   G
 ACCGCAAGC   AAAGGAGAA   GAACTCTTC   ACTGGAGTT   GTCCCAATT   CTTGTTGAA   TTAGATGGT 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  D   V   N     G   H   K     F   S   V     S   G   E     G   E   G     D   A   T     Y   G   K
 GATGTTAAC   GGCCACAAG   TTCTCTGTC   AGTGGAGAG   GGTGAAGGT   GATGCAACA   TACGGAAAA 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  L   T   L     K   F   I     C   T   T     G   K   L     P   V   P     W   P   T     L   V   T
 CTTACCCTG   AAGTTCATC   TGCACTACT   GGCAAACTG   CCTGTTCCA   TGGCCAACA   CTAGTCACT 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  T   L   S     H   G   V     Q   C   F     S   R   Y     P   D   H     M   K   R     H   D   F
 ACTCTCTCT   CATGGTGTT   CAATGCTTT   TCAAGATAC   CCGGATCAT   ATGAAACGG   CATGACTTT 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  F   K   S     A   M   P     E   G   Y     V   Q   E     R   T   I     F   F   K     D   D   G
 TTCAAGAGT   GCCATGCCC   GAAGGTTAT   GTACAGGAA   AGGACCATC   TTCTTCAAA   GATGACGGC 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  N   Y   K     T   R   A     E   V   K     F   E   G     D   T   L     V   N   R     I   E   L
 AACTACAAG   ACACGTGCT   GAAGTCAAG   TTTGAAGGT   GATACCCTT   GTTAATAGA   ATCGAGTTA 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  K   G   I     D   F   K     E   D   G     N   I   L     G   H   K     L   E   Y     N   Y   N
 AAAGGTATT   GATTTTAAA   GAAGATGGA   AACATTCTT   GGACACAAA   TTGGAATAC   AACTATAAC 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  S   H   N     V   Y   I     M   A   D     K   Q   K     N   G   I     K   A   N     F   K   I
 TCACACAAT   GTATACATC   ATGGCAGAC   AAACAAAAG   AATGGAATC   AAAGCGAAC   TTCAAGATC 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  R   H   N     I   E   D     G   S   V     Q   L   A     D   H   Y     Q   Q   N     T   P   I
 CGCCACAAC   ATTGAAGAT   GGAAGCGTT   CAACTAGCA   GACCATTAT   CAACAAAAT   ACTCCAATT 2nd BFP
~~~~~~~~~~~~~~~~~~~~~~~~~~~~~~~~~~~~~~~~~~~~~~~~~~~~~~~~~~~~~~~~~~~~~~~~~~~~~~~~~~~~~
  G   D   G     P   V   L     L   P   D     N   H   Y     L   S   T     Q   S   A     L   S   K
 GGCGATGGC   CCTGTCCTT   TTACCAGAC   AACCATTAC   CTGTCCACA   CAATCTGCC   CTTTCGAAA
```

-continued

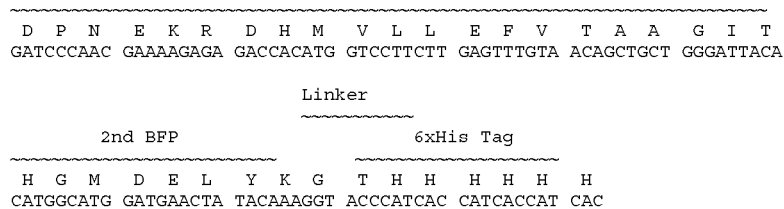

Plasmids pQBI GFP-SNAP25-1×BFP and pQBI GFP-SNAP25-2×BFP were transformed into chemically competent E. coli BL21-(DE3) cells (Novagen) containing the T7 RNA polymerase gene. The transformed cells were spread onto LB plates containing 100 μg/mL ampicillin and incubated overnight at 37° C. Single colonies, or freezer stocks grown from single colonies, were used to inoculate small (1 to 3 mL) starter cultures in either LB (100 μg/mL ampicillin) or PA 0.5 G (100 μg/mL ampicillin) medium. The starter cultures were incubated overnight with shaking at 37° C. These cultures were in turn used at 1000× dilution to inoculate larger cultures in either LB (100 μg/mL ampicillin) medium or ZYP-5052 (100 μg/mL ampicillin) auto-induction medium. Non-inducing medium, PA 0.5 G contains 50 mM $Na_2HPO_4$, 50 mM $KH_2PO_4$, 25 mm $(NH_4)_2SO_4$, 2 mM $MgSO_4$, 0.2× trace metals, 0.5% glycerol, 0.5% glucose and auto inducing medium ZYP-5052 media contains 1% N-Z amine, 0.5% yeast extract 50 mM $Na_2HPO_4$, 50 mM $KH_2PO_4$, 25 mm $(NH_4)_2SO_4$, 2 mM $MgSO_4$, 0.2× trace metals, 0.5% glycerol, 0.05% glucose, 0.2% lactose. The LB cultures were grown at 37° C. with shaking until $A_{600}$ reached 0.62-0.65 absorbance units, at which time they were removed from the incubator and allowed to cool briefly at ambient temperature. Protein expression was then induced by the addition of IPTG to a final concentration of 1 mM and the cultures were incubated overnight at 16° C. with shaking. The ZYP-5052 cultures were grown at 37° C. for 8 hours following inoculation, at which time the temperature was reduced and the cultures were incubated for 16-19 hours at 16° C. with shaking. The protein must be expressed below 30° C. in order for the GFP fluorophore to form optimally. Cells from the expression cultures were collected by centrifugation (30 minutes at 6,000×g, 4° C.) and stored at −80° C. until needed.

For purification of the fusion protein constructs, all steps were undertaken at 4° C. or on ice, except for the chemical cell lysis step, when applicable. For lysis by sonication, cell pellets from 250 mL cultures were each resuspended in 10 mL Column Binding Buffer (25 mM HEPES, pH 8.0; 500 mM NaCl; 10 mM imidazole) and sonicated for 2 minutes in 10-second pulses at an amplitude of 40% using a Branson Digital Sonifier®. For chemical lysis, the cell pellets were resuspended in 5 mL of Lysis Buffer per gram of cell paste at room temperature [Lysis Buffer=BugBuster® reagent (Novagen, cat#: 70584), Protein Extraction Reagent containing 25 U/mL Benzonase nuclease (Novagen, cat#: 70664), 1 KU/mL rLysozyme (Novagen, cat#: 71297), and 1× Protease Inhibitor Cocktail III (Calbiochem, cat#: 539134)] and incubated with gentle rocking for 20 minutes at room temperature. In both cases, the lysates were clarified by centrifugation (36000 RCF, 4° C., 0.5-1 h).

$Co^{2+}$ affinity resin (5 mL Talon® SuperFlow per cell pellet for cells lysed by sonication; 5-10 mL per cell pellet for cells lysed chemically) is equilibrated in a glass or disposable column support (Bio-Rad) by rinsing with 4 column volumes of sterile $dH_2O$ and 4 column volumes of Column Binding Buffer. The lysate is then applied to the column and allowed to enter the column slowly by gravity flow. After the lysate has entered the column, the column is washed with 5 column volumes of Column Binding Buffer.

The protein is eluted with 1-2 column volumes of Column Elution Buffer (25 mM HEPES, pH 8.0; 500 mM NaCl; 500 mM imidazole), which is collected in fractions of ~2.0 mL. The green fractions were combined, concentrated in a 15-mL concentrator (MWCO 30 kDa, Millipore), and desalted by FPLC (BioRad Biologic DuoLogic, QuadTec UV-V is detector) with a HiPrep 26/10 size exclusion column (Pharmacia) and an isocratic mobile phase of chilled Fusion Protein Desalting Buffer (25 mM HEPES, pH 7.2, 4° C.) at a flow rate of 10 mL/min. The desalted protein is collected as a single fraction and the concentration determined by densitometry, with a correction made for the fluorescence level of that lot as necessary. The protein solution is divided into 500 □L aliquots, flash-frozen with liquid nitrogen and stored at −80° C. Once defrosted, a working aliquot is stored at 4° C. for up to 10 days, protected from light.

Cells from a 500 mL expression culture were pelleted by centrifugation (10 min at 6000 RCF, 4° C.), and all but 30 mL of the supernatant solution was decanted. The cell pellets were resuspended in the remaining supernatant solution, yielding a final volume of ~38 mL. To the cell suspension were added 420 μL Protease Inhibitor Cocktail III (Calbiochem, cat#: 539134), 42 μL Benzonase nuclease (Novagen, cat#: 70664), and 4 mL 10× FastBreak™ Cell Lysis Reagent (Promega, cat#: V8573). The mixture was incubated with gentle rocking for 30 min at room temperature and clarified by centrifugation (30 min at 15000 RCF, 4° C.).

A 10 mL IMAC column was prepared by transferring His-Link™ Protein Purification Resin (Promega, cat#: V8821) to a glass column support (Bio-Rad) and draining the storage buffer. The lysate was then applied to the column and allowed to enter the column slowly by gravity flow. After the lysate had entered the column, the column was washed with 10 column volumes of Column Wash Buffer (50 mM HEPES, pH 7.4; 10 mM imidazole). The protein was then eluted with 2.5 column volumes of Column Elution Buffer (50 mM HEPES, pH 7.4; 300 mM imidazole) and collected in fractions of ~2.0 mL. Fractions 4-12 were combined, concentrated in a 15-mL concentrator (MWCO 30 kDa, Millipore) to a final volume of ~4.6 mL, and desalted by FPLC (BioRad Biologic DuoLogic, QuadTec UV-V is detector) with a HiPrep 26/10 size exclusion column (Pharmacia) and an isocratic mobile phase of chilled Fusion Protein Desalting Buffer (25 mM HEPES, pH 7.2, 4° C.) at a flow rate of 10 mL/min. The desalted protein was collected as a single fraction of ~10 mL. The protein solution was divided into forty 250 □L aliquots, flash-frozen with liquid nitrogen and stored at −80° C.

An additional anion exchange purification step for GFP-SNAP25-1×BFP and -2×BFP proteins that had been IMAC-purified was accomplished on a 1 mL UNO-Q1 anion exchange column [BioRad, cat#: 720-0001, and UNO-Q1R (Replacement) cat: 720-0011] with buffers that were pre-chilled and kept on ice throughout the chromatographic procedure. A 500 μL aliquot of each of the fusion proteins GFP-SNAP25-1×BFP (Lot # 1) and GFP-SNAP25-2×BFP (Lot #7) was thawed and each was concentrated to ~100 μL by centrifugal filtration for 15 min at 7,500 RCF, 4° C. (Biomax-30K NMWL membrane 0.5 Centrifugal Filter and Tube, Millipore, Cat #: UFV5BTK00). The sample volumes were then increased to 1 mL by addition of Buffer A (25 mM Tris-HCl, pH7.2) and applied to the column at a flow rate of 0.5 mL/min. The samples were eluted with Buffer B (25 mM Tris-HCl, pH7.2, 1 M NaCl) as specified below (Table 5). Eluted protein was then buffer exchanged one time with 25 mM HEPES, pH7.2.

TABLE 5

AEX elution protocol with step gradients followed by a linear gradient.

| Step | % Buffer B | Volume | Flow Rate |
|---|---|---|---|
| 1 | 5% | 3.0 mL | 0.5 mL/min |
| 2 | 10% | 3.0 mL | 1.5 mL/min |
| 3 | 10 → 40% | 20.0 mL | 1.5 mL/min |
| 4 | 100% | 2.0 mL | 1.5 mL/min |

There was an additional, unexpected result of AEX purification. The proteins used for the tests, GFP-SNAP25-1×BFP and GFP-SNAP25-2×BFP had some inhibitory activity when included in DARET assays, resulting in apparently lower activity of the toxins being assayed. Samples of protein from each lot, before and after AEX purification, were tested as substrates in a DARET assay of 1.4 nM His10-rLC/A. Surprisingly, the inhibitory effects seen previously were completely eliminated in the AEX purified substrates. This DARET assay result indicates that some inhibitory components in the buffer were not efficiently removed by IMAC purification followed by a desalting step, and that AEX column purification is the most promising method for removing residual contamination.

BONT/A 900 kDa complex, BoNT/A 150 kDa dichain toxin, and BoNT/E 160 kDa single chain toxin were purchased from Metabiologics Inc. Nicking the single chain toxin with trypsin produced the active BoNT/E toxin. Additionally, plasmids encoding recombinant versions of the BoNT/A and BoNT/E light chains (termed rLC/A and rLC/E, also containing a polyhistidine tag for facile purification) were expressed in *E. coli* BL21-CodonPlus® (DE3)-RIL cells.

With regard to the GFP-SNAP25-1×BFP and GFP-SNAP25-2×BFP substrates, GFP and BFP are known FRET partners, and energy transfer occurs efficiently between these fluorophores. BFP has an excitation maximum of 387 nm and an emission maximum at 450 nm, while this particular GFP has an excitation maximum at 473 nm and an emission maximum at 509 nm. The SNAP-25 segment of these substrates contains cleavage sites for BoNT/A (between $Gln_{197}$ and $Arg_{198}$), BoNT/E (between $Arg_{180}$ and $Ile_{181}$) and BoNT/C1 (between $Arg_{198}$ and $Ala_{190}$).

The DARET assay may be run in either cuvette or plate formats. The cuvette format is as follows: A solution of 5-12 μM substrate in assay reaction buffer (50 mM HEPES pH 7.2, 0.1% (v/v) Tween® 20; 10 μM $ZnCl_2$; 10 mM dithiothreitol (DTT)) is placed in a quartz cuvette and allowed to equilibrate to 37° C. The substrate is then excited with plane-polarized light at the BFP excitation maximum of 387 nm and the polarization of the light emitted at the GFP wavelength of 509 nm is measured at intervals of 0.5-3 minutes. In the meantime, toxin (or the recombinant light chain) is incubated for 20-30 minutes in the assay reaction buffer. After the substrate signal has stabilized, the toxin is added and polarization measurements are continued for the desired reaction period.

In the plate format, the toxin (or recombinant light chain) is diluted to twice the final reaction concentration in 2× assay reaction buffer and 20 μl aliquots are placed in the wells of a 96-well plate, generally in triplicate. The substrate is also diluted to twice the final reaction concentration of 5-12 μM), and 25 μl aliquots of the substrate are transferred to the corresponding wells of a second 96 well plate. The solutions are warmed to 37° C. and after the toxin has been pre-incubated for 20-30 minutes, 20 μl aliquots of the substrate are transferred to the toxin plate simultaneously and mixed. The plate is transferred to a plate reader and polarization measurements taken every 10-20 minutes for the duration of the reactions. Excitation wavelength is 400 nm (the plate reader limit), emission wavelength is 509 nm, using a 495 nm cutoff filter.

The results of these assays are shown in FIGS. 2-9. FIG. 1 shows the DARET assay of BoNT/A complex (900 kDa) with the GFP-SNAP25-2×BFP substrate in the cuvette-based assay format. Final reaction conditions were 200 pM BoNT/A complex and 10 μM substrate. The excitation wavelength was 387 nm, and the emission wavelength was 509 nm. A negative control contained 8 μM substrate and no toxin. The results clearly indicate that over the course of about 60 minutes the polarization of the toxin-containing sample increased by about 0.20 polarization units, while there was no change for the negative control.

FIG. 2 shows the DARET assay of purified BoNT/A (150 kDa) with the GFP-SNAP25-2×BFP substrate in the cuvette-based assay format. The toxin was added after 11 minutes; the measurement of polarization continued for about 120 minutes. The final reaction mixture contained 300 pM BoNT/A complex and 8 μM substrate. The excitation wavelength was 387 nm, while the emission wavelength was 509 nm. A negative control contained 8 μM substrate and no toxin. Again, an increase in polarization was seen in the cuvette containing the BoNT/A, while no change was seen in the negative control.

FIG. 3 shows the DARET assay of rLC/A in a cuvette-based format. Again, the substrate was GFP-SNAP25-2×BFP, and the toxin was added after the polarization measurements were taken for 14 minutes. The final concentration of the rLC/A toxin was 9 nM, and the sample contained 8 μM substrate. The polarization measurements were taken for approximately 45 minutes. The excitation wavelength was 387 nm, and the emission wavelength was 509 nm.

In FIG. 4 a cuvette-based assay of BoNT/E activity is performed using the DARET assay with the GFP-SNAP25-2×BFP substrate. Final concentrations of toxin and substrate are 200 pM and 8 μM, respectively. Polarization readings are taken for 18 minutes before the toxin is added, and continued for a total of about 110 minutes. Excitation wavelength was 387 nm, emission wavelength was 509 nm.

FIG. 5 shows the plate-based DARET assay of BoNT/A complex (900 kDa) with the GFP-SNAP25-1×BFP substrate. Final reaction conditions employed 8 μM substrate and 25 pM, 50 pM, 100 pM, and 150 pM BoNT/A complex. The excitation wavelength was 400 nm, while the emission wavelength was 509 nm. A negative control was employed containing 8 μM substrate and no toxin. Similar to the cuvette-based assay, the results indicate that over the course of about 90 minutes the polarization of the toxin-containing sample increased, while there was no change for the negative control. In the plate-based assay format changes in polarization were monitored in mP or millipolarization units.

FIGS. 6, 7 and 8 show DARET assays of pure BoNT/A, BoNT/E and rLC/E, respectively, in similar plate-based assay formats. In FIGS. 7 and 8 the GFP-SNAP25-1×BFP substrate was used at a concentration of 8 µM; in FIG. 9 the GFP-SNAP25-1×BFP substrate was used at a concentration of 10 µM. In FIG. 7, the pure BoNT/A toxin was used at 25, 50, 100, 150 and 200 pM concentrations and monitored every 20 minutes for 100 minutes. In FIG. 8, pure BoNT/E was added to the reactions at concentrations of 400, 500, and 1000 pM. Polarization was measured at approximately every 10 minutes. In FIG. 9, the plate-based DARET assay was carried out using 0.5 mM, 1.0 mM, and 1.5 mM rLC/E and polarization measured approximately every 10 minutes. In each case a change in the polarization of the sample was observed as an indication that the substrate was cleaved.

Example 3

DARET Assay of Trypsin Activity

In this example, the GFP-SNAP-25-1×BFP fusion protein was used as an assay substrate for a different protease activity than that contained in a clostridial neurotoxin.

Trypsin is predicted to cleave the SNAP-25(134-206) sequence 11 times. The cleavage pattern of trypsin is as follows: $NH_3—P^4—P^3—P^2—P^1\!=\!=\!P'^1—P'^2—P'^3—P'^4—COOH$, where $=\!=$ is the cleavage site, and $P^1$ is Arg or Lys, although there are exceptions when specific other amino acid residues are present in other positions.

The cuvette format is as follows: A solution of 8 µM GFP-SNAP-25-1×BFP substrate in assay reaction buffer (50 mM HEPES pH 7.2, 0.1% (v/v) Tween® 20; 10 µM $ZnCl_2$; 10 mM dithiothreitol (DTT)), is placed in a quartz cuvette and allowed to equilibrate to 37° C. The substrate is then excited with plane polarized light at the BFP excitation maximum of 387 nm and the polarization of the light emitted at the GFP wavelength of 509 nm is measured at intervals of 0.5-3 minutes. In the meantime, 170 µM trypsin is incubated for 20-30 minutes in the assay reaction buffer. Measurement of the DARET substrate was monitored for 17 minutes, then the trypsin was added and the reaction continued for approximately 90 minutes, with samples monitored approximately every minute.

The results are shown in FIG. 9. As can be seen, the substrate was cleaved so as to separate the two molecular features (the GFP- and the BFP-labeled regions of the fusion protein) almost instantaneously upon addition of trypsin to the reaction mixture, resulting in an increase in fluorescence polarization under DARET assay conditions, as compared to the intact substrate.

Example 4

DARET Detection of Kinase Activity

Peptides containing a chymotrypsin cleavage site near a putative phosphorylation site are subject to differential protease sensitivity, depending upon whether the peptide is phosphorylated or nonphosphorylated.

Chymotrypsin preferentially cleaves at Trp, Tyr and Phe in position P1 (the amino acid residue immediately to the amino terminal side of the cleavage site) and to a lesser extent (taken into account when dealing with low specificity chymotrypsin) at Leu, Met and H is in position P1. Exceptions to these rules are the following: When Trp is found in position P1, the cleavage is blocked when Met or Pro are found in position P1' (the first amino acid on the carboxyl terminal side of the cleavage site) at the same time. Furthermore, Pro in position P1' nearly fully blocks the cleavage, regardless what amino acid is in position P1. When Met is found in position P1, the cleavage is blocked by the presence of Tyr in position P1'. Pearson, R. B., and Kemp, B. E. in *Methods in Enzymology* Vol. 200: 62-81 (T. Hunter and B. M. Sefton (Eds.) San Diego: Academic Press. (1991)) provide a listing of phosphorylation sites and recognition motifs.

A fusion peptide is engineered having the kinase phosphorylation motif of the *B. taurus* $R_{II}$ regulatory subunit of protein kinase A (PKA $R_{II}$), with a chymotrypsin site engineered to occur to the carboxy terminal side of (and positioned close to) this sequence. The peptide is also made to contain a HIS6 tag for purification purposes. This fusion protein is used as a substrate for detecting casein kinase II activity; the recognition motif for casein kinase II (with phosphorylated residues underlined) is: S/T-X-X-E. The PKA $R_{II}$ phosphorylation recognition motif is DSESEEED (SEQ ID NO: 15); both serines in this motif are phosphorylated. The PKA $R_{II}$ sequence (GenBank accession number P00515) is as follows, with the above identified motif underlined.

```
                                            (SEQ ID NO: 16)
SHIQIPPGLT ELLQGYTVEV LRQRPPDLVD FAVDYFTRLR

EARSRASTPP AAPPSGSQDF DPGAGLVADA VADSESEDEE

DLDVPIPGRF DRRVSVCAET YNPDEEEEDT DPRVIHPKTD

QQRCRLQEAC KDILLFKNLD PEQLSQVLDA MFERTVKVDE

HVIDQGDDGD NFYVIERGTY DILVTKDNQT RSVGQYDNHG

SFGELALMYN TPRAATIVAT SEGSLWGLDR VTFRRIIVKN

NAKKRKMFES FIESVPLLKS LEVSERMKIV DVIGEKVYKD

GERIITQGEK ADSFYIIESG EVSILIKSKT KVNKDGENQE

VEIARCHKGQ YFGELALVTN KPRAASAYAV GDVKCLVMDV

QAFERLLGPC MDIMKRNISH YEEQLVKMFG SSMDLIDPGQ
```

This fusion peptide is labeled at the N terminus with coumarin and at the carboxyl terminus with fluorescein.

The fusion peptide is then combined with ATP and the kinase preparation whose activity is to be ascertained and incubated under reaction conditions permitting phosphorylation to occur. Following this, the kinase reaction is quenched, the substrate incubated in a second reaction with chymotrypsin. Under these conditions, the phosphorylated substrate will interfere with chymotrypsin cleavage, whereas the unphosphorylated substrate will be readily cleaved.

The sample is excited using plane polarized light at an absorption maximum wavelength for coumarin (370 nm). Using DARET, polarization monitored at the wavelength of the emission maximum of fluorescein under these conditions will change with increasing concentration of kinase. Cleavage disrupts resonance transfer energy between the donor and acceptor fluorophores on the peptide substrate, whereas uncleaved, phosphorylated peptide substrates maintain resonance transfer energy. Under the reaction conditions, most of the nonphosphorylated, and only a small percentage of phosphorylated peptide is cleaved. Increased kinase activity results in decreased proteolytic cleavage of the substrate (and thus decreased interference with or cessation of resonance transfer energy) and a reduction in depolarization relative to the "no protease" control.

Example 5

A DNA probe is constructed comprising a nucleotide sequence (5'-TTC TCCTTTGCTAGCCAT-3') (SEQ ID NO: 17) to which is attached a 3' synthetic N-hydroxysuccinamide ester linker comprising the compound Alexa Fluor® 350 bound to a distal end as a donor fluorophore. The linker is less than 100 Angstroms in length, ands preferably less than 50 Angstroms in length. Additionally, a nucleic acid of SEQ ID NO: 13 is synthesized and the compound Alexa Fluor® 488 attached via to the 5' end of this DNA sequence via another N-hydroxysuccinamide ester linker.

The labeled nucleic acid strand of sequence SEQ ID NO: 13 is mixed in solution with the labeled DNA probe indicated above, and brought to 98° C. The solution is then slowly cooled to 32° C. while plane polarized light is permitted to illuminate the solution at a wavelength of 346 nm. The fluorescent polarization of the solution is monitored at 519 nm.

As the solution is cooled, and more molecules of the probe and target nucleic acid strand anneal, resonance transfer energy occurs between the Alexa Fluor® 350 donor fluorophore and the Alexa Fluor® 488 acceptor fluorophore, resulting in decreased depolarization observed as the temperature approaches room temperature. Thus, this model system illustrates the general applicability of using DARET for the detection of binding or hybridization of two separate molecules.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the following claims.

We claim:

1. A method for determining whether two or more molecular features in a sample are in proximity, the method comprising:
   a) contacting in said sample, a first molecular feature labeled with a donor fluorophore having a first absorption spectrum and a first emission spectrum, and a second molecular feature labeled with an acceptor fluorophore having a second absorption spectrum overlapping with the first emission spectrum and a second emission spectrum; wherein said first molecular feature and said second molecular feature are on different molecules;
   b) exciting said donor fluorophore with plane polarized light at a wavelength within said first absorption spectrum, thereby resulting in transfer of the excited state energy from the donor to the acceptor fluorophore by intermolecular long-range dipole-dipole coupling, and subsequent emission of fluorescence from the acceptor fluorophore at a wavelength from within said second emission spectrum;
   c) detecting polarization of fluorescence emitted by said acceptor fluorophore at a wavelength within said second emission spectrum; and
   d) correlating a change in polarization of fluorescence emitted by said acceptor fluorophore with a change in proximity of the first and second molecular features to each other, said change relative to the polarization fluorescence emitted by said acceptor fluorophore from either the same sample at a different time or from a control.

2. The method of claim 1 wherein said first molecular feature comprises a lipid moiety, a carbohydrate moiety, a polynucleotide region, or a polypeptide region.

3. The method of claim 1 wherein said second molecular feature comprises a lipid moiety, a carbohydrate moiety, a polynucleotide region, or a polypeptide region.

4. The method of claim 1 wherein said first molecular feature is part of an antibody and said second molecular feature is part of an antigen, or said first molecular feature is part of an antigen and said second molecular feature is part of an antibody.

5. The method of claim 1 wherein said first molecular feature is part of a DNA binding protein and said second molecular feature is part of a polynucleotide region, or said first molecular feature is part of a polynucleotide region and said second molecular feature is part of a DNA binding protein.

6. The method of claim 1 wherein said first molecular feature is part of a lipid and said second molecular feature is part of a membrane protein, or said first molecular feature is part of a membrane protein and said second molecular feature is part of a lipid.

7. The method of claim 1 wherein said first molecular feature is part of a ligand and said second molecular feature is part of a receptor, or said first molecular feature is part of a receptor and said second molecular feature is part of a ligand.

8. The method of claim 1 wherein at least one fluorophore is selected from the group consisting of a green fluorescent protein, a blue fluorescent protein, a red fluorescent protein, a cyan fluorescent protein, a yellow fluorescent protein, a tetracysteine peptide which strongly interacts with a fluorophore, an AGT polypeptide which strongly interacts with a fluorophore, a dehalogenase polypeptide which strongly interacts with a fluorophore, a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye or an infrared fluorescent dye.

9. A method for determining the proximity of two or more molecular features in a sample, the method comprising:
   a) contacting in said sample, a first molecular feature labeled with a donor fluorophore having a first absorption spectrum and a first emission spectrum, and a second molecular feature labeled with an acceptor fluorophore having a second absorption spectrum overlapping with the first emission spectrum and a second emission spectrum; wherein at least one said molecular feature is a lipid moiety, a carbohydrate moiety, or a polynucleotide region;
   b) exciting said donor fluorophore with plane polarized light at a wavelength within said first absorption spectrum, thereby resulting in transfer of the excited state energy from the donor to the acceptor fluorophore by intermolecular long-range dipole-dipole coupling, and subsequent emission of fluorescence from the acceptor fluorophore at a wavelength from within said second emission spectrum;
   c) detecting polarization of fluorescence emitted by said acceptor fluorophore at a wavelength within said second emission spectrum; and
   d) correlating a change in energy transfer and in polarization of fluorescence emitted by said acceptor fluorophore with a change in proximity of the first and second molecular features to each other over time or relative to a control.

10. The method of claim 9 wherein at least one fluorophore is selected from the group consisting of a green fluorescent protein, a blue fluorescent protein, a red fluorescent protein, a cyan fluorescent protein, a yellow fluorescent protein, a tetracysteine peptide which strongly interacts with a fluorophore, an AGT polypeptide which strongly interacts with a fluorophore, a dehalogenase polypeptide which strongly interacts with a fluorophore, a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye or an infrared fluorescent dye.

11. The method of claim 9 wherein said first and second molecular features are located on a single substrate molecule separated by a cleavable target.

12. The method of claim 11 wherein said cleavable target comprises an enzyme susceptible protease cleavage site.

13. A method for determining the proximity of two or more molecular features in a sample, the method comprising:
   a) contacting in said sample, a first molecular feature labeled with a donor fluorophore having a first absorption spectrum and a first emission spectrum, and a second molecular feature labeled with an acceptor fluorophore having a second absorption spectrum overlapping with the first emission spectrum and a second emission spectrum; wherein said first molecular feature and said second molecular feature are on different molecules;
   b) exciting said donor fluorophore with plane polarized light at a wavelength within said first absorption spectrum, thereby resulting in transfer of the excited state energy from the donor to the acceptor fluorophore by intermolecular long-range dipole-dipole coupling, and subsequent emission of fluorescence from the acceptor fluorophore at a wavelength from within said second emission spectrum;
   c) detecting polarization of fluorescence emitted by said acceptor fluorophore at a wavelength within said second emission spectrum; and
   d) correlating a change in polarization of fluorescence emitted by said acceptor fluorophore with a change in proximity of the first and second molecular features to each other, said change relative to the polarization fluorescence emitted by said acceptor fluorophore from either the same sample at a different time or from a control.

14. A method for determining whether two or more molecular features in a sample are in proximity, the method comprising:
   a) contacting in said sample, a first molecular feature labeled with a donor fluorophore having a first absorption spectrum and a first emission spectrum, and a second molecular feature labeled with an acceptor fluorophore having a second absorption spectrum overlapping with the first emission spectrum and a second emission spectrum; wherein at least one said molecular feature is a lipid moiety, a carbohydrate moiety, or a polynucleotide region;
   b) exciting said donor fluorophore with plane polarized light at a wavelength within said first absorption spectrum, thereby resulting in transfer of the excited state energy from the donor to the acceptor fluorophore by intermolecular long-range dipole-dipole coupling, and subsequent emission of fluorescence from the acceptor fluorophore at a wavelength from within said second emission spectrum irradiating said sample with plane polarized light at a wavelength within said first absorption spectrum;
   c) detecting polarization of fluorescence emitted by said acceptor fluorophore at a wavelength within said second emission spectrum; and
   d) correlating a change in energy transfer and in polarization of fluorescence emitted by said acceptor fluorophore with a change in proximity of the first and second molecular features to each other over time or relative to a control.

* * * * *

UNITED STATES PATENT AND TRADEMARK OFFICE
CERTIFICATE OF CORRECTION

PATENT NO.         : 7,998,749 B2
APPLICATION NO.    : 11/548411
DATED              : August 16, 2011
INVENTOR(S)        : Marcella A. Gilmore et al.

Page 1 of 1

It is certified that error appears in the above-identified patent and that said Letters Patent is hereby corrected as shown below:

On page 2, in column 2, under "Other Publications", line 27, delete "Anisotrophy" and insert -- Anisotropy --, therefor.

In column 1, line 37, delete "lysosymes." and insert -- lysosomes. --, therefor.

In column 2, line 55, delete "lanthamide" and insert -- lanthanide --, therefor.

In column 14, line 51-52, delete "Nernstein" and insert -- Bernstein --, therefor.

In column 15, line 58, delete "Discosema" and insert -- Discosoma --, therefor.

In column 15, line 58, delete "Entacmeae" and insert -- Entacmaea --, therefor.

In column 19, line 8, delete "a" and insert -- as --, therefor.

In column 19, line 37, delete "o-phthaldehyde" and insert -- o-phthalaldehyde --, therefor.

In column 22, line 46, delete "anti-hamagluttinin" and insert -- anti-hemagglutinin --, therefor.

In column 22, line 57, delete "hamagluttinin" and insert -- hemagglutinin --, therefor.

In column 24, line 59, delete "proteinacious" and insert -- proteinaceous --, therefor.

In column 37-38, line 48, delete "GGATGTTAAC" and insert -- GATGTTAAC --, therefor.

In column 43-44, line 8, delete "F" and insert -- P --, therefor.

In column 78, line 48-50, in claim 14, after "spectrum" delete "irradiating said sample with plane polarized light at a wavelength within said first absorption spectrum;".

Signed and Sealed this
Twenty-first Day of February, 2012

David J. Kappos
*Director of the United States Patent and Trademark Office*